US011884729B2

(12) United States Patent
Hong et al.

(10) Patent No.: US 11,884,729 B2
(45) Date of Patent: Jan. 30, 2024

(54) ANTI-L1CAM ANTIBODIES AND USES THEREOF

(71) Applicant: ApitBio, Inc., Seoul (KR)

(72) Inventors: Hyo Jeong Hong, Chuncheon-si (KR); Heesu Chae, Seoul (KR); Jisu Hong, Incheon (KR)

(73) Assignee: ApitBio, Inc, Seoul (KR)

( * ) Notice: Subject to any disclaimer, the term of this patent is extended or adjusted under 35 U.S.C. 154(b) by 415 days.

(21) Appl. No.: 17/250,286

(22) PCT Filed: Jun. 27, 2019

(86) PCT No.: PCT/IB2019/055472
§ 371 (c)(1),
(2) Date: Dec. 28, 2020

(87) PCT Pub. No.: WO2020/003210
PCT Pub. Date: Jan. 2, 2020

(65) Prior Publication Data
US 2022/0033494 A1 Feb. 3, 2022

Related U.S. Application Data

(60) Provisional application No. 62/865,871, filed on Jun. 24, 2019.

(30) Foreign Application Priority Data

Jun. 29, 2018 (KR) .................. 10-2018-0075955

(51) Int. Cl.
*C07K 16/28* (2006.01)
*A61K 47/68* (2017.01)
*A61K 39/395* (2006.01)

(52) U.S. Cl.
CPC ...... *C07K 16/2803* (2013.01); *A61K 39/3955* (2013.01); *A61K 47/6849* (2017.08); *C07K 2317/31* (2013.01); *C07K 2317/56* (2013.01); *C07K 2317/565* (2013.01); *C07K 2317/92* (2013.01)

(58) Field of Classification Search
CPC ............ C07K 16/2803; C07K 2317/31; C07K 2317/56; C07K 2317/565; C07K 2317/92; C07K 2317/55; C07K 2317/94; C07K 14/7051; C07K 2317/622; C07K 2319/03; A61K 39/3955; A61K 47/6849; A61K 2039/585; A61K 2039/505; G01N 2333/70503; G01N 33/57407; G01N 33/5743; G01N 33/574; G01N 2333/52; A61P 35/00; C12N 5/0636; C12N 2510/00
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 4,683,195 B1 | 11/1990 | Mullis et al. |
| 5,122,464 A | 6/1992 | Wilson et al. |
| 5,225,539 A | 7/1993 | Winter |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,780 A | 12/1997 | Newman et al. |
| 5,766,886 A | 6/1998 | Studnicka et al. |
| 5,807,715 A | 9/1998 | Morrison et al. |
| 5,814,318 A | 9/1998 | Lonberg et al. |
| 5,837,242 A | 11/1998 | Holliger et al. |
| 5,869,620 A | 2/1999 | Whitlow et al. |
| 5,885,793 A | 3/1999 | Griffiths et al. |
| 5,939,598 A | 8/1999 | Kucherlapati et al. |
| 5,989,830 A | 11/1999 | Davis et al. |
| 6,005,079 A | 12/1999 | Casterman et al. |
| 6,075,181 A | 6/2000 | Kucherlapati et al. |
| 6,132,992 A | 10/2000 | Ledbetter et al. |
| 6,150,184 A | 11/2000 | Evans et al. |
| 6,331,415 B1 | 12/2001 | Cabilly et al. |

(Continued)

FOREIGN PATENT DOCUMENTS

| | | |
|---|---|---|
| EP | 0239400 B1 | 8/1994 |
| EP | 0592106 B1 | 11/2004 |

(Continued)

OTHER PUBLICATIONS

Altschul, S.F., et al., "Basic Local Alignment Search Tool," *Journal of Molecular Biology* 215(3):403-410, Elsevier, United Kingdom (Oct. 1990).

(Continued)

*Primary Examiner* — Julie Wu
*Assistant Examiner* — Francesca Edgingtongiordan
(74) *Attorney, Agent, or Firm* — Sterne, Kessler, Goldstein & Fox P.L.L.C.

(57) ABSTRACT

The present disclosure provides antibodies that specifically bind to L1CAM and compositions comprising such antibodies. Also provided herein are methods for preventing or treating diseases or conditions which comprise a tumor using the anti-L1CAM antibodies.

20 Claims, 9 Drawing Sheets
Specification includes a Sequence Listing.

(56) References Cited

U.S. PATENT DOCUMENTS

| | | |
|---|---|---|
| 6,407,213 B1 | 6/2002 | Carter et al. |
| 6,437,095 B1 | 8/2002 | Lilie et al. |
| 6,989,452 B2 | 1/2006 | Ng et al. |
| 7,087,600 B2 | 8/2006 | Ng et al. |
| 7,129,261 B2 | 10/2006 | Ng et al. |
| 7,183,076 B2 | 2/2007 | Arathoon et al. |
| 7,767,429 B2 | 8/2010 | Bookbinder et al. |
| 7,951,917 B1 | 5/2011 | Arathoon et al. |
| 8,138,313 B2 | 3/2012 | Gast et al. |
| 8,227,577 B2 | 7/2012 | Klein et al. |
| 8,586,713 B2 | 11/2013 | Davis et al. |
| 9,260,521 B2 | 2/2016 | Kelm et al. |
| 9,777,060 B2 | 10/2017 | Hong et al. |
| 10,400,037 B2 | 9/2019 | Altevogt et al. |
| 10,865,242 B2 | 12/2020 | Jensen |
| 2004/0014194 A1 | 1/2004 | Beyer et al. |
| 2005/0042664 A1 | 2/2005 | Wu et al. |
| 2006/0004081 A1 | 1/2006 | Chen et al. |
| 2006/0024317 A1 | 2/2006 | Boyd et al. |
| 2006/0247295 A1 | 11/2006 | Gangwar et al. |
| 2012/0100140 A1 | 4/2012 | Reyes et al. |
| 2015/0344571 A1 | 12/2015 | Hong et al. |
| 2019/0167817 A1 | 6/2019 | Ganesh et al. |
| 2020/0199224 A1 | 6/2020 | Cheung et al. |

FOREIGN PATENT DOCUMENTS

| | | |
|---|---|---|
| EP | 0519596 B1 | 2/2005 |
| EP | 2054083 B1 | 11/2013 |
| EP | 3129471 A1 | 2/2017 |
| EP | 3047039 B1 | 7/2019 |
| EP | 3161482 B1 | 8/2020 |
| KR | 100756051 B1 | 9/2007 |
| KR | 10-2010-0064985 A | 6/2010 |
| KR | 20100064985 A | 6/2010 |
| KR | 101271964 B1 | 6/2013 |
| KR | 10-2014-0026045 A | 3/2014 |
| KR | 20140026045 A | 3/2014 |
| KR | 20140066101 A | 5/2014 |
| WO | WO-8605807 A1 | 10/1986 |
| WO | WO-8901036 A1 | 2/1989 |
| WO | WO-9109967 A1 | 7/1991 |
| WO | WO-9110741 A1 | 7/1991 |
| WO | WO-9317105 A1 | 9/1993 |
| WO | WO-9404678 A1 | 3/1994 |
| WO | WO-9425591 A1 | 11/1994 |
| WO | WO-9517886 A1 | 7/1995 |
| WO | WO-9633735 A1 | 10/1996 |
| WO | WO-9634096 A1 | 10/1996 |
| WO | WO-9712622 A1 | 4/1997 |
| WO | WO-9816654 A1 | 4/1998 |
| WO | WO-9817815 A1 | 4/1998 |
| WO | WO-9817816 A1 | 4/1998 |
| WO | WO-9818934 A1 | 5/1998 |
| WO | WO-9824893 A2 | 6/1998 |
| WO | WO-9846645 A2 | 10/1998 |
| WO | WO-9850433 A2 | 11/1998 |
| WO | WO-9931251 A1 | 6/1999 |
| WO | WO-0144301 A1 | 6/2001 |
| WO | WO-02096910 A1 | 12/2002 |
| WO | WO-2004037198 A2 | 5/2004 |
| WO | WO-2007038658 A2 | 4/2007 |
| WO | WO-2007059404 A2 | 5/2007 |
| WO | WO-2007051081 B1 | 7/2007 |
| WO | WO 2007/114550 | 10/2007 |
| WO | WO-2008083312 A2 | 7/2008 |
| WO | WO-2008103693 A2 | 8/2008 |
| WO | WO-2009059278 A1 | 5/2009 |
| WO | WO-2014077648 A1 | 5/2014 |
| WO | WO 2018/022668 A2 | 2/2018 |
| WO | WO-2020003210 A1 | 1/2020 |
| WO | WO-2020080908 A1 | 4/2020 |

OTHER PUBLICATIONS

Altschul, S.F., et al., "Gapped BLAST and PSI-BLAST: A New Generation of Protein Database Search Programs," *Nucleic Acids Research* 25(17):3389-3402, Oxford University Press, United Kingdom (Sep. 1997).

An, Z., et al., "IgG2m4, an Engineered Antibody Isotype with Reduced Fc Function," Mabs 1(6):572-579, Taylor & Francis, United States (Nov.-Dec. 2009).

Arlt, M. J. E., et al., "Efficient Inhibition of Intra-peritoneal Tumor Growth and Dissemination of Human Ovarian Carcinoma Cells in Nude Mice by Anti-L1-cell Adhesion Molecule Monoclonal Antibody Treatment," Cancer Research 66(2):936-943, American Association for Cancer Research, United States (Jan. 2006).

Baca, M., et al., "Antibody Humanization Using Monovalent Phage Display," The Journal of Biological Chemistry 272(16): 10678-10684, American Society for Biochemistry and Molecular Biology, United States (1997).

Berge, S.M., et al., "Pharmaceutical Salts," *Journal of Pharmaceutical Sciences* 66(1):1-19, Wiley, United States (Jan. 1977).

Bird, R.E., et al., "Single-chain Antigen-binding Proteins," *Science* 242(4877):423-426, Association for the Advancement of Science, United States (Oct. 1988).

Bitter, G.A., et al., "Expression and Secretion Vectors for Yeast," Methods in Enzymology 153:516-544, Academic Press, United States (1987).

Bordusa, F., "Protease-Catalyzed Formation of C—N Bonds," *Highlights in Bioorganic Chemistry: Methods and Applications,* Chapter 5.1, pp. 389-403, Schmuck, C., et al., eds., Wiley-VCH Verlag GmbH & Co. KGaA, Germany (Jan. 2004).

Brennan, M., et al., "Preparation of Bispecific Antibodies by Chemical Recombination of Monoclonal Immunoglobulin G1 Fragments," *Science* 229(4708):81-83, American Association for the Advancement of Science, United States (Jul. 1985).

Bricogne, G., "Bayesian Statistical Viewpoint on Structure Determination: Basic Concepts and Examples," Methods in Enzymology 276:361-423, Academic Press, United States (1997).

Bricogne, G., "Direct Phase Determination by Entropy Maximization and Likelihood Ranking: Status Report and Perspectives," Acta Crystallographica. Section D, Biological Crystallography 49(Pt1):37-60, Wiley-Blackwell, United States (1993).

Brodeur, B.R., et al., "Mouse-Human Myeloma Partners for the Production of Heterohybridomas," in *Monoclonal Antibody Production Techniques and Applications,* Schook, L. B., ed., pp. 51-63, Marcel Dekker, Inc., United States (1987).

Brummell, D.A., et al., "Probing the Combining Site of an Anti-Carbohydrate Antibody by Saturation-Mutagenesis: Role of the Heavy-Chain CDR3 Residues," *Biochemistry* 32(4):1180-1187, American Chemical Society, United States (1993).

Burks, E.A., et al., "In vitro Scanning Saturation Mutagenesis of an Antibody Binding Pocket," *Proceedings of the National Academy of Sciences USA* 94(2):412-417, Plenum Publishing Corporation, United States (1997).

Caldas, C., et al., "Design and Synthesis of Germline-Based Hemi-Humanized Single-Chain Fv Against the CD 18 Surface Antigen," Protein Engineering 13(5):353-360, IRL Press, United Kingdom (2000).

Champe, M., et al., "Monoclonal Antibodies that Block the Activity of Leukocyte Function-Associated Antigen 1 Recognize Three Discrete Epitopes in the Inserted Domain of CD11a," The Journal of Biological Chemistry 270 (3):1388-1394, American Society for Biochemistry and Molecular Biology, United States (1995).

Chayen, N.E., et al., "The Role of Oil in Macromolecular Crystallization," Structure 5(10):1269-1274, Cell Press, United States (1997).

Cheung, R.C., et al., "Epitope-specific Antibody Response to the Surface Antigen of Duck Hepatitis B Virus in Infected Ducks," Virology 176(2):546-552, Academic Press, United States (1990).

Chothia, C. and Lesk, A.M., "Canonical Structures for the Hypervariable Regions of Immunoglobulins," Journal of Molecular Biology 196(4):901-917, Elsevier Science, United States (Aug. 1987).

Cockett, M.I., et al., "High Level Expression of Tissue Inhibitor of Metalloproteinases in Chinese Hamster Ovary Cells Using Gluta-

(56) References Cited

OTHER PUBLICATIONS mine Synthetase Gene Amplification," Biotechnology 8(7):662-667, Nature Publishing Company, United States (1990).
Colbere-Garapin, F., et al., "A New Dominant Hybrid Selective Marker for Higher Eukaryotic Cells," Journal of Molecular Biology 150(1):1-14, Elsevier, United Kingdom (Jul. 1981).
Couto, J.R., et al., "Designing Human Consensus Antibodies with Minimal Positional Templates," Cancer Research 55(23Suppl):5973s-5977s, American Association for Cancer Research, United States (1995).
Couto, J.R., et al., "Anti-BA46 Monoclonal Antibody Mc3: Humanization Using a Novel Positional Consensus and In Vivo and In Vitro Characterization," Cancer Research 55(8):1717-1722, American Association for Cancer Research, United States (1995).
Cunningham, B.C. and Wells, J.A., "High-resolution Epitope Mapping of hGH-receptor Interactions by Alanine-scanning Mutagenesis," Science 244(4908):1081-1085, American Association for the Advancement of Science, United States (Jun. 1989).
De Graaf, A.J., et al., "Nonnatural Amino Acids for Site-specific Protein Conjugation," Bioconjugate Chemistry 20(7):1281-1295, American Chemical Society, United States (2009).
Edelman, G.M et al., "The Covalent Structure of an Entire gammaG Immunoglobulin Molecule," Proceedings of the National Academy of Sciences USA 63(1):78-85, National Academy of Sciences, United States (1969).
Foecking, M.K., et al., "Powerful and Versatile Enhancer-promoter Unit for Mammalian Expression Vectors," Gene 45(1):101-105, North-Holland, Netherlands (1986).
Frese, M.A. and Dierks, T., "Formylglycine Aldehyde Tag-protein Engineering Through a Novel Post-translational Modification," Chembiochem 10(3):425-427, Wiley-VCH Verlag, Germany (2009).
Gautier, A., et al., "An Engineered Protein Tag for Multiprotein Labeling in Living Cells," Chemistry & Biology 15(2):128-136, Elsevier, United States (2008).
Gieger, R., et al., "Crystallogenesis of Biological Macromolecules: Facts and Perspectives," Acta Crystallographica. Section D, Biological Crystallography 50(Pt4):339-350, Wiley-Blackwell, United States (1994).
Gillies, S.D., et al., "High-level Expression of Chimeric Antibodies Using Adapted cDNA Variable Region Cassettes," Journal of Immunological Methods 125(1-2):191-202, Elsevier, Netherlands (1989).
Glennie, M.J., et al., "Preparation and Performance of Bispecific F(Ab' Gamma)2 Antibody Containing Thioether-linked Fab' Gamma Fragments," Journal of Immunology 139(7):2367-2375, American Association of Immunologists, United States (1987).
Goding, J.W., "Production of Monoclonal Antibodies," in Monoclonal Antibodies: Principles and Practice, 2nd ed., pp. 59-103, Academic Press Inc., London (1986).
Greenspan, N.S., et al., "Idiotypes: Structure and Immunogenicity," FASEB Journal 7(5):437-444, The Federation, United States (1993).
Hackenberger, C.P. and Schwarzer, D., "Chemoselective Ligation and Modification Strategies for Peptides and Proteins," Angewandte Chemie 47(52):10030-10074, Wiley-VCH, Germany (2008).
Hammerling, G. J., et al.,eds., "Appendix: Production of Antibody-Producing Hybridomas in the RodentSystems" in Monoclonal Antibodies and T-Cell Hybridomas: Perspectives and Technical Advances, pp. 563-587, Elsevier, Netherlands (1981).
Harlow, E. and Lane D., "Epitope Mapping by Competition Assay," CSH protocols 2006(2):pdb.prot4277, Cold Spring Harbor Laboratory, United States (Jul. 2006).
Harmsen, M.M., et al., "Properties, Production, and Applications of Camelid Single-Domain Antibody Fragments," Applied Microbiology and Biotechnology 77(1):13-22, Springer International, Germany (Nov. 2007).
Huston, J.S., et al., "Protein Engineering of Antibody Binding Sites: Recovery of Specific Activity in an Anti-digoxin Single-chain Fv Analogue Produced in Escherichia coli," Proceedings of the National Academy of Sciences USA 85(16):5879-5883, National Academy of Sciences, United States (Aug. 1988).

Huszar, M., et al., "Expression Profile Analysis in Multiple Human Tumors Identifies L1 (CD171) as a Molecular Marker for Differential Diagnosis and Targeted Therapy," Human Pathology 37(8):1000-1008, W B Saunders, United States, (Aug. 2006).
Inouye, S., et al., "Up-Promoter Mutations in the lpp Gene of Escherichia coli," Nucleic Acids Research 13(9):3101-3110, Oxford University Press, United Kingdom (1985).
International Search Report and Written Opinion for International Application No. PCT/IB2019/055472, Korean Intellectual Property Office, Republic of Korea, dated Nov. 13, 2019, 12 pages.
Jefferis, R., et al., "Human Immunoglobulin Allotypes: Possible Implications for Immunogenicity," Mabs 1(4):332-338, Taylor & Francis, United States (Jul.-Aug. 2009).
Kabat, E.A. and Wu, T.T., "Attempts to Locate Complementarity-Determining Residues in the Variable Positions of Light and Heavy Chains," Annals of the New York Academy of Sciences 190:382-393, Blackwell, United States (1971).
Karpovsky, B., et al., "Production of Target-specific Effector Cells Using Hetero-cross-linked Aggregates Containing Anti-target Cell and Anti-fc Gamma Receptor Antibodies," The Journal of Experimental Medicine 160(6):1686-1701, Rockefeller University Press, United States (1984).
Kilpatrick, K.E., et al., "Rapid Development of Affinity Matured Monoclonal Antibodies Using RIMMS," Hybridoma 16(4):381-389, Mary Ann Liebert, United States (1997).
Kirkland, T.N., et al., "Analysis of the Fine Specificity and Cross-reactivity of Monoclonal Anti-lipid A Antibodies," Journal of Microbiology 137(11):3614-3619, Microbiological Society of Korea, Korea (1986).
Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United States (1999).
Kohler, G. and Milstein, C., "Continuous Cultures of Fused Cells Secreting Antibody of Predefined Specificity," Nature 256(5517):495-497, Macmillan Journals Ltd., United Kingdom (Aug. 1975).
Kostelny, S.A., et al., "Formation of a Bispecific Antibody by the Use of Leucine Zippers," The Journal of Immunology 148(5):1547-1553, American Association of Immunologists, United States (Mar. 1992).
Kozbor, D., et al., "A Human Hybrid Myeloma for Production of Human Monoclonal Antibodies," Journal of Immunology 133(6):3001-3005, American Association of Immunologists, United States (Dec. 1984).
Lau, C., et al., "Chimeric Anti-CD14 IGG2/4 Hybrid Antibodies for Therapeutic Intervention in Pig and Human Models of Inflammation," Journal of Immunology 191(9):4769-4777, American Association of Immunologists, United States (Nov. 2013).
Lee, V., et al., "Specific neural and adrenal medullary antigens detected by antisera to clonal PC12 pheochromocytoma cells," Proc. Natl. Acad Sci. USA 74(11):5021-5025, National Academy of Science, United States (Nov. 1977).
Lefranc, M.P., et al., "IMGT Unique Numbering for Immunoglobulin and T Cell Receptor Variable Domains and Ig Superfamily V-like Domains," Developmental and Comparative Immunology 27(1):55-77, Elsevier Science, United States (Jan. 2003).
Liu, M.A., et al., "Heteroantibody Duplexes Target Cells for Lysis by Cytotoxic T Lymphocytes," Proceedings of the National Academy of Sciences of the United States of America 82(24):8648-8652, National Academy of Sciences, United States (1985).
Logan, J., et al., "Adenovirus Tripartite Leader Sequence Enhances Translation of mRNAs Late After Infection," Proceedings of the National Academy of Sciences USA 81(12):3655-3659, National Academy of Sciences, United States (Jun. 1984).
Lonberg, N., "Human Antibodies From Transgenic Animals," Nature Biotechnology 23(9):1117-1125, Nature America Publishing, United States (Sep. 2005).
Lonberg, N. and Huszar, D., "Human Antibodies from Transgenic Mice," International Reviews of Immunology 13(1):65-93, Informa Healthcare, United Kingdom (1995).
Lowy, I., et al., "Isolation of Transforming DNA: Cloning the Hamster aprt Gene," Cell 22(3):817-823, Cell Press, United States (Dec. 1980).

(56) References Cited

OTHER PUBLICATIONS

McCafferty, J., et al., "Phage Antibodies: Filamentous Phage Displaying Antibody Variable Domains," *Nature* 348(6301):552-554, Nature Publishing Group, London (Dec. 1990).

McGuire, J. C., et al., "NGF stimulates incorporation of fucose or glucosamine into an external glycoprotein in cultured rat PC12 pheochromocytoma cells," *Cell*, 15(2):357-365, Cell Press, United States (Oct. 1978).

McPherson, A., "Current Approaches to Macromolecular Crystallization," European Journal of Biochemistry 189(1):1-23, Blackwell Science Ltd, United Kingdom (1990).

McPherson, A., "Crystallization of Proteins From Polyethylene Glycol," The Journal of Biological Chemistry 251(20):6300-6303, American Society for Biochemistry and Molecular Biology, United States (1976).

Mokyr, M.B., et al., "Realization of the Therapeutic Potential of CTLA-4 Blockade in Low-dose Chemotherapy-treated Tumor-bearing Mice," *Cancer Research* 58(23):5301-5304, American Association for Cancer Research, United States (1998).

Moldenhauer, G., et al., "Identity of HML-1 Antigen on Intestinal Intraepithelial T Cells and of B-ly7 Antigen on Hairy Cell Leukaemia," Scandinavian Journal of Immunology 32(2):77-82, Blackwell Scientific Publications, United Kingdom (1990).

Morea, V., et al., "Antibody Modeling: Implications for Engineering and Design," Methods 20(3):267-279, Academic Press, United States (2000).

Morel, G.A., et al., "Monoclonal Antibodies to Bovine Serum Albumin: Affinity and Specificity Determinations," Molecular Immunology 25(1):7-15, Pergamon Press, United Kingdom (1988).

Morgan, R.A. and Anderson, W.F., "Human Gene Therapy," Annual Review of Biochemistry 62:191-217, Annual Reviews, United States (1993).

Morris, G. E., ed., "Epitope Mapping Protocols," Methods in Molecular Biology, vol. 66, Humana Press, United States (1996).

Morrison, S.L., "Transfectomas Provide Novel Chimeric Antibodies," *Science* 229(4719):1202-1207, Association for the Advancement of Science, United States (Sep. 1985).

Mulligan, R.C., "The Basic Science of Gene Therapy," Science 260(5110):926-932, American Association for the Advancement of Science, United States (1993).

Mulligan, R.C. and Berg, P., "Selection for Animal Cells that Express the *Escherichia coli* Gene Coding for Xanthine-guanine Phosphoribosyltransferase," Proceedings of the National Academy of Sciences USA 78(4):2072-2076, National Academy of Sciences, United States (Apr. 1981).

Muyldermans, S., "Single Domain Camel Antibodies: Current Status," Reviews in Molecular Biotechnology 74(4):277-302, Elsevier Science Publishers, Netherlands (2001).

Myers, E. W., and Miller, W., "Optimal alignments in linear space," *Comput Appl Biosci* 4(1):11-17, IRL Press Ltd., United Kingdom (Mar. 1988).

Nabel, G.J and Felgner, P.L., "Direct Gene Transfer for Immunotherapy and Immunization," Trends in Biotechnology 11(5):211-215, Elsevier Science Publishers, Netherlands (May 1993).

Naganawa, Y., et al., "Generation of mouse-human hybridomas secreting human monoclonal antibodies to Japanese cedar pollen allergen Cry j1," Human Antibodies 14(1-2):27-31, IOS Press, Netherlands (2005).

Needleman, S.B. and Wunsch, C.D., "A General Method Applicable to the Search for Similarities in the Amino Acid Sequence of Two Proteins," *Journal of Molecular Biology* 48(3):443-453, Academic Press, United Kingdom (Mar. 1970).

Nissinoff, A., "Idiotypes: Concepts and Applications," Journal of Immunology 147(8):2429-2438, American Association of Immunologists, United States (1991).

Nuttall, S.D., et al., "Immunoglobulin VH Domains and Beyond: Design and Selection of Single-domain Binding and Targeting Reagents," Current Pharmaceutical Biotechnology 1(3):253-263, Bentham Science Publishers, Netherlands (2000).

O'Hare, K., et al., "Transformation of Mouse Fibroblasts to Methotrexate Resistance by a Recombinant Plasmid Expressing a Prokaryotic Dihydrofolate Reductase," *Proc Natl Acad Sci USA* 78(3):1527-1531, National Academy of Sciences, United States (Mar. 1981).

Oi, V.T. and Morrison, S.L., "Chimeric Antibodies," BioTechniques 4(3):214-221 (1986).

Padlan, E.A., "A Possible Procedure for Reducing the Immunogenicity of Antibody Variable Domains While Preserving their Ligand-binding Properties," Molecular Immunology 28(4-5):489-498, Pergamon Press, United Kingdom (Apr. 1991).

Paulus, H., "Preparation and Biomedical Applications of Bispecific Antibodies," *Behring Institute Mitteilungen* 78:118-132, Behringwerke Ag, Germany (1985).

Pedersen, J. T., et al., "Comparison of surface accessible residues in human and murine immunoglobulin Fv domains. Implication for humanization of murine antibodies," *J Mol Biol* 235(3):959-973, Elsevier, Netherlands (Jan. 1994).

Ren, H., et al., "A Biocompatible Condensation Reaction for the Labeling of Terminal Cysteine Residues on Proteins," Angewandte Chemie 48(51):9658-9662, Wiley-VCH, Germany (2009).

Restifo, N. and Sznol, M., "Cancer: Principles and Practice of Oncology," Cancer Vaccines, Chapter 61, 5th ed., pp. 3023-3043, DeVita et al., eds.,(1997).

Riechmann, L. and Muyldermans, S., "Single Domain Antibodies: Comparison of Camel VH and Camelised Human VH Domains," Journal of Immunological Methods 231(1-2):25-38, Elsevier, Netherlands (Dec. 1999).

Roguska, M.A., et al., "Humanization of Murine Monoclonal Antibodies Through Variable Domain Resurfacing," Proceedings of the National Academy of Sciences of the United States of America 91(3):969-973, National Academy of Sciences, United States (Feb. 1994).

Roguska, M.A., et al., "A Comparison of Two Murine Monoclonal Antibodies Humanized by CDR-grafting and Variable Domain Resurfacing," Protein Engineering 9(10):895-904, Oxford University Press, United Kingdom (1996).

Roux, K.H., et al., "Comparisons of the Ability of Human IgG3 Hinge Mutants, IgM, IgE, and IgA2, to form Small Immune Complexes: A Role for Flexibility and Geometry," The Journal of Immunology 161(8):4083-4090, American Association of Immunologists, United States (Oct. 1998).

Roversi, P., et al., "Modelling Prior Distributions of Atoms for Macromolecular Refinement and Completion," Acta Crystallographica. Section D, Biological Crystallography 56(Pt10):1316-1323, International Union of Crystallography by Munksgaard, United States (2000).

Ruther, U. and Muller-Hill, B., "Easy Identification of cDNA Clones," The EMBO Journal 2(10):1791-1794, IRL Press Ltd, United Kingdom (1983).

Sandhu, J. S., et al., "A Rapid Procedure for the Humanization of Monoclonal Antibodies," Gene 150(2):409-410, Elsevier/North-Holland, Netherlands (1994).

Santerre, R.F., et al., "Expression of Prokaryotic Genes for Hygromycin B and G418 Resistance as Dominant-selection Markers in Mouse L Cells," Gene 30(1-3):147-156, Elsevier/North-Holland, Netherlands (Oct. 1984).

Senter, P.D., "Potent Antibody Drug Conjugates for Cancer Therapy," Current Opinion in Chemical Biology 13(3):235-244, Elsevier, United Kingdom (2009).

Shinmoto, H., et al., "Generation of Mouse-human Hybridomas Secreting Antibodies Against Peanut Allergen Ara H1," Cytotechnology 46(1):19-23, Kluwer Academic Publishers, United States (2004).

Songsivilai, S. and Lachmann, P.J., "Bispecific Antibody: A Tool for Diagnosis and Treatment of Disease," *Clinical and Experimental Immunology* 79(3):315-321, Blackwell Scientific Publications, United Kingdom (1990).

Stahli, C., et al., "Distinction of Epitopes by Monoclonal Antibodies," *Methods in Enzymology* 92:242-253, Academic Press, United States (1983).

Studnicka, G.M., et al., "Human-Engineered Monoclonal Antibodies Retain Full Specific Binding Activity by Preserving Non-CDR Complementarity-Modulating Residues," Protein Engineering 7(6):805-814, Oxford University Press, United Kingdom (1994).

(56) References Cited

OTHER PUBLICATIONS

Sunbul, M. and Yin, J., "Site Specific Protein Labeling by Enzymatic Posttranslational Modification," Organic & Biomolecular Chemistry 7(17):3361-3371, Royal Society of Chemistry, United Kingdom (2009).

Szybalska, E.H. and Szybalski, W., "Genetics of Human Cess Line IV DNA-mediated Heritable Transformation of a Biochemical Trait," Proceedings of the National Academy of Sciences USA 48:2026-2034, National Academy of Sciences, United States (Dec. 1962).

Taki, M., et al., "Transglutaminase-mediated N- and C-terminal Fluorescein Labeling of a Protein Can Support the Native Activity of the Modified Protein," Protein Engineering, Design & Selection 17(2):119-126, Oxford University Press, United Kingdom (2004).

Tan, P., et al., ""Superhumanized" Antibodies: Reduction of Immunogenic Potential by Complementarity-determining Region Grafting With Human Germline Sequences: Application to an Anti-CD28," Journal of Immunology 169(2):1119-1125, American Association of Immunologists, United States (2000).

Taylor, E. V., et al., "Native Chemical Ligation: SemiSynthesis of Post-translationally Modified Proteins and Biological Probes," Protein Engineering 22:65-96, Nucleic Acids and Molecular Biology, United States (2009).

Tolstoshev, P., "Gene Therapy, Concepts, Current Trials and Future Directions," Annual Review of Pharmacology and Toxicology 33:573-596, Annual Reviews, United States (1993).

UniProtKB, "Neural cell adhesion molecule L1," Accession No. P32004, accessed at https://www.uniprot.org/uniprot/P32004, accessed on Jul. 28, 2021, 20 pages.

Van Heeke, G., et al., "Expression of Human Asparagine Synthetase in *Escherichia coli*," The Journal of Biological Chemistry 264(10):5503-5509, American Society for Biochemistry and Molecular Biology, United States (Apr. 1989).

Vidarsson G, et al., "IgG subclasses and allotypes: from structure to effector functions," Front Immunology 5:520, Frontiers Research Foundation, Switzerland (Oct. 2014).

Ward, E.S., et al., "Binding Activities of a Repertoire of Single Immunoglobulin Variable Domains Secreted from *Escherichia coli*," *Nature* 341(6242):544-546, Nature Publishing Group, United Kingdom (Oct. 1989).

Wigler, M., et al., "Transfer of Purified Herpes Virus Thymidine Kinase Gene to Cultured Mouse Cells," *Cell* 11(1):223-232, Cell Press, United States (May 1977).

Wigler, M., et al., "Transformation of Mammalian Cells with an Amplifiable Dominant-Acting Gene," *Proc Natl Acad Sci USA* 77(6):3567-3570, National Academy of Sciences, United States (Jun. 1980).

Wu, G.Y. and Wu, C.H., "Delivery Systems for Gene Therapy," Biotherapy 3(1):87-95, Kluwer Academic Publishers, Netherlands (1991).

Cho, S., et al., "Generation, characterization and preclinical studies of a human anti-L1CAM monoclonal antibody that cross-reacts with rodent L1CAM," MABS 8(2):414-425, Taylor & Frances Group, United Kingdom (Jan. 2016).

Creative Biolabs: "Recombinant Mouse 1-15 Anti-L1CAM Antibody scFv Fragment" In: "Recombinant Mouse Anti-L1CAM Antibody scFv Fragment," Cat. No: HPAB-0398-CN-5{P} Product Information, 2 pages (2018).

Hochnadel, I., et al., "Cancer vaccines and immunotherapeutic approaches in hepatobiliary and pancreatic cancers," Human Vaccines & Immunotherapeutics 13(12):2931-2952, Taylor & Frances Group, United Kingdom (Nov. 2017).

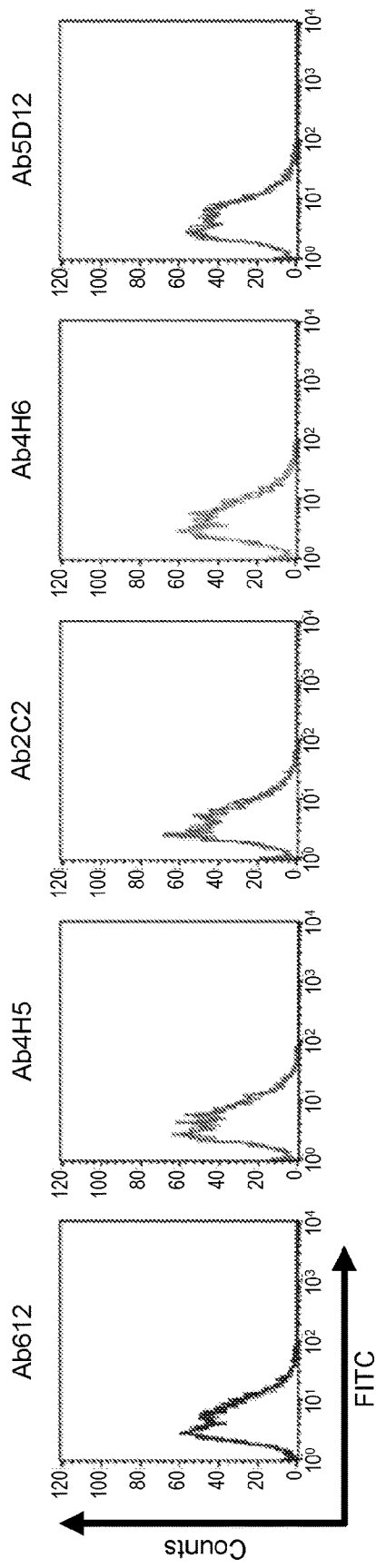
FIG. 1A CHO-DG44
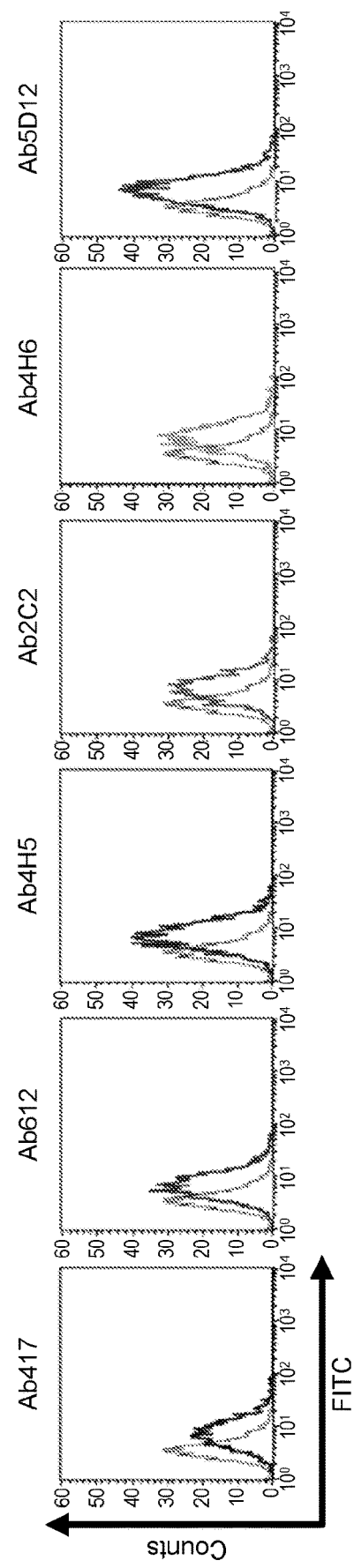
FIG. 1B NCI-H522

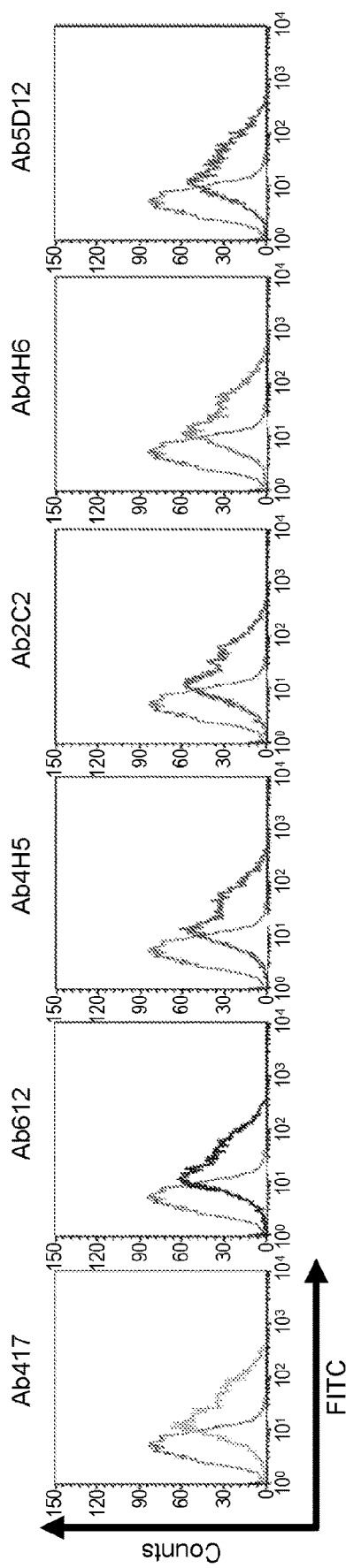
FIG. 1C SKOV3
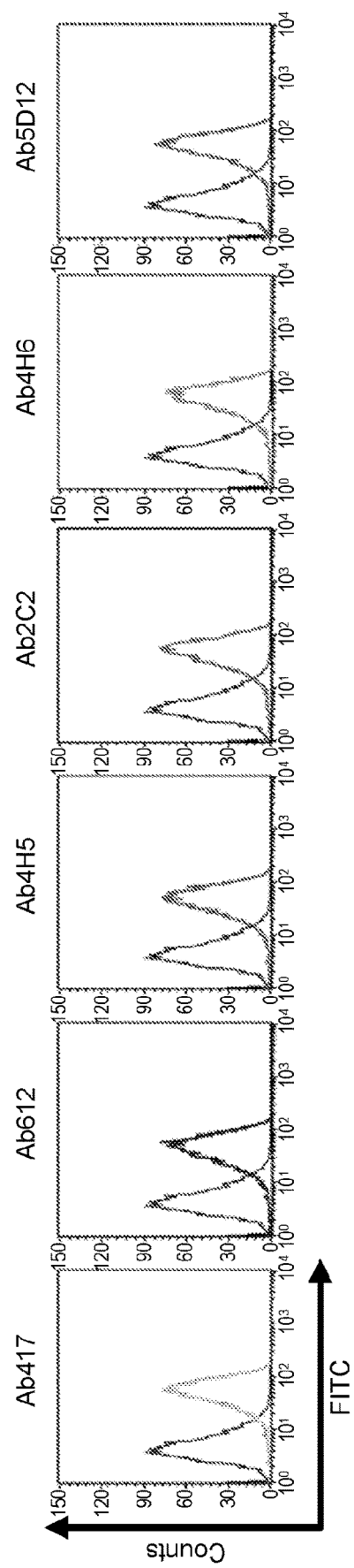
FIG. 1D B16F1

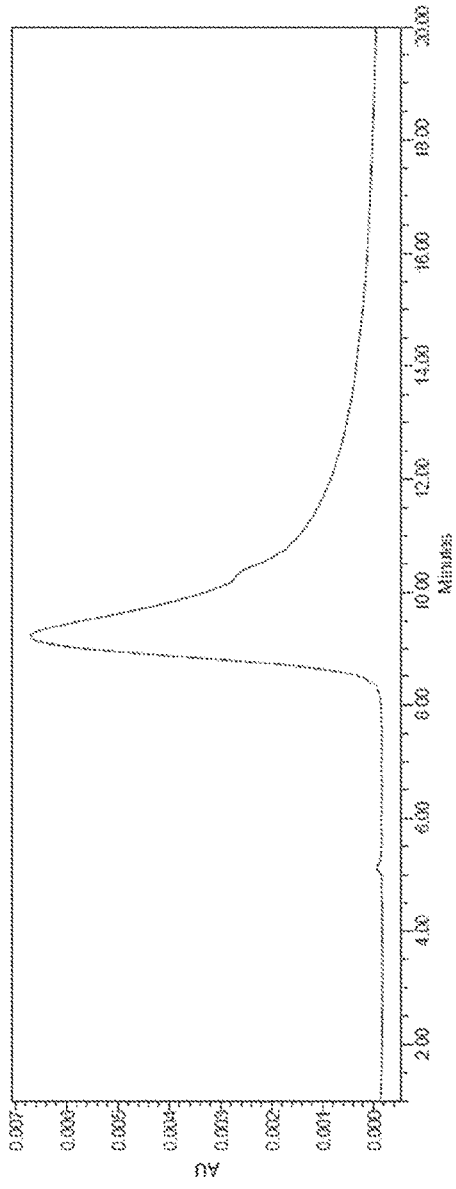
FIG. 2A Ab417
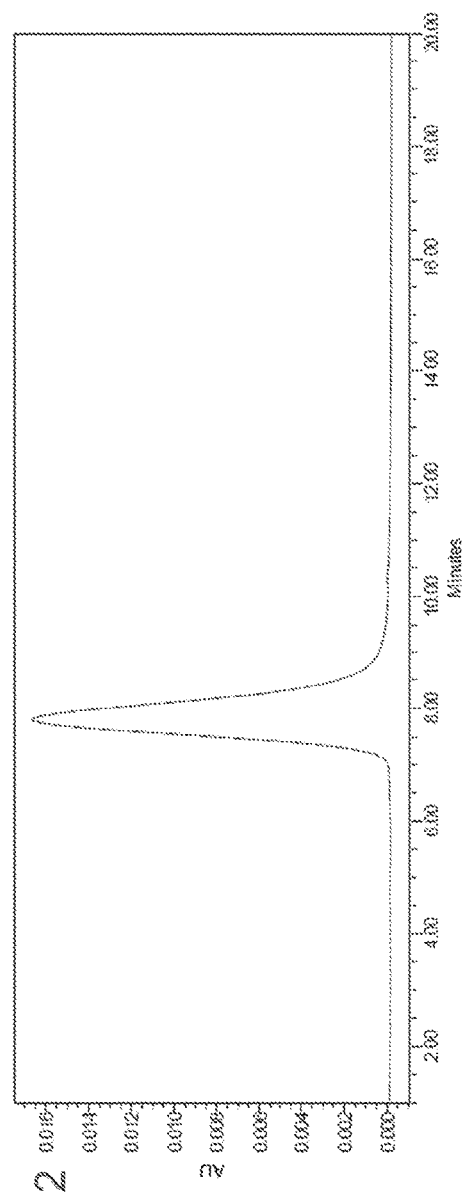
FIG. 2B Ab612

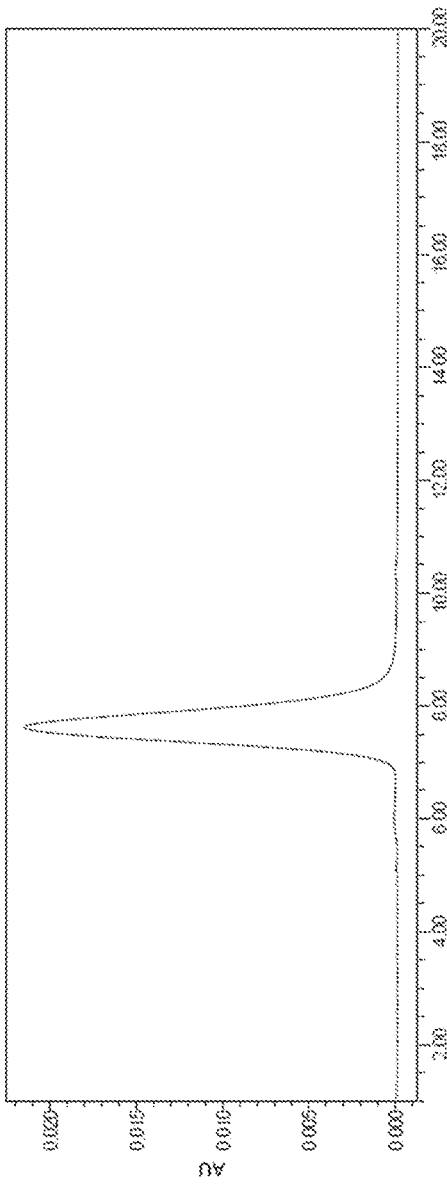
FIG. 2C Ab4H5
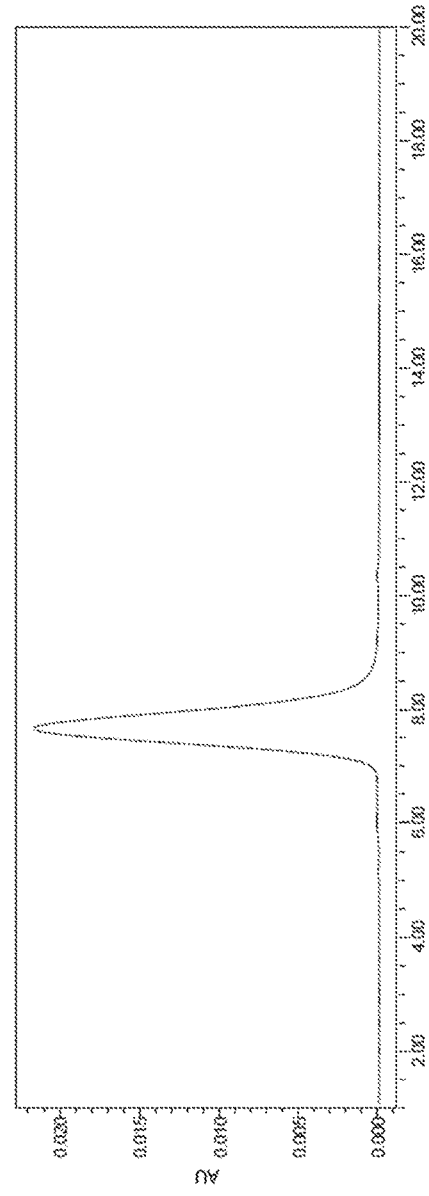
FIG. 2D Ab2C2

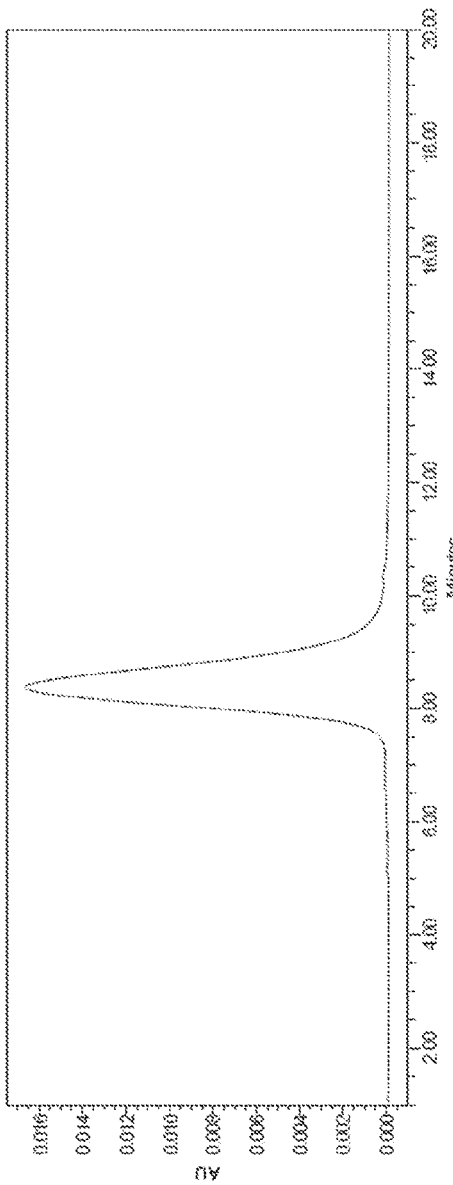
FIG. 2E Ab4H6
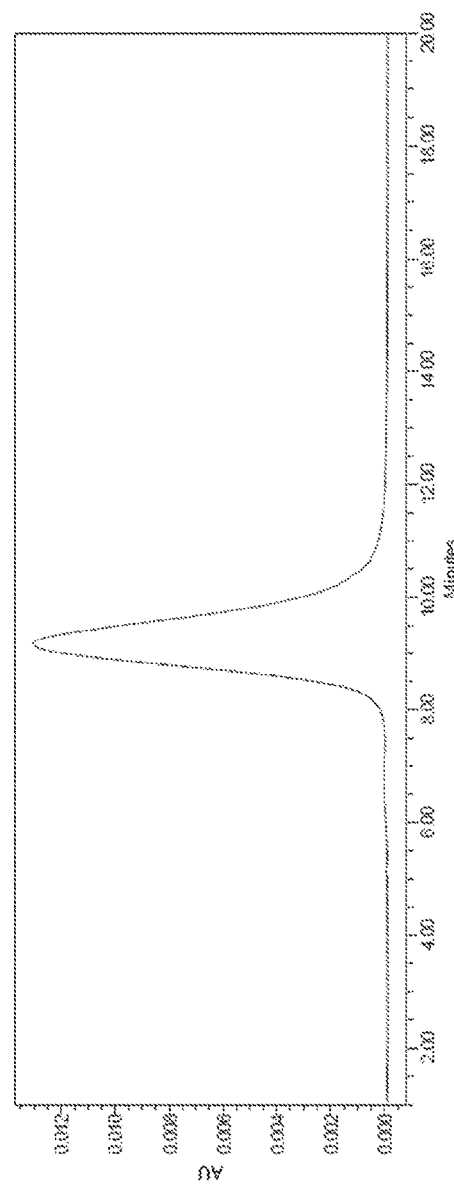
FIG. 2F Ab5D12

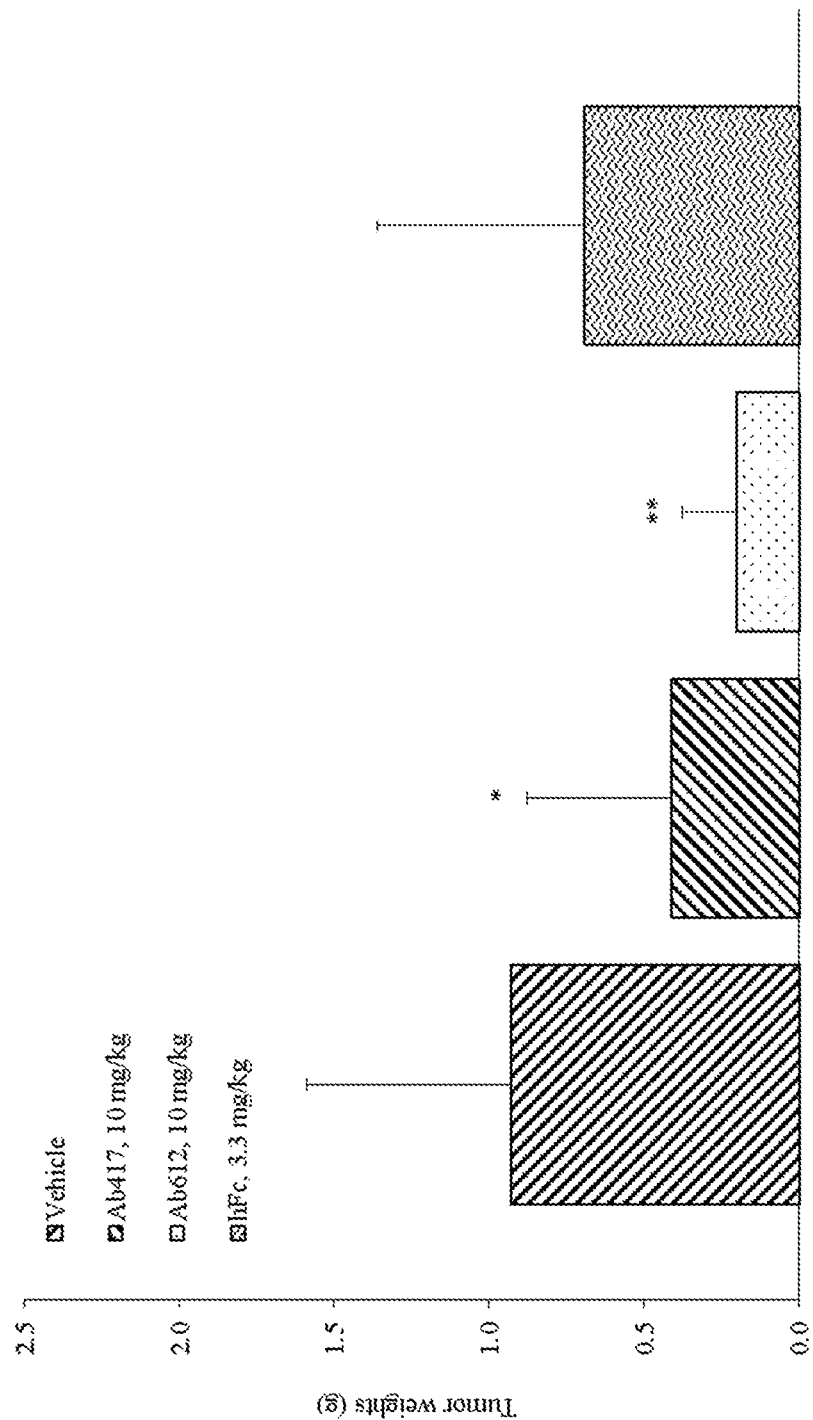

```
                         SEQUENCE LISTING

<160> NUMBER OF SEQ ID NOS: 46

<210> SEQ ID NO 1
<211> LENGTH: 1257
<212> TYPE: PRT
<213> ORGANISM: Artificial Sequence
<220> FEATURE:
<223> OTHER INFORMATION: Human L1CAM

<400> SEQUENCE: 1

Met Val Val Ala Leu Arg Tyr Val Trp Pro Leu Leu Leu Cys Ser Pro
1               5                   10                  15

Cys Leu Leu Ile Gln Ile Pro Glu Glu Tyr Glu Gly His His Val Met
            20                  25                  30

Glu Pro Pro Val Ile Thr Glu Gln Ser Pro Arg Arg Leu Val Val Phe
        35                  40                  45

Pro Thr Asp Asp Ile Ser Leu Lys Cys Glu Ala Ser Gly Lys Pro Glu
    50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
            100                 105                 110

Arg Cys Phe Ala Ser Asn Lys Leu Gly Thr Ala Met Ser His Glu Ile
        115                 120                 125

Arg Leu Met Ala Glu Gly Ala Pro Lys Trp Pro Lys Glu Thr Val Lys
    130                 135                 140

Pro Val Glu Val Glu Glu Gly Glu Ser Val Val Leu Pro Cys Asn Pro
145                 150                 155                 160

Pro Pro Ser Ala Glu Pro Leu Arg Ile Tyr Trp Met Asn Ser Lys Ile
                165                 170                 175

Leu His Ile Lys Gln Asp Glu Arg Val Thr Met Gly Gln Asn Gly Asn
            180                 185                 190

Leu Tyr Phe Ala Asn Val Leu Thr Ser Asp Asn His Ser Asp Tyr Ile
        195                 200                 205

Cys His Ala His Phe Pro Gly Thr Arg Thr Ile Ile Gln Lys Glu Pro
    210                 215                 220

Ile Asp Leu Arg Val Lys Ala Thr Asn Ser Met Ile Asp Arg Lys Pro
225                 230                 235                 240

Arg Leu Leu Phe Pro Thr Asn Ser Ser Ser His Leu Val Ala Leu Gln
                245                 250                 255

Gly Gln Pro Leu Val Leu Glu Cys Ile Ala Glu Gly Phe Pro Thr Pro
```

-continued

```
                260                 265                 270
Thr Ile Lys Trp Leu Arg Pro Ser Gly Pro Met Pro Ala Asp Arg Val
                275                 280                 285
Thr Tyr Gln Asn His Asn Lys Thr Leu Gln Leu Leu Lys Val Gly Glu
                290                 295                 300
Glu Asp Asp Gly Glu Tyr Arg Cys Leu Ala Glu Asn Ser Leu Gly Ser
305                 310                 315                 320
Ala Arg His Ala Tyr Tyr Val Thr Val Glu Ala Pro Tyr Trp Leu
                325                 330                 335
His Lys Pro Gln Ser His Leu Tyr Gly Pro Gly Glu Thr Ala Arg Leu
                340                 345                 350
Asp Cys Gln Val Gln Gly Arg Pro Gln Pro Glu Val Thr Trp Arg Ile
                355                 360                 365
Asn Gly Ile Pro Val Glu Glu Leu Ala Lys Asp Gln Lys Tyr Arg Ile
                370                 375                 380
Gln Arg Gly Ala Leu Ile Leu Ser Asn Val Gln Pro Ser Asp Thr Met
385                 390                 395                 400
Val Thr Gln Cys Glu Ala Arg Asn Arg His Gly Leu Leu Leu Ala Asn
                405                 410                 415
Ala Tyr Ile Tyr Val Val Gln Leu Pro Ala Lys Ile Leu Thr Ala Asp
                420                 425                 430
Asn Gln Thr Tyr Met Ala Val Gln Gly Ser Thr Ala Tyr Leu Leu Cys
                435                 440                 445
Lys Ala Phe Gly Ala Pro Val Pro Ser Val Gln Trp Leu Asp Glu Asp
                450                 455                 460
Gly Thr Thr Val Leu Gln Asp Glu Arg Phe Phe Pro Tyr Ala Asn Gly
465                 470                 475                 480
Thr Leu Gly Ile Arg Asp Leu Gln Ala Asn Asp Thr Gly Arg Tyr Phe
                485                 490                 495
Cys Leu Ala Ala Asn Asp Gln Asn Asn Val Thr Ile Met Ala Asn Leu
                500                 505                 510
Lys Val Lys Asp Ala Thr Gln Ile Thr Gln Gly Pro Arg Ser Thr Ile
                515                 520                 525
Glu Lys Lys Gly Ser Arg Val Thr Phe Thr Cys Gln Ala Ser Phe Asp
                530                 535                 540
Pro Ser Leu Gln Pro Ser Ile Thr Trp Arg Gly Asp Gly Arg Asp Leu
545                 550                 555                 560
Gln Glu Leu Gly Asp Ser Asp Lys Tyr Phe Ile Glu Asp Gly Arg Leu
                565                 570                 575
Val Ile His Ser Leu Asp Tyr Ser Asp Gln Gly Asn Tyr Ser Cys Val
                580                 585                 590
Ala Ser Thr Glu Leu Asp Val Val Glu Ser Arg Ala Gln Leu Leu Val
                595                 600                 605
Val Gly Ser Pro Gly Pro Val Pro Arg Leu Val Leu Ser Asp Leu His
                610                 615                 620
Leu Leu Thr Gln Ser Gln Val Arg Val Ser Trp Ser Pro Ala Glu Asp
625                 630                 635                 640
His Asn Ala Pro Ile Glu Lys Tyr Asp Ile Glu Phe Glu Asp Lys Glu
                645                 650                 655
Met Ala Pro Glu Lys Trp Tyr Ser Leu Gly Lys Val Pro Gly Asn Gln
                660                 665                 670
Thr Ser Thr Thr Leu Lys Leu Ser Pro Tyr Val His Tyr Thr Phe Arg
                675                 680                 685
```

```
Val Thr Ala Ile Asn Lys Tyr Gly Pro Gly Glu Pro Ser Pro Val Ser
    690             695             700

Glu Thr Val Val Thr Pro Glu Ala Pro Glu Lys Asn Pro Val Asp
705             710             715             720

Val Lys Gly Glu Gly Asn Glu Thr Thr Asn Met Val Ile Thr Trp Lys
                725             730             735

Pro Leu Arg Trp Met Asp Trp Asn Ala Pro Gln Val Gln Tyr Arg Val
            740             745             750

Gln Trp Arg Pro Gln Gly Thr Arg Gly Pro Trp Gln Glu Gln Ile Val
        755             760             765

Ser Asp Pro Phe Leu Val Val Ser Asn Thr Ser Thr Phe Val Pro Tyr
    770             775             780

Glu Ile Lys Val Gln Ala Val Asn Ser Gln Gly Lys Gly Pro Glu Pro
785             790             795             800

Gln Val Thr Ile Gly Tyr Ser Gly Glu Asp Tyr Pro Gln Ala Ile Pro
            805             810             815

Glu Leu Glu Gly Ile Glu Ile Leu Asn Ser Ser Ala Val Leu Val Lys
        820             825             830

Trp Arg Pro Val Asp Leu Ala Gln Val Lys Gly His Leu Arg Gly Tyr
    835             840             845

Asn Val Thr Tyr Trp Arg Glu Gly Ser Gln Arg Lys His Ser Lys Arg
850             855             860

His Ile His Lys Asp His Val Val Pro Ala Asn Thr Thr Ser Val
865             870             875             880

Ile Leu Ser Gly Leu Arg Pro Tyr Ser Ser Tyr His Leu Glu Val Gln
            885             890             895

Ala Phe Asn Gly Arg Gly Ser Gly Pro Ala Ser Glu Phe Thr Phe Ser
        900             905             910

Thr Pro Glu Gly Val Pro Gly His Pro Glu Ala Leu His Leu Glu Cys
    915             920             925

Gln Ser Asn Thr Ser Leu Leu Leu Arg Trp Gln Pro Pro Leu Ser His
930             935             940

Asn Gly Val Leu Thr Gly Tyr Val Leu Ser Tyr His Pro Leu Asp Glu
945             950             955             960

Gly Gly Lys Gly Gln Leu Ser Phe Asn Leu Arg Asp Pro Glu Leu Arg
            965             970             975

Thr His Asn Leu Thr Asp Leu Ser Pro His Leu Arg Tyr Arg Phe Gln
        980             985             990

Leu Gln Ala Thr Thr Lys Glu Gly Pro Gly Glu Ala Ile Val Arg Glu
    995             1000            1005

Gly Gly Thr Met Ala Leu Ser Gly Ile Ser Asp Phe Gly Asn Ile
    1010            1015            1020

Ser Ala Thr Ala Gly Glu Asn Tyr Ser Val Val Ser Trp Val Pro
    1025            1030            1035

Lys Glu Gly Gln Cys Asn Phe Arg Phe His Ile Leu Phe Lys Ala
    1040            1045            1050

Leu Gly Glu Glu Lys Gly Gly Ala Ser Leu Ser Pro Gln Tyr Val
    1055            1060            1065

Ser Tyr Asn Gln Ser Ser Tyr Thr Gln Trp Asp Leu Gln Pro Asp
    1070            1075            1080

Thr Asp Tyr Glu Ile His Leu Phe Lys Glu Arg Met Phe Arg His
    1085            1090            1095
```

```
Gln Met Ala Val Lys Thr Asn Gly Thr Gly Arg Val Arg Leu Pro
    1100                1105                1110

Pro Ala Gly Phe Ala Thr Glu Gly Trp Phe Ile Gly Phe Val Ser
    1115                1120                1125

Ala Ile Ile Leu Leu Leu Leu Val Leu Leu Ile Leu Cys Phe Ile
    1130                1135                1140

Lys Arg Ser Lys Gly Gly Lys Tyr Ser Val Lys Asp Lys Glu Asp
    1145                1150                1155

Thr Gln Val Asp Ser Glu Ala Arg Pro Met Lys Asp Glu Thr Phe
    1160                1165                1170

Gly Glu Tyr Arg Ser Leu Glu Ser Asp Asn Glu Glu Lys Ala Phe
    1175                1180                1185

Gly Ser Ser Gln Pro Ser Leu Asn Gly Asp Ile Lys Pro Leu Gly
    1190                1195                1200

Ser Asp Asp Ser Leu Ala Asp Tyr Gly Gly Ser Val Asp Val Gln
    1205                1210                1215

Phe Asn Glu Asp Gly Ser Phe Ile Gly Gln Tyr Ser Gly Lys Lys
    1220                1225                1230

Glu Lys Glu Ala Ala Gly Gly Asn Asp Ser Ser Gly Ala Thr Ser
    1235                1240                1245

Pro Ile Asn Pro Ala Val Ala Leu Glu
    1250                1255

<210> SEQ ID NO 2
<211> LENGTH: 5
<212> TYPE: PRT
<213> ORGANISM: Artificial Sequence
<220> FEATURE:
<223> OTHER INFORMATION: Anti-L1CAM VH-CDR1

<400> SEQUENCE: 2

Arg Phe Gly Met His
1               5

<210> SEQ ID NO 3
<211> LENGTH: 1253
<212> TYPE: PRT
<213> ORGANISM: Artificial Sequence
<220> FEATURE:
<223> OTHER INFORMATION: Human L1CAM isoform 2

<400> SEQUENCE: 3

Met Val Val Ala Leu Arg Tyr Val Trp Pro Leu Leu Cys Ser Pro
1               5                   10                  15

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Ser Gly Lys Pro Glu
        50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
            100                 105                 110

Arg Cys Phe Ala Ser Asn Lys Leu Gly Thr Ala Met Ser His Glu Ile
        115                 120                 125
```

```
Arg Leu Met Ala Glu Gly Ala Pro Lys Trp Pro Lys Glu Thr Val Lys
    130                 135                 140

Pro Val Glu Val Glu Glu Gly Glu Ser Val Val Leu Pro Cys Asn Pro
145                 150                 155                 160

Pro Pro Ser Ala Glu Pro Leu Arg Ile Tyr Trp Met Asn Ser Lys Ile
                165                 170                 175

Leu His Ile Lys Gln Asp Glu Arg Val Thr Met Gly Gln Asn Gly Asn
                180                 185                 190

Leu Tyr Phe Ala Asn Val Leu Thr Ser Asp Asn His Ser Asp Tyr Ile
            195                 200                 205

Cys His Ala His Phe Pro Gly Thr Arg Thr Ile Ile Gln Lys Glu Pro
    210                 215                 220

Ile Asp Leu Arg Val Lys Ala Thr Asn Ser Met Ile Asp Arg Lys Pro
225                 230                 235                 240

Arg Leu Leu Phe Pro Thr Asn Ser Ser Ser His Leu Val Ala Leu Gln
                245                 250                 255

Gly Gln Pro Leu Val Leu Glu Cys Ile Ala Glu Gly Phe Pro Thr Pro
                260                 265                 270

Thr Ile Lys Trp Leu Arg Pro Ser Gly Pro Met Pro Ala Asp Arg Val
            275                 280                 285

Thr Tyr Gln Asn His Asn Lys Thr Leu Gln Leu Leu Lys Val Gly Glu
    290                 295                 300

Glu Asp Asp Gly Glu Tyr Arg Cys Leu Ala Glu Asn Ser Leu Gly Ser
305                 310                 315                 320

Ala Arg His Ala Tyr Tyr Val Thr Val Glu Ala Ala Pro Tyr Trp Leu
                325                 330                 335

His Lys Pro Gln Ser His Leu Tyr Gly Pro Gly Glu Thr Ala Arg Leu
                340                 345                 350

Asp Cys Gln Val Gln Gly Arg Pro Gln Pro Glu Val Thr Trp Arg Ile
            355                 360                 365

Asn Gly Ile Pro Val Glu Glu Leu Ala Lys Asp Gln Lys Tyr Arg Ile
    370                 375                 380

Gln Arg Gly Ala Leu Ile Leu Ser Asn Val Gln Pro Ser Asp Thr Met
385                 390                 395                 400

Val Thr Gln Cys Glu Ala Arg Asn Arg His Gly Leu Leu Leu Ala Asn
                405                 410                 415

Ala Tyr Ile Tyr Val Val Gln Leu Pro Ala Lys Ile Leu Thr Ala Asp
                420                 425                 430

Asn Gln Thr Tyr Met Ala Val Gln Gly Ser Thr Ala Tyr Leu Leu Cys
            435                 440                 445

Lys Ala Phe Gly Ala Pro Val Pro Ser Val Gln Trp Leu Asp Glu Asp
    450                 455                 460

Gly Thr Thr Val Leu Gln Asp Glu Arg Phe Phe Pro Tyr Ala Asn Gly
465                 470                 475                 480

Thr Leu Gly Ile Arg Asp Leu Gln Ala Asn Asp Thr Gly Arg Tyr Phe
                485                 490                 495

Cys Leu Ala Ala Asn Asp Gln Asn Asn Val Thr Ile Met Ala Asn Leu
                500                 505                 510

Lys Val Lys Asp Ala Thr Gln Ile Thr Gln Gly Pro Arg Ser Thr Ile
            515                 520                 525

Glu Lys Lys Gly Ser Arg Val Thr Phe Thr Cys Gln Ala Ser Phe Asp
    530                 535                 540
```

-continued

Pro Ser Leu Gln Pro Ser Ile Thr Trp Arg Gly Asp Gly Arg Asp Leu
545                 550                 555                 560

Gln Glu Leu Gly Asp Ser Asp Lys Tyr Phe Ile Glu Asp Gly Arg Leu
            565                 570                 575

Val Ile His Ser Leu Asp Tyr Ser Asp Gln Gly Asn Tyr Ser Cys Val
        580                 585                 590

Ala Ser Thr Glu Leu Asp Val Val Glu Ser Arg Ala Gln Leu Leu Val
    595                 600                 605

Val Gly Ser Pro Gly Pro Val Pro Arg Leu Val Leu Ser Asp Leu His
610                 615                 620

Leu Leu Thr Gln Ser Gln Val Arg Val Ser Trp Ser Pro Ala Glu Asp
625                 630                 635                 640

His Asn Ala Pro Ile Glu Lys Tyr Asp Ile Glu Phe Glu Asp Lys Glu
            645                 650                 655

Met Ala Pro Glu Lys Trp Tyr Ser Leu Gly Lys Val Pro Gly Asn Gln
        660                 665                 670

Thr Ser Thr Thr Leu Lys Leu Ser Pro Tyr Val His Tyr Thr Phe Arg
    675                 680                 685

Val Thr Ala Ile Asn Lys Tyr Gly Pro Gly Glu Pro Ser Pro Val Ser
690                 695                 700

Glu Thr Val Val Thr Pro Glu Ala Ala Pro Glu Lys Asn Pro Val Asp
705                 710                 715                 720

Val Lys Gly Glu Gly Asn Glu Thr Thr Asn Met Val Ile Thr Trp Lys
            725                 730                 735

Pro Leu Arg Trp Met Asp Trp Asn Ala Pro Gln Val Gln Tyr Arg Val
        740                 745                 750

Gln Trp Arg Pro Gln Gly Thr Arg Gly Pro Trp Gln Glu Gln Ile Val
    755                 760                 765

Ser Asp Pro Phe Leu Val Val Ser Asn Thr Ser Thr Phe Val Pro Tyr
770                 775                 780

Glu Ile Lys Val Gln Ala Val Asn Ser Gln Gly Lys Gly Pro Glu Pro
785                 790                 795                 800

Gln Val Thr Ile Gly Tyr Ser Gly Glu Asp Tyr Pro Gln Ala Ile Pro
            805                 810                 815

Glu Leu Glu Gly Ile Glu Ile Leu Asn Ser Ser Ala Val Leu Val Lys
        820                 825                 830

Trp Arg Pro Val Asp Leu Ala Gln Val Lys Gly His Leu Arg Gly Tyr
    835                 840                 845

Asn Val Thr Tyr Trp Arg Glu Gly Ser Gln Arg Lys His Ser Lys Arg
850                 855                 860

His Ile His Lys Asp His Val Val Val Pro Ala Asn Thr Thr Ser Val
865                 870                 875                 880

Ile Leu Ser Gly Leu Arg Pro Tyr Ser Ser Tyr His Leu Glu Val Gln
            885                 890                 895

Ala Phe Asn Gly Arg Gly Ser Gly Pro Ala Ser Glu Phe Thr Phe Ser
        900                 905                 910

Thr Pro Glu Gly Val Pro Gly His Pro Glu Ala Leu His Leu Glu Cys
    915                 920                 925

Gln Ser Asn Thr Ser Leu Leu Leu Arg Trp Gln Pro Pro Leu Ser His
930                 935                 940

Asn Gly Val Leu Thr Gly Tyr Val Leu Ser Tyr His Pro Leu Asp Glu
945                 950                 955                 960

Gly Gly Lys Gly Gln Leu Ser Phe Asn Leu Arg Asp Pro Glu Leu Arg

```
                    965                 970                 975
Thr His Asn Leu Thr Asp Leu Ser Pro His Leu Arg Tyr Arg Phe Gln
                980                 985                 990
Leu Gln Ala Thr Thr Lys Glu Gly Pro Gly Glu Ala Ile Val Arg Glu
        995                1000                1005
Gly Gly Thr Met Ala Leu Ser Gly Ile Ser Asp Phe Gly Asn Ile
    1010                1015                1020
Ser Ala Thr Ala Gly Glu Asn Tyr Ser Val Val Ser Trp Val Pro
    1025                1030                1035
Lys Glu Gly Gln Cys Asn Phe Arg Phe His Ile Leu Phe Lys Ala
    1040                1045                1050
Leu Gly Glu Glu Lys Gly Gly Ala Ser Leu Ser Pro Gln Tyr Val
    1055                1060                1065
Ser Tyr Asn Gln Ser Ser Tyr Thr Gln Trp Asp Leu Gln Pro Asp
    1070                1075                1080
Thr Asp Tyr Glu Ile His Leu Phe Lys Glu Arg Met Phe Arg His
    1085                1090                1095
Gln Met Ala Val Lys Thr Asn Gly Thr Gly Arg Val Arg Leu Pro
    1100                1105                1110
Pro Ala Gly Phe Ala Thr Glu Gly Trp Phe Ile Gly Phe Val Ser
    1115                1120                1125
Ala Ile Ile Leu Leu Leu Leu Val Leu Leu Ile Leu Cys Phe Ile
    1130                1135                1140
Lys Arg Ser Lys Gly Gly Lys Tyr Ser Val Lys Asp Lys Glu Asp
    1145                1150                1155
Thr Gln Val Asp Ser Glu Ala Arg Pro Met Lys Asp Glu Thr Phe
    1160                1165                1170
Gly Glu Tyr Ser Asp Asn Glu Glu Lys Ala Phe Gly Ser Ser Gln
    1175                1180                1185
Pro Ser Leu Asn Gly Asp Ile Lys Pro Leu Gly Ser Asp Asp Ser
    1190                1195                1200
Leu Ala Asp Tyr Gly Gly Ser Val Asp Val Gln Phe Asn Glu Asp
    1205                1210                1215
Gly Ser Phe Ile Gly Gln Tyr Ser Gly Lys Lys Glu Lys Glu Ala
    1220                1225                1230
Ala Gly Gly Asn Asp Ser Ser Gly Ala Thr Ser Pro Ile Asn Pro
    1235                1240                1245
Ala Val Ala Leu Glu
    1250

<210> SEQ ID NO 4
<211> LENGTH: 12
<212> TYPE: PRT
<213> ORGANISM: Artificial Sequence
<220> FEATURE:
<223> OTHER INFORMATION: Anti-L1CAM VH-CDR3

<400> SEQUENCE: 4

Gly Arg Ala Tyr Gly Ser Gly Ser Leu Phe Asp Pro
1               5                   10

<210> SEQ ID NO 5
<211> LENGTH: 1248
<212> TYPE: PRT
<213> ORGANISM: Artificial Sequence
<220> FEATURE:
<223> OTHER INFORMATION: Human L1CAM isoform 3
```

<400> SEQUENCE: 5

```
Met Val Val Ala Leu Arg Tyr Val Trp Pro Leu Leu Leu Cys Ser Pro
1               5                   10                  15

Cys Leu Leu Ile Gln Ile Pro Glu Glu Leu Met Glu Pro Pro Val Ile
                20                  25                  30

Thr Glu Gln Ser Pro Arg Arg Leu Val Val Phe Pro Thr Asp Asp Ile
            35                  40                  45

Ser Leu Lys Cys Glu Ala Ser Gly Lys Pro Glu Val Gln Phe Arg Trp
        50                  55                  60

Thr Arg Asp Gly Val His Phe Lys Pro Lys Glu Glu Leu Gly Val Thr
65                  70                  75                  80

Val Tyr Gln Ser Pro His Ser Gly Ser Phe Thr Ile Thr Gly Asn Asn
                85                  90                  95

Ser Asn Phe Ala Gln Arg Phe Gln Gly Ile Tyr Arg Cys Phe Ala Ser
                100                 105                 110

Asn Lys Leu Gly Thr Ala Met Ser His Glu Ile Arg Leu Met Ala Glu
            115                 120                 125

Gly Ala Pro Lys Trp Pro Lys Glu Thr Val Lys Pro Val Glu Val Glu
130                 135                 140

Glu Gly Glu Ser Val Val Leu Pro Cys Asn Pro Pro Ser Ala Glu
145                 150                 155                 160

Pro Leu Arg Ile Tyr Trp Met Asn Ser Lys Ile Leu His Ile Lys Gln
                165                 170                 175

Asp Glu Arg Val Thr Met Gly Gln Asn Gly Asn Leu Tyr Phe Ala Asn
            180                 185                 190

Val Leu Thr Ser Asp Asn His Ser Asp Tyr Ile Cys His Ala His Phe
        195                 200                 205

Pro Gly Thr Arg Thr Ile Ile Gln Lys Glu Pro Ile Asp Leu Arg Val
210                 215                 220

Lys Ala Thr Asn Ser Met Ile Asp Arg Lys Pro Arg Leu Leu Phe Pro
225                 230                 235                 240

Thr Asn Ser Ser Ser His Leu Val Ala Leu Gln Gly Gln Pro Leu Val
                245                 250                 255

Leu Glu Cys Ile Ala Glu Gly Phe Pro Thr Pro Thr Ile Lys Trp Leu
            260                 265                 270

Arg Pro Ser Gly Pro Met Pro Ala Asp Arg Val Thr Tyr Gln Asn His
        275                 280                 285

Asn Lys Thr Leu Gln Leu Leu Lys Val Gly Glu Glu Asp Asp Gly Glu
    290                 295                 300

Tyr Arg Cys Leu Ala Glu Asn Ser Leu Gly Ser Ala Arg His Ala Tyr
305                 310                 315                 320

Tyr Val Thr Val Glu Ala Ala Pro Tyr Trp Leu His Lys Pro Gln Ser
                325                 330                 335

His Leu Tyr Gly Pro Gly Glu Thr Ala Arg Leu Asp Cys Gln Val Gln
            340                 345                 350

Gly Arg Pro Gln Pro Glu Val Thr Trp Arg Ile Asn Gly Ile Pro Val
        355                 360                 365

Glu Glu Leu Ala Lys Asp Gln Lys Tyr Arg Ile Gln Arg Gly Ala Leu
    370                 375                 380

Ile Leu Ser Asn Val Gln Pro Ser Asp Thr Met Val Thr Gln Cys Glu
385                 390                 395                 400

Ala Arg Asn Arg His Gly Leu Leu Leu Ala Asn Ala Tyr Ile Tyr Val
```

```
                405                 410                 415
Val Gln Leu Pro Ala Lys Ile Leu Thr Ala Asp Asn Gln Thr Tyr Met
            420                 425                 430
Ala Val Gln Gly Ser Thr Ala Tyr Leu Leu Cys Lys Ala Phe Gly Ala
        435                 440                 445
Pro Val Pro Ser Val Gln Trp Leu Asp Glu Asp Gly Thr Thr Val Leu
    450                 455                 460
Gln Asp Glu Arg Phe Phe Pro Tyr Ala Asn Gly Thr Leu Gly Ile Arg
465                 470                 475                 480
Asp Leu Gln Ala Asn Asp Thr Gly Arg Tyr Phe Cys Leu Ala Ala Asn
            485                 490                 495
Asp Gln Asn Asn Val Thr Ile Met Ala Asn Leu Lys Val Lys Asp Ala
        500                 505                 510
Thr Gln Ile Thr Gln Gly Pro Arg Ser Thr Ile Glu Lys Lys Gly Ser
    515                 520                 525
Arg Val Thr Phe Thr Cys Gln Ala Ser Phe Asp Pro Ser Leu Gln Pro
530                 535                 540
Ser Ile Thr Trp Arg Gly Asp Gly Arg Asp Leu Gln Glu Leu Gly Asp
545                 550                 555                 560
Ser Asp Lys Tyr Phe Ile Glu Asp Gly Arg Leu Val Ile His Ser Leu
            565                 570                 575
Asp Tyr Ser Asp Gln Gly Asn Tyr Ser Cys Val Ala Ser Thr Glu Leu
        580                 585                 590
Asp Val Val Glu Ser Arg Ala Gln Leu Leu Val Val Gly Ser Pro Gly
    595                 600                 605
Pro Val Pro Arg Leu Val Leu Ser Asp Leu His Leu Leu Thr Gln Ser
610                 615                 620
Gln Val Arg Val Ser Trp Ser Pro Ala Glu Asp His Asn Ala Pro Ile
625                 630                 635                 640
Glu Lys Tyr Asp Ile Glu Phe Glu Asp Lys Glu Met Ala Pro Glu Lys
            645                 650                 655
Trp Tyr Ser Leu Gly Lys Val Pro Gly Asn Gln Thr Ser Thr Thr Leu
        660                 665                 670
Lys Leu Ser Pro Tyr Val His Tyr Thr Phe Arg Val Thr Ala Ile Asn
    675                 680                 685
Lys Tyr Gly Pro Gly Glu Pro Ser Pro Val Ser Glu Thr Val Val Thr
690                 695                 700
Pro Glu Ala Ala Pro Glu Lys Asn Pro Val Asp Val Lys Gly Glu Gly
705                 710                 715                 720
Asn Glu Thr Thr Asn Met Val Ile Thr Trp Lys Pro Leu Arg Trp Met
            725                 730                 735
Asp Trp Asn Ala Pro Gln Val Gln Tyr Arg Val Gln Trp Arg Pro Gln
        740                 745                 750
Gly Thr Arg Gly Pro Trp Gln Glu Gln Ile Val Ser Asp Pro Phe Leu
    755                 760                 765
Val Val Ser Asn Thr Ser Thr Phe Val Pro Tyr Glu Ile Lys Val Gln
770                 775                 780
Ala Val Asn Ser Gln Gly Lys Gly Pro Glu Pro Gln Val Thr Ile Gly
785                 790                 795                 800
Tyr Ser Gly Glu Asp Tyr Pro Gln Ala Ile Pro Glu Leu Glu Gly Ile
            805                 810                 815
Glu Ile Leu Asn Ser Ser Ala Val Leu Val Lys Trp Arg Pro Val Asp
        820                 825                 830
```

```
Leu Ala Gln Val Lys Gly His Leu Arg Gly Tyr Asn Val Thr Tyr Trp
        835                 840                 845

Arg Glu Gly Ser Gln Arg Lys His Ser Lys Arg His Ile His Lys Asp
    850                 855                 860

His Val Val Pro Ala Asn Thr Thr Ser Val Ile Leu Ser Gly Leu
865                 870                 875                 880

Arg Pro Tyr Ser Tyr His Leu Glu Val Gln Ala Phe Asn Gly Arg
                885                 890                 895

Gly Ser Gly Pro Ala Ser Glu Phe Thr Phe Ser Thr Pro Glu Gly Val
                900                 905                 910

Pro Gly His Pro Glu Ala Leu His Leu Glu Cys Gln Ser Asn Thr Ser
        915                 920                 925

Leu Leu Leu Arg Trp Gln Pro Pro Leu Ser His Asn Gly Val Leu Thr
    930                 935                 940

Gly Tyr Val Leu Ser Tyr His Pro Leu Asp Glu Gly Lys Gly Gln
945                 950                 955                 960

Leu Ser Phe Asn Leu Arg Asp Pro Glu Leu Arg Thr His Asn Leu Thr
                965                 970                 975

Asp Leu Ser Pro His Leu Arg Tyr Arg Phe Gln Leu Gln Ala Thr Thr
        980                 985                 990

Lys Glu Gly Pro Gly Glu Ala Ile Val Arg Glu Gly Gly Thr Met Ala
    995                 1000                1005

Leu Ser Gly Ile Ser Asp Phe Gly Asn Ile Ser Ala Thr Ala Gly
    1010                1015                1020

Glu Asn Tyr Ser Val Val Ser Trp Val Pro Lys Glu Gly Gln Cys
    1025                1030                1035

Asn Phe Arg Phe His Ile Leu Phe Lys Ala Leu Gly Glu Glu Lys
    1040                1045                1050

Gly Gly Ala Ser Leu Ser Pro Gln Tyr Val Ser Tyr Asn Gln Ser
    1055                1060                1065

Ser Tyr Thr Gln Trp Asp Leu Gln Pro Asp Thr Asp Tyr Glu Ile
    1070                1075                1080

His Leu Phe Lys Glu Arg Met Phe Arg His Gln Met Ala Val Lys
    1085                1090                1095

Thr Asn Gly Thr Gly Arg Val Arg Leu Pro Pro Ala Gly Phe Ala
    1100                1105                1110

Thr Glu Gly Trp Phe Ile Gly Phe Val Ser Ala Ile Ile Leu Leu
    1115                1120                1125

Leu Leu Val Leu Leu Ile Leu Cys Phe Ile Lys Arg Ser Lys Gly
    1130                1135                1140

Gly Lys Tyr Ser Val Lys Asp Lys Glu Asp Thr Gln Val Asp Ser
    1145                1150                1155

Glu Ala Arg Pro Met Lys Asp Glu Thr Phe Gly Glu Tyr Ser Asp
    1160                1165                1170

Asn Glu Glu Lys Ala Phe Gly Ser Ser Gln Pro Ser Leu Asn Gly
    1175                1180                1185

Asp Ile Lys Pro Leu Gly Ser Asp Asp Ser Leu Ala Asp Tyr Gly
    1190                1195                1200

Gly Ser Val Asp Val Gln Phe Asn Glu Asp Gly Ser Phe Ile Gly
    1205                1210                1215

Gln Tyr Ser Gly Lys Lys Glu Lys Glu Ala Ala Gly Gly Asn Asp
    1220                1225                1230
```

Ser Ser Gly Ala Thr Ser Pro Ile Asn Pro Ala Val Ala Leu Glu
       1235               1240                1245

<210> SEQ ID NO 6
<211> LENGTH: 11
<212> TYPE: PRT
<213> ORGANISM: Artificial Sequence
<220> FEATURE:
<223> OTHER INFORMATION: VL CDR1 mAb417

<400> SEQUENCE: 6

Arg Ala Ser Arg Thr Ile Ser Ile Tyr Val Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Anti-L1CAM VL-CDR2

<400> SEQUENCE: 7

Ala Ala Ser Asn Leu His Ser
1               5

<210> SEQ ID NO 8
<211> LENGTH: 363
<212> TYPE: DNA
<213> ORGANISM: Artificial Sequence
<220> FEATURE:
<223> OTHER INFORMATION: Ab612 Variable Heavy Chain Polynucleotide
      Sequence

<400> SEQUENCE: 8
gaggtgcagc tggtggagag cggcggcggc gtggtgcagc ccggcggcag cctgagactg      60
agctgcgccg ccagcggctt caccttcagc agattcggca tgcactgggt gagacaggcc     120
cccggcaagg gcctggagtg ggtggccttc atcagcaacg acggcagcaa caagtactac     180
gccgacagcg tgaagggcag attcaccatc agcagagaca cagcgccaa caccctgtac      240 ctgcagatga acagcctgag agccgaggac accgccgtgt actactgcgc cagaggcaga     300
gcctacggca gcggcagcct gttcgacccc tggggccagg gcaccctggt gaccgtgagc     360
agc                                                                   363

<210> SEQ ID NO 9
<211> LENGTH: 17
<212> TYPE: PRT
<213> ORGANISM: Artificial Sequence
<220> FEATURE:
<223> OTHER INFORMATION: VH CDR2 mAb417

<400> SEQUENCE: 9

Phe Ile Ser Asn Asp Gly Ser Asn Lys Tyr Tyr Ala Asp Ser Val Lys
1               5                   10                  15

Gly

<210> SEQ ID NO 10
<211> LENGTH: 17
<212> TYPE: PRT
<213> ORGANISM: Artificial Sequence
<220> FEATURE:
<223> OTHER INFORMATION: Anti-L1CAM VH-CDR2

<400> SEQUENCE: 10

Phe Ile Ser Asn Glu Gly Ser Asn Lys Tyr Tyr Ala Asp Ser Val Lys
1               5                   10                  15
Gly

<210> SEQ ID NO 11
<211> LENGTH: 10
<212> TYPE: PRT
<213> ORGANISM: Artificial Sequence
<220> FEATURE:
<223> OTHER INFORMATION: VL CDR3 mAb417

<400> SEQUENCE: 11

Gln Gln Ser Ile Gly Arg Gly Val Val Thr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Anti-L1CAM VL-CDR1

<400> SEQUENCE: 12

Arg Ala Ser Arg Thr Ile Ser Ser Tyr Val Asn
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Ab612 VL CDR3

<400> SEQUENCE: 13

Gln Gln Ser Ile Gly Arg Gly Pro Val Thr
1               5                   10

<210> SEQ ID NO 14
<211> LENGTH: 363
<212> TYPE: DNA
<213> ORGANISM: Artificial Sequence
<220> FEATURE:
<223> OTHER INFORMATION: Ab4H5 Variable Heavy Chain Polynucleotide
      Sequence

<400> SEQUENCE: 14
gaggtgcagc tggtggagag cggcggcggc gtggtgcagc ccggcggcag cctgagactg      60
agctgcgccg ccagcggctt caccttcagc agattcggca tgcactgggt gagacaggcc     120
cccggcaagg gcctggagtg ggtggccttc atcagcaacg agggcagcaa caagtactac     180
gccgacagcg tgaagggcag attcaccatc agcagagaca cagcgccaa caccctgtac     240 ctgcagatga acagcctgag agccgaggac accgccgtgt actactgcgc cagaggcaga     300
gcctacggca gcggcagcct gttcgacccc tggggccagg gcaccctggt gaccgtgagc     360
agc                                                                   363

<210> SEQ ID NO 15
<211> LENGTH: 10
<212> TYPE: PRT
<213> ORGANISM: Artificial Sequence
<220> FEATURE:
<223> OTHER INFORMATION: Ab4H5 VL-CDR3

<400> SEQUENCE: 15

Gln Gln Ala Gly Phe Tyr Thr Pro Trp Thr
1               5                   10

<210> SEQ ID NO 16
<211> LENGTH: 363
<212> TYPE: DNA
<213> ORGANISM: Artificial Sequence
<220> FEATURE:
<223> OTHER INFORMATION: Ab2C2 Variable Heavy Chain Polynucleotide
      Sequence

<400> SEQUENCE: 16
gaggtgcagc tggtggagag cggcggcggc gtggtgcagc ccggcggcag cctgagactg      60
agctgcgccg ccagcggctt caccttcagc agattcggca tgcactgggt gagacaggcc     120
cccggcaagg gcctggagtg ggtggccttc atcagcaacg agggcagcaa caagtactac     180
gccgacagcg tgaagggcag attcaccatc agcagagaca cagcgccaa caccctgtac      240 ctgcagatga acagcctgag agccgaggac accgccgtgt actactgcgc cagaggcaga     300
gcctacggca gcggcagcct gttcgacccc tggggccagg gcaccctggt gaccgtgagc     360
agc                                                                   363

<210> SEQ ID NO 17
<211> LENGTH: 10
<212> TYPE: PRT
<213> ORGANISM: Artificial Sequence
<220> FEATURE:
<223> OTHER INFORMATION: Ab2C2 VL CDR3

<400> SEQUENCE: 17

Gln Gln Ala Gly Phe Tyr Ser Pro Trp Thr
1               5                   10

<210> SEQ ID NO 18
<211> LENGTH: 363
<212> TYPE: DNA
<213> ORGANISM: Artificial Sequence
<220> FEATURE:
<223> OTHER INFORMATION: Ab4H6 Variable Heavy Chain Polynucleotide
      Sequence

<400> SEQUENCE: 18
gaggtgcagc tggtggagag cggcggcggc gtggtgcagc ccggcggcag cctgagactg      60
agctgcgccg ccagcggctt caccttcagc agattcggca tgcactgggt gagacaggcc     120
cccggcaagg gcctggagtg ggtggccttc atcagcaacg agggcagcaa caagtactac     180
gccgacagcg tgaagggcag attcaccatc agcagagaca cagcgccaa caccctgtac      240 ctgcagatga acagcctgag agccgaggac accgccgtgt actactgcgc cagaggcaga     300
gcctacggca gcggcagcct gttcgacccc tggggccagg gcaccctggt gaccgtgagc     360
agc                                                                   363

<210> SEQ ID NO 19
<211> LENGTH: 10
<212> TYPE: PRT
<213> ORGANISM: Artificial Sequence
<220> FEATURE:
<223> OTHER INFORMATION: Ab4H6 VL-CDR3

<400> SEQUENCE: 19

Gln Gln Ser Leu His Phe Tyr Pro Trp Thr
1               5                   10

<210> SEQ ID NO 20
<211> LENGTH: 215
<212> TYPE: PRT
<213> ORGANISM: Artificial Sequence
<220> FEATURE:
<223> OTHER INFORMATION: Ab5D12 Light Chain Amino Acid Sequence

<400> SEQUENCE: 20

Asp Ile Gln Leu Thr Gln Ser Pro Ser Leu Ser Ala Ser Val Gly
1               5                   10                  15

Asp Arg Val Thr Ile Thr Cys Arg Ala Ser Arg Thr Ile Ser Ser Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Leu Val Trp Tyr Pro
            85                  90                  95

Trp Thr Phe Gly Gln Gly Thr Lys Leu Glu Ile Lys Arg Thr Val Ala
        100                 105                 110

Ala Pro Ser Val Phe Ile Phe Pro Pro Ser Asp Glu Gln Leu Lys Ser
    115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205

Ser Phe Asn Arg Gly Glu Cys
    210                 215

<210> SEQ ID NO 21
<211> LENGTH: 10
<212> TYPE: PRT
<213> ORGANISM: Artificial Sequence
<220> FEATURE:
<223> OTHER INFORMATION: Ab5D12 VL-CDR3

<400> SEQUENCE: 21

Gln Gln Ser Leu Val Trp Tyr Pro Trp Thr
1               5                   10

<210> SEQ ID NO 22
<211> LENGTH: 363
<212> TYPE: DNA
<213> ORGANISM: Artificial Sequence
<220> FEATURE:
<223> OTHER INFORMATION: Ab5D12 Variable Heavy Chain Polynucleotide
      Sequence

<400> SEQUENCE: 22
gaggtgcagc tggtggagag cggcggcggc gtggtgcagc ccggcggcag cctgagactg      60
agctgcgccg ccagcggctt caccttcagc agattcggca tgcactgggt gagacaggcc     120

```
cccggcaagg gcctggagtg ggtggccttc atcagcaacg agggcagcaa caagtactac    180
gccgacagcg tgaagggcag attcaccatc agcagagaca cagcgccaa cacctgtac     240 ctgcagatga acagcctgag agccgaggac accgccgtgt actactgcgc cagaggcaga   300
gcctacggca gcggcagcct gttcgacccc tggggccagg gcaccctggt gaccgtgagc   360
agc                                                                  363
```

```
<210> SEQ ID NO 23
<211> LENGTH: 121
<212> TYPE: PRT
<213> ORGANISM: Artificial Sequence
<220> FEATURE:
<223> OTHER INFORMATION: Ab612 VH Amino Acid Sequence

<400> SEQUENCE: 23

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Phe Ile Ser Asn Glu Gly Ser Asn Lys Tyr Tyr Ala Asp Ser Val
    50                  55                  60

Lys Gly Arg Phe Thr Ile Ser Arg Asp Asn Ser Ala Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser
        115                 120

<210> SEQ ID NO 24
<211> LENGTH: 108
<212> TYPE: PRT
<213> ORGANISM: Artificial Sequence
<220> FEATURE:
<223> OTHER INFORMATION: Ab612  VL Amino Acid Sequence

<400> SEQUENCE: 24

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Gly Arg Gly Pro
                85                  90                  95

Val Thr Phe Gly Gln Gly Thr Lys Leu Glu Ile Lys
            100                 105

<210> SEQ ID NO 25
<211> LENGTH: 121
```

```
<212> TYPE: PRT
<213> ORGANISM: Artificial Sequence
<220> FEATURE:
<223> OTHER INFORMATION: Ab4H5 VH Amino Acid Sequence

<400> SEQUENCE: 25

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Phe Ile Ser Asn Glu Gly Ser Asn Lys Tyr Tyr Ala Asp Ser Val
    50                  55                  60

Lys Gly Arg Phe Thr Ile Ser Arg Asp Asn Ser Ala Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser
        115                 120

<210> SEQ ID NO 26
<211> LENGTH: 108
<212> TYPE: PRT
<213> ORGANISM: Artificial Sequence
<220> FEATURE:
<223> OTHER INFORMATION: Ab4H5 VL Amino Acid Sequence

<400> SEQUENCE: 26

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gly Phe Tyr Thr Pro
                85                  90                  95

Trp Thr Phe Gly Gln Gly Thr Lys Leu Glu Ile Lys
            100                 105

<210> SEQ ID NO 27
<211> LENGTH: 121
<212> TYPE: PRT
<213> ORGANISM: Artificial Sequence
<220> FEATURE:
<223> OTHER INFORMATION: Ab2C2 VH Amino Acid Sequence

<400> SEQUENCE: 27

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
```

```
                35                  40                  45
Ala Phe Ile Ser Asn Glu Gly Ser Asn Lys Tyr Tyr Ala Asp Ser Val
        50                  55                  60
Lys Gly Arg Phe Thr Ile Ser Arg Asp Asn Ser Ala Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Gly Arg Ala Tyr Gly Ser Gly Ser Leu Phe Asp Pro Trp Gly
            100                 105                 110
Gln Gly Thr Leu Val Thr Val Ser Ser
            115                 120
```

<210> SEQ ID NO 28
<211> LENGTH: 108
<212> TYPE: PRT
<213> ORGANISM: Artificial Sequence
<220> FEATURE:
<223> OTHER INFORMATION: Ab2C2 VL Amino Acid Sequence

<400> SEQUENCE: 28

```
Asp Ile Gln Leu Thr Gln Ser Pro Ser Ser Leu Ser Ala Ser Val Gly
 1               5                  10                  15
Asp Arg Val Thr Ile Thr Cys Arg Ala Ser Arg Thr Ile Ser Ser Tyr
                20                  25                  30
Val Asn Trp Tyr Arg Gln Arg Pro Gly Lys Ala Pro Glu Ser Leu Ile
            35                  40                  45
Tyr Ala Ala Ser Asn Leu His Ser Gly Val Pro Ser Arg Phe Ser Gly
        50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Gly Phe Tyr Ser Pro
                85                  90                  95
Trp Thr Phe Gly Gln Gly Thr Lys Leu Glu Ile Lys
            100                 105
```

<210> SEQ ID NO 29
<211> LENGTH: 121
<212> TYPE: PRT
<213> ORGANISM: Artificial Sequence
<220> FEATURE:
<223> OTHER INFORMATION: Ab4H6 VH Amino Acid Sequence

<400> SEQUENCE: 29

```
Glu Val Gln Leu Val Glu Ser Gly Gly Gly Val Val Gln Pro Gly Gly
 1               5                  10                  15
Ser Leu Arg Leu Ser Cys Ala Ala Ser Gly Phe Thr Phe Ser Arg Phe
                20                  25                  30
Gly Met His Trp Val Arg Gln Ala Pro Gly Lys Gly Leu Glu Trp Val
            35                  40                  45
Ala Phe Ile Ser Asn Glu Gly Ser Asn Lys Tyr Tyr Ala Asp Ser Val
        50                  55                  60
Lys Gly Arg Phe Thr Ile Ser Arg Asp Asn Ser Ala Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Gly Arg Ala Tyr Gly Ser Gly Ser Leu Phe Asp Pro Trp Gly
            100                 105                 110
```

```
Gln Gly Thr Leu Val Thr Val Ser Ser
        115                 120

<210> SEQ ID NO 30
<211> LENGTH: 108
<212> TYPE: PRT
<213> ORGANISM: Artificial Sequence
<220> FEATURE:
<223> OTHER INFORMATION: Ab4H6 VL Amino Acid Sequence

<400> SEQUENCE: 30

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu His Phe Tyr Pro
                85                  90                  95

Trp Thr Phe Gly Gln Gly Thr Lys Leu Glu Ile Lys
            100                 105

<210> SEQ ID NO 31
<211> LENGTH: 121
<212> TYPE: PRT
<213> ORGANISM: Artificial Sequence
<220> FEATURE:
<223> OTHER INFORMATION: Ab5D12 VH Amino Acid Sequence

<400> SEQUENCE: 31

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Phe Ile Ser Asn Glu Gly Ser Asn Lys Tyr Tyr Ala Asp Ser Val
    50                  55                  60

Lys Gly Arg Phe Thr Ile Ser Arg Asp Asn Ser Ala Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser
        115                 120

<210> SEQ ID NO 32
<211> LENGTH: 108
<212> TYPE: PRT
<213> ORGANISM: Artificial Sequence
<220> FEATURE:
<223> OTHER INFORMATION: Ab5D12 VL Amino Acid Sequence

<400> SEQUENCE: 32

Asp Ile Gln Leu Thr Gln Ser Pro Ser Ser Leu Ser Ala Ser Val Gly
```

```
1               5                   10                  15
Asp Arg Val Thr Ile Thr Cys Arg Ala Ser Arg Thr Ile Ser Ser Tyr
                20                  25                  30

Val Asn Trp Tyr Arg Gln Arg Pro Gly Lys Ala Pro Glu Ser Leu Ile
            35                  40                  45

Tyr Ala Ala Ser Asn Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Val Trp Tyr Pro
                85                  90                  95

Trp Thr Phe Gly Gln Gly Thr Lys Leu Glu Ile Lys
                100                 105
```

<210> SEQ ID NO 33
<211> LENGTH: 324
<212> TYPE: DNA
<213> ORGANISM: Artificial Sequence
<220> FEATURE:
<223> OTHER INFORMATION: Ab612 Variable Light Chain Polynucleotide
      Sequence

<400> SEQUENCE: 33

```
gacatccagc tgacccagag ccccagcagc ctgagcgcca gcgtgggcga cagagtgacc     60
atcacctgca gagccagcag aaccatcagc agctacgtga actggtacag acagagaccc    120
ggcaaggccc ccgagagcct gatctacgcc gccagcaacc tgcacagcgg cgtgcccagc    180
agatttagcg gcagcggcag cggcaccgac ttcaccctga ccatcagcag cctgcagccc    240
gaggacttcg ccacctacta ctgccagcag agcatcggca gggcccccgt gaccttcggc    300
cagggcacca agctggagat caag                                           324
```

<210> SEQ ID NO 34
<211> LENGTH: 324
<212> TYPE: DNA
<213> ORGANISM: Artificial Sequence
<220> FEATURE:
<223> OTHER INFORMATION: Ab4H5 Variable Light Chain Polynucleotide
      Sequence

<400> SEQUENCE: 34

```
gacatccagc tgacccagag ccccagcagc ctgagcgcca gcgtgggcga cagagtgacc     60
atcacctgca gagccagcag aaccatcagc agctacgtga actggtacag acagagaccc    120
ggcaaggccc ccgagagcct gatctacgcc gccagcaacc tgcacagcgg cgtgcccagc    180
agatttagcg gcagcggcag cggcaccgac ttcaccctga ccatcagcag cctgcagccc    240
gaggacttcg ccacctacta ctgccagcag gccggcttct acacccccctg gaccttcggc   300 cagggcacca agctggagat caag                                           324
```

<210> SEQ ID NO 35
<211> LENGTH: 324
<212> TYPE: DNA
<213> ORGANISM: Artificial Sequence
<220> FEATURE:
<223> OTHER INFORMATION: Ab2C2 Variable Light Chain Polynucleotide
      Sequence

<400> SEQUENCE: 35

```
gacatccagc tgacccagag ccccagcagc ctgagcgcca gcgtgggcga cagagtgacc     60
```

```
atcacctgca gagccagcag aaccatcagc agctacgtga actggtacag acagagaccc    120
ggcaaggccc ccgagagcct gatctacgcc gccagcaacc tgcacagcgg cgtgcccagc    180
agatttagcg gcagcggcag cggcaccgac ttcaccctga ccatcagcag cctgcagccc    240
gaggacttcg ccacctacta ctgccagcag gccggcttct actcccccctg gaccttcggc   300 cagggcacca agctggagat caag                                            324
```

```
<210> SEQ ID NO 36
<211> LENGTH: 324
<212> TYPE: DNA
<213> ORGANISM: Artificial Sequence
<220> FEATURE:
<223> OTHER INFORMATION: Ab4H6 Variable Light Chain Polynucleotide
      Sequence

<400> SEQUENCE: 36
```

```
gacatccagc tgacccagag ccccagcagc ctgagcgcca gcgtgggcga cagagtgacc     60
atcacctgca gagccagcag aaccatcagc agctacgtga actggtacag acagagaccc    120
ggcaaggccc ccgagagcct gatctacgcc gccagcaacc tgcacagcgg cgtgcccagc    180
agatttagcg gcagcggcag cggcaccgac ttcaccctga ccatcagcag cctgcagccc    240
gaggacttcg ccacctacta ctgccagcag tccctgcact ctacccctg gaccttcggc     300 cagggcacca agctggagat caag                                            324
```

```
<210> SEQ ID NO 37
<211> LENGTH: 324
<212> TYPE: DNA
<213> ORGANISM: Artificial Sequence
<220> FEATURE:
<223> OTHER INFORMATION: Ab5D12 Variable Light Chain Polynucleotide
      Sequence

<400> SEQUENCE: 37
```

```
gacatccagc tgacccagag ccccagcagc ctgagcgcca gcgtgggcga cagagtgacc     60
atcacctgca gagccagcag aaccatcagc agctacgtga actggtacag acagagaccc    120
ggcaaggccc ccgagagcct gatctacgcc gccagcaacc tgcacagcgg cgtgcccagc    180
agatttagcg gcagcggcag cggcaccgac ttcaccctga ccatcagcag cctgcagccc    240
gaggacttcg ccacctacta ctgccagcag tccctggtgt ggtacccctg gaccttcggc    300
cagggcacca agctggagat caag                                            324
```

```
<210> SEQ ID NO 38
<211> LENGTH: 451
<212> TYPE: PRT
<213> ORGANISM: Artificial Sequence
<220> FEATURE:
<223> OTHER INFORMATION: Ab612 Heavy Chain Amino Acid Sequence

<400> SEQUENCE: 38
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Phe Ile Ser Asn Glu Gly Ser Asn Lys Tyr Tyr Ala Asp Ser Val
    50                  55                  60

Lys Gly Arg Phe Thr Ile Ser Arg Asp Asn Ser Ala Asn Thr Leu Tyr

```
            65                  70                  75                  80
Leu Gln Met Asn Ser Leu Arg Ala Glu Asp Thr Ala Val Tyr Tyr Cys
                    85                  90                  95

Ala Arg Gly Arg Ala Tyr Gly Ser Gly Ser Leu Phe Asp Pro Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
        450

<210> SEQ ID NO 39
<211> LENGTH: 215
<212> TYPE: PRT
<213> ORGANISM: Artificial Sequence
```

<220> FEATURE:
<223> OTHER INFORMATION: Ab612 Light Chain Amino Acid Sequence

<400> SEQUENCE: 39

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Gly Arg Gly Pro
                85                  90                  95

Val Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 40
<211> LENGTH: 451
<212> TYPE: PRT
<213> ORGANISM: Artificial Sequence
<220> FEATURE:
<223> OTHER INFORMATION: Ab4H5 Heavy Chain Amino Acid Sequence

<400> SEQUENCE: 40

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Phe Ile Ser Asn Glu Gly Ser Asn Lys Tyr Tyr Ala Asp Ser Val
    50                  55                  60

Lys Gly Arg Phe Thr Ile Ser Arg Asp Asn Ser Ala Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser Ala Ser Thr Lys Gly Pro Ser 115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 41
<211> LENGTH: 214
<212> TYPE: PRT
<213> ORGANISM: Artificial Sequence
<220> FEATURE:
<223> OTHER INFORMATION: Ab4H5 Light Chain Amino Acid Sequence

<400> SEQUENCE: 41

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr

```
                 20                  25                  30
Val Asn Trp Tyr Arg Gln Arg Pro Gly Lys Ala Pro Glu Ser Leu Ile
             35                  40                  45
Tyr Ala Ala Ser Asn Leu His Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ala Gly Phe Tyr Thr Pro
                 85                  90                  95
Trp Thr Phe Gly Gln Gly Thr Lys Leu Glu Ile Lys Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 42
<211> LENGTH: 451
<212> TYPE: PRT
<213> ORGANISM: Artificial Sequence
<220> FEATURE:
<223> OTHER INFORMATION: Ab2C2 Heavy Chain Amino Acid Sequence

<400> SEQUENCE: 42

Glu Val Gln Leu Val Glu Ser Gly Gly Gly Val Val Gln Pro Gly Gly
 1               5                  10                  15
Ser Leu Arg Leu Ser Cys Ala Ala Ser Gly Phe Thr Phe Ser Arg Phe
             20                  25                  30
Gly Met His Trp Val Arg Gln Ala Pro Gly Lys Gly Leu Glu Trp Val
         35                  40                  45
Ala Phe Ile Ser Asn Glu Gly Ser Asn Lys Tyr Tyr Ala Asp Ser Val
     50                  55                  60
Lys Gly Arg Phe Thr Ile Ser Arg Asp Asn Ser Ala Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Arg Ala Tyr Gly Ser Gly Ser Leu Phe Asp Pro Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
```

```
                    165                 170                 175
Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 43
<211> LENGTH: 215
<212> TYPE: PRT
<213> ORGANISM: Artificial Sequence
<220> FEATURE:
<223> OTHER INFORMATION: Ab2C2 Light Chain Amino Acid Sequence

<400> SEQUENCE: 43

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr
            20                  25                  30

Val Asn Trp Tyr Arg Gln Arg Pro Gly Lys Ala Pro Glu Ser Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
```

```
             65                  70                  75                  80
Glu Asp Phe Ala Thr Tyr Tyr Cys Gln Gln Ala Gly Phe Tyr Ser Pro
                    85                  90                  95

Trp Thr Phe Gly Gln Gly Thr Lys Leu Glu Ile Lys Arg Thr Val Ala
                100                 105                 110

Ala Pro Ser Val Phe Ile Phe Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
            210                 215

<210> SEQ ID NO 44
<211> LENGTH: 451
<212> TYPE: PRT
<213> ORGANISM: Artificial Sequence
<220> FEATURE:
<223> OTHER INFORMATION: Ab4H6 Heavy Chain Amino Acid Sequence

<400> SEQUENCE: 44

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
                20                  25                  30

Gly Met His Trp Val Arg Gln Ala Pro Gly Lys Gly Leu Glu Trp Val
            35                  40                  45

Ala Phe Ile Ser Asn Glu Gly Ser Asn Lys Tyr Tyr Ala Asp Ser Val
50                  55                  60

Lys Gly Arg Phe Thr Ile Ser Arg Asp Asn Ser Ala Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Tyr Gly Ser Gly Ser Leu Phe Asp Pro Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
```

```
                210                 215                 220
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 45
<211> LENGTH: 215
<212> TYPE: PRT
<213> ORGANISM: Artificial Sequence
<220> FEATURE:
<223> OTHER INFORMATION: Ab4H6 Light Chain Amino Acid Sequence

<400> SEQUENCE: 45

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Thr Ile Ser Ser Tyr
                20                  25                  30

Val Asn Trp Tyr Arg Gln Arg Pro Gly Lys Ala Pro Glu Ser Leu Ile
                35                  40                  45

Tyr Ala Ala Ser Asn Leu His Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu His Phe Tyr Pro
                85                  90                  95

Trp Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
```

```
            115                 120                 125
Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 46
<211> LENGTH: 451
<212> TYPE: PRT
<213> ORGANISM: Artificial Sequence
<220> FEATURE:
<223> OTHER INFORMATION: Ab5D12 Heavy Chain Amino Acid Sequence

<400> SEQUENCE: 46

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Arg Phe
            20                  25                  30

Gly Met His Trp Val Arg Gln Ala Pro Gly Lys Gly Leu Glu Trp Val
        35                  40                  45

Ala Phe Ile Ser Asn Glu Gly Ser Asn Lys Tyr Tyr Ala Asp Ser Val
    50                  55                  60

Lys Gly Arg Phe Thr Ile Ser Arg Asp Asn Ser Ala Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Tyr Gly Ser Gly Ser Leu Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
```

-continued

```
                260                 265                 270
Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450
```

ANTI-L1CAM ANTIBODIES AND USES THEREOF

CROSS-REFERENCE TO RELATED APPLICATIONS

This application is the United States National Phase of International Application No. PCT/132019/055472, filed on Jun. 27, 2019, which claims priority to U.S. Provisional Application No. 62/865,871, filed Jun. 24, 2019 and Korean Application No. 10-2018-0075955, filed Jun. 29, 2018, each of which is herein incorporated by reference in its entirety.

REFERENCE TO SEQUENCE LISTING SUBMITTED ELECTRONICALLY

The content of the electronically submitted sequence listing in ASCII text file (Name: 4372_0010002_Seqlisting_ST25.txt; Size: 82,883 bytes; and Date of Creation: Jun. 21, 2021) filed with the application is incorporated herein by reference in its entirety.

FIELD OF THE DISCLOSURE

The present disclosure provides antibodies that specifically bind to L1 Cell Adhesion Molecule (L1CAM), compositions comprising such antibodies, and method of using such antibodies for preventing or treating diseases or conditions which comprise a tumor (e.g., a bile duct cancer, a melanoma, pancreatic cancer, glioma, breast cancer, lymphoma, lung cancer, kidney cancer, prostate cancer, fibrosarcoma, colon adenocarcinoma, liver cancer, and/or ovarian cancer) in a subject.

BACKGROUND OF THE DISCLOSURE

L1 Cell Adhesion Molecule (L1CAM) is one of the immunoglobulin superfamily cell adhesion molecules (CAMs) that mediates cell-to-cell adhesion on the cell surface. It has a molecular weight of 200 to 220 kDa. L1CAM was first known as a protein that mediates neuron-neuron adhesion and is involved in neurite outgrowth and neuronal migration. Lee V. et al., Proc. Natl. Acad. Sci. 74:5021-5025 (1997); McGuire J C. et al., Cell. 15(2):357-365 (1978).

L1CAM is predominantly expressed in the normal human brain. In addition, L1CAM expression is found in some hematopoietic and renal cells, peripheral nerves, intestinal crypt cells, and ganglions, but it is not found in other normal cells. Huszar M. et al., Human Pathology 37:1000-1008 (2006).

An antibody that specifically binds to L1CAM protein may be used for the diagnosis and prevention or treatment of diseases in which L1CAM is overexpressed (e.g., cancer). Accordingly, there is a need to develop antibodies that specifically bind to L1CAM and that are capable of modulating L1CAM activity.

BRIEF SUMMARY OF THE DISCLOSURE

One aspect of the present disclosure is directed to an isolated antibody or antigen-binding fragment thereof that specifically binds to the same L1 Cell Adhesion Molecule (L1CAM) epitope as a reference antibody comprising a heavy chain variable region (VH) and a light chain variable region (VL), wherein: (a) the VH of the reference antibody comprises SEQ ID NO: 23 and the VL of the reference antibody comprises SEQ ID NO: 24, (b) the VH of the reference antibody comprises SEQ ID NO: 25 and the VL of the reference antibody comprises SEQ ID NO: 26, (c) the VH of the reference antibody comprises SEQ ID NO: 27 and the VL of the reference antibody comprises SEQ ID NO: 28, (d) the VH of the reference antibody comprises SEQ ID NO: 29 and the VL of the reference antibody comprises SEQ ID NO: 30, or (e) the VH of the reference antibody comprises SEQ ID NO: 31 and the VL of the reference antibody comprises SEQ ID NO: 32.

Also provided herein is the anti-L1CAM antibody or antigen-binding fragment thereof, wherein the antibody or antigen-binding fragment thereof comprises VH complementarity determining region 1(CDR1), VH CDR2, and VH CDR3, and VL CDR1, VL CDR2, and VL CDR3, wherein at least one amino acid in the VH CDR1, VH CDR2, VH CDR3, VL CDR1, VL CDR2, and/or VL CDR3 of the antibody or antigen-binding fragment thereof is different from the VH CDR1, VH CDR2, VH CDR3, VL CDR1, VL CDR2, and/or VL CDR3 of the mAb417 antibody, and wherein the VH CDR1 of the mAb417 antibody comprises RFGMH (SEQ ID NO: 2); the VH CDR2 of the mAb417 antibody comprises FISNDGSNKYYADSVKG (SEQ ID NO: 9); the VH CDR3 of the mAb417 antibody comprises GRAYGSGSLFDP (SEQ ID NO: 4); the VL CDR1 of the mAb417 antibody comprises RASRTISIYVN (SEQ ID NO: 6); the VL CDR2 of the mAb417 antibody comprises AASNLHS (SEQ ID NO: 7); and the VL CDR3 of the mAb417 antibody comprises QQSIGRGVVT (SEQ ID NO: 11).

The present disclosure further provides the isolated antibody or antigen-binding fragment thereof that cross-competes for binding to L1CAM epitope with a reference antibody comprising a heavy chain variable region (VH) and a light chain variable region (VL), wherein: (a) the VH of the reference antibody comprises SEQ ID NO: 23 and the VL of the reference antibody comprises SEQ ID NO: 24, (b) the VH of the reference antibody comprises SEQ ID NO: 25 and the VL of the reference antibody comprises SEQ ID NO: 26, (c) the VH of the reference antibody comprises SEQ ID NO: 27 and the VL of the reference antibody comprises SEQ ID NO: 28, (d) the VH of the reference antibody comprises SEQ ID NO: 29 and the VL of the reference antibody comprises SEQ ID NO: 30, or (e) the VH of the reference antibody comprises SEQ ID NO: 31 and the VL of the reference antibody comprises SEQ ID NO: 32, wherein the antibody or antigen-binding fragment thereof comprises VH complementarity determining region 1(CDR1), VH CDR2, and VH CDR3, and VL CDR1, VL CDR2, and VL CDR3, wherein at least one amino acid in the VH CDR1, VH CDR2, VH CDR3, VL CDR1, VL CDR2, and/or VL CDR3 of the antibody or antigen-binding fragment thereof is different from the VH CDR1, VH CDR2, VH CDR3, VL CDR1, VL CDR2, and/or VL CDR3 of the mAb 417 antibody, and wherein the VH CDR1 of the mAb417 antibody comprises RFGMH (SEQ ID NO: 2); the VH CDR2 of the mAb417 antibody comprises FISNDGSNKYYADSVKG (SEQ ID NO: 9); the VH CDR3 of the mAb417 antibody comprises GRAYGSGSLFDP (SEQ ID NO: 4); the VL CDR1 of the mAb417 antibody comprises RASRTISIYVN (SEQ ID NO: 6); the VL CDR2 of the mAb417 antibody comprises AASNLHS (SEQ ID NO: 7); and the VH CDR3 of the mAb417 antibody comprises QQSIGRGVVT (SEQ ID NO: 11).

In certain aspects, the at least one amino acid difference comprises (i) glutamine at residue 5 in the VH CDR2; (ii) serine at residue 8 in the VL CDR1; and/or (iii) proline at residue 8 in the VL CDR3 of the anti-L1CAM antibody or antigen-binding fragment thereof. In certain aspects, the at least one amino acid difference comprises (i) alanine, glycine, phenylalanine, tyrosine, threonine, proline, and tryptophan at residues 3 to 9, respectively in the VL CDR3; (ii) alanine, glycine, phenylalanine, tyrosine, serine, proline, and tryptophan at residues 3 to 9, respectively in the VL CDR3 or (iii) leucine, valine or histidine, tryptophan or phenylalanine, tyrosine, proline, and tryptophan at residues 4 to 9, respectively in the VL CDR3 of the anti-L1CAM antibody or antigen-binding fragment thereof. In some aspects, the anti-L1CAM antibody or antigen-binding fragment thereof disclosed herein comprises the VL CDR3 of the antibody or antigen-binding fragment thereof comprises SEQ ID NO: 13, SEQ ID NO: 15, SEQ ID NO: 17, SEQ ID NO: 19, or SEQ ID NO: 21. In some aspects, the VH CDR1 of the anti-L1CAM antibody comprises RFGMH (SEQ ID NO: 2). In some aspects, the VH CDR2 of the anti-L1CAM antibody comprises FISNEGSNKYYADSVKG (SEQ ID NO: 10). In some aspects, the VH CDR3 of the anti-L1CAM antibody comprises GRAYGSGSLFDP (SEQ ID NO: 4).

In some aspects, the VL CDR1 of the anti-L1CAM antibody comprises RASRTISSYVN (SEQ ID NO: 12). In some aspects, the VL CDR2 of the anti-L1CAM antibody comprises AASNLHS (SEQ ID NO: 7). In some aspects, the VL CDR3 of the anti-L1CAM antibody comprises QQSIGRGPVT (SEQ ID NO: 13).

In some aspects, the anti-L1CAM antibody or antigen-binding fragment thereof of the present disclosure comprises a heavy chain CDR1, CDR2, and CDR3 and a light chain CDR1, CDR2, and CDR3, wherein the light chain CDR3 comprises QQSIGRGPVT (SEQ ID NO:13), QQAGFYTPWT (SEQ ID NO:15), QQAGFYSPWT (SEQ ID NO:17), QQSLHFYPWT (SEQ ID NO:19), or QQSLVWYPWT (SEQ ID NO:21).

The present disclosure further provides the anti-L1CAM antibody or antigen-binding fragment thereof disclosed herein which has one or more characteristics selected from the group consisting of: (a) exhibits improved productivity compared to the mAb417 antibody; (b) exhibits improved affinity as measured by the equilibrium dissociation constant ($K_D$) compared to the mAb417 antibody; (c) exhibits improved PI value compared to the mAb417 antibody; (d) exhibits improved affinity as measured by the association constant (K) compared to the mAb417 antibody; or (e) any combination thereof.

In some aspects, the anti-L1CAM antibody or antigen-binding fragment thereof disclosed herein exhibits improved productivity compared to the mAb417 antibody, wherein the improved productivity is at least 55 mg/L, at least 56 mg/L, at least 57 mg/L, at least 58 mg/L, at least 59 mg/L, at least about 60 mg/L, at least about 61 mg/L, at least about 62 mg/L, at least about 63 mg/L, at least about 64 mg/L, at least about 65 mg/L, at least about 66 mg/L, at least about 67 mg/L, at least about 68 mg/L, at least about 69 mg/L, at least about 70 mg/L, at least about 71 mg/L, at least about 72 mg/L, at least about 73 mg/L, at least about 74 mg/L, at least about 75 mg/L, at least about 76 mg/L, at least about 77 mg/L, at least about 78 mg/L, at least about 79 mg/L, at least about 80 mg/L, at least about 81 mg/L, at least about 82 mg/L, at least about 83 mg/L, at least about 84 mg/L, or at least about 85 mg/L, when expressed according to example 3.

In some aspects, the anti-L1CAM antibody or antigen-binding fragment thereof disclosed herein exhibits improved affinity as measured by the equilibrium dissociation constant ($K_D$) compared to the mAb417 antibody, wherein the improved $K_D$ is less than $2.6 \times 10^{-10}$ M, less than $2.5 \times 10^{-10}$ M, less than $2.0 \times 10^{-10}$ M, less than $1.5 \times 10^{-10}$ M, less than $1.0 \times 10^{-10}$ M, less than $9 \times 10^{-11}$ M, less than $8 \times 10^{-11}$ M, less than $7 \times 10^{-11}$ M, less than $6 \times 10^{-11}$ M, less than $5 \times 10^{-11}$ M, less than $4 \times 10^{-11}$ M, less than $3 \times 10^{-11}$ M, less than $2 \times 10^{-11}$ M, less than $1 \times 10^{-11}$ M, less than $9 \times 10^{-12}$ M, less than $8 \times 10^{-12}$ M, less than $7 \times 10^{-12}$ M, less than $6 \times 10^{-12}$ M, less than $5 \times 10^{-12}$ M, less than $4 \times 10^{-12}$ M, less than $3 \times 10^{-12}$ M, less than $2 \times 10^{-12}$ M, less than $1 \times 10^{-12}$ M, less than $9 \times 10^{-13}$ M, or less than $8 \times 10^{-13}$ M.

In other aspects, the anti-L1CAM antibody or antigen-binding fragment thereof disclosed herein exhibits improved affinity as measured by the association constant (K) compared to the mAb417 antibody, wherein the improved K is less than $5 \times 10^{-10}$ M, less than $4 \times 10^{-10}$ M, less than $3 \times 10^{-10}$ M, less than $2 \times 10^{-10}$ M, less than $1.0 \times 10^{-10}$ M, less than $9 \times 10^{-11}$ M, less than $8 \times 10^{-11}$ M, less than $7 \times 10^{-11}$ M, less than $6 \times 10^{-11}$ M, less than $5 \times 10^{-11}$ M, less than $4 \times 10^{-11}$ M, less than $3 \times 10^{-11}$ M, less than $2 \times 10^{-11}$ M, less than $1 \times 10^{-11}$ M, less than $9 \times 10^{-12}$ M, less than $8 \times 10^{-12}$ M, less than $7 \times 10^{-12}$ M, less than $6 \times 10^{-12}$ M, less than $5 \times 10^{-12}$ M, less than $4 \times 10^{-12}$ M, less than $3 \times 10^{-12}$ M, less than $2 \times 10^{-12}$ M, less than $1 \times 10$ 12 M, less than $9 \times 10^{-13}$ M, or less than $8 \times 10^{-13}$ Min some aspects, the anti-L1CAM antibody or antigen-binding fragment thereof disclosed herein exhibits improved PI value compared to the mAb417 antibody, wherein the improved PI Value is less than 9.6, less than 9.5, less than 9.4, less than 9.3, less than 9.2, less than 9.1, less than 9.0, less than 8.9, less than 8.8, less than 8.7, less than 8.6, less than 8.5, less than 8.4, less than 8.3, less than 8.2, less than 8.1, less than 8.0, less than 7.9, less than 7.8, less than 7.7, or less than 7.6.

In some aspects, the anti-L1CAM antibody or antigen-binding fragment thereof disclosed herein comprises a VH CDR1, CDR2, and CDR3 and a VL CDR1, CDR2, and CDR3; wherein the VH CDR1, CDR2, and CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, CDR2, and CDR3 comprises RASRTISSYVN (SEQ ID NO: 12), AASNLHS (SEQ ID NO: 7), and QQSIGRGPVT (SEQ ID NO: 13), respectively.

In some aspects, the anti-L1CAM antibody or antigen-binding fragment thereof disclosed herein comprises a VH CDR1, CDR2, CDR3 and a VL CDR1, CDR2, CDR3; wherein the VH CDR1, CDR2, and CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, CDR2, and CDR3 comprises RASRTISSYVN (SEQ ID NO: 12), AASNLHS (SEQ ID NO: 7), and QQAGFYSPWT (SEQ ID NO: 17), respectively.

In some aspects, the anti-L1CAM antibody or antigen-binding fragment thereof disclosed herein comprises a VH CDR1, CDR2, CDR3 and a VL CDR1, CDR2, CDR3; wherein the VH CDR1, CDR2, and CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, CDR2, and CDR3 comprises RASRTISSYVN (SEQ ID NO: 12), AASNLHS (SEQ ID NO: 7), and QQAGFYTPWT (SEQ ID NO: 15), respectively.

In some aspects, the anti-L1CAM antibody or antigen-binding fragment thereof disclosed herein comprises a VH CDR1, CDR2, CDR3 and a VL CDR1, CDR2, CDR3; wherein the VH CDR1, CDR2, and CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, CDR2, and CDR3 comprises RASRTISSYVN (SEQ ID NO: 12), AASNLHS (SEQ ID NO: 7), and QQSLHFYPWT (SEQ ID NO: 19), respectively.

In some aspects, the anti-L1CAM antibody or antigen-binding fragment thereof disclosed herein comprises a VH CDR1, CDR2, CDR3 and a VL CDR1, CDR2, CDR3; wherein the VH CDR1, CDR2, and CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, CDR2, and CDR3 comprises RASRTISSYVN (SEQ ID NO: 12), AASNLHS (SEQ ID NO: 7), and QQSLVWYPWT (SEQ ID NO: 21), respectively.

In some aspects, the VH of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO: 23).

In other aspects, the VL of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DIQL TQSPSS LSASVGDRVT ITCRASRTIS SYVNWYRQRP GKAPESLIYA ASNLHSGVPS RFSGSGSGTD FTLTISSLQP EDFA-TYYCQQ SIGRGPVTFG QGTKLEIK (SEQ ID NO: 24).

In some aspects, the VH of the anti-L1CAM antibody antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO: 27).

In other aspects, the VL of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DIQL TQSPSS LSASVGDRVT ITCRASRTIS SYVNWYRQRP GKAPESLIYA ASNLHSGVPS RFSGSGSGTD FTLTISSLQP EDFA-TYYCQQ AGFYSPWTFG QGTKLEIK (SEQ ID NO: 28).

In some aspects, the VH of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO: 25).

In some aspects, the VL of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DIQL TQSPSS LSASVGDRVT ITCRASRTIS SYVNWYRQRP GKAPESLIYA ASNLHSGVPS RFSGSGSGTD FTLTISSLQP EDFA-TYYCQQ AGFYTPWTFG QGTKLEIK (SEQ ID NO: 26).

In other aspects, the VH of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGG VVQPGGSLRL SCAASGFTFS RFGMHWVRQA PGKGLEWVAF ISNEGSNKYY ADSVKGRFTI SRDNSANTLY LQMNSLRAED TAVYYCARGR AYGSGSLFDP WGQGTLVTVS S (SEQ ID NO: 29).

In some aspects, the VL of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DIQL TQSPSS LSASVGDRVT ITCRASRTIS SYVNWYRQRP GKAPESLIYA ASNLHSGVPS RFSGSGSGTD FTLTISSLQP EDFA-TYYC QQSLHFYPWT FG QGTKLEIK (SEQ ID NO: 30).

In other aspects, the VH of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO: 31).

In some aspects, the VL of the anti-L1CAM antibody or antigen-binding fragment thereof disclosed herein comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DIQLTQSPSS LSASVGDRVT ITCRASRTIS SYVNWYRQRP GKAPESLIYA ASNLHSGVPS RFSGSGSGTD FTLTISSLQP EDFA-TYYC QQSLVWYPWT FG QGTKLEIK (SEQ ID NO: 32).

In some aspects, the VH of the anti-L1CAM antibody or antigen-binding fragment thereof disclosed herein comprises SEQ ID NO: 23 and the VL of the anti-L1CAM antibody or antigen-binding fragment thereof comprises SEQ ID NO: 24. In other aspects, the VH of the anti-L1CAM antibody or antigen-binding fragment thereof comprises SEQ ID NO: 25 and the VL of the anti-L1CAM antibody or antigen-binding fragment thereof comprises SEQ ID NO: 26. In some aspects, the VH of the anti-L1CAM antibody or antigen-binding fragment thereof comprises SEQ ID NO: 27 and the VL of the anti-L1CAM antibody or antigen-binding fragment thereof comprises SEQ ID NO: 28. In other aspects, the VH of the anti-L1CAM antibody or antigen-binding fragment thereof comprises SEQ ID NO: 29 and the VL of the anti-L1CAM antibody or antigen-binding fragment thereof comprises SEQ ID NO: 30. In some aspects, the VH of the anti-L1CAM antibody or antigen-binding fragment thereof comprises SEQ ID NO: 29 and the VL of the anti-L1CAM antibody or antigen-binding fragment thereof comprises SEQ ID NO: 30. In other aspects, the VH of the anti-L1CAM antibody or antigen-binding fragment thereof comprises SEQ ID NO: 31 and the VL of the anti-L1CAM antibody or antigen-binding fragment thereof comprises SEQ ID NO: 32.

Also provided herein is the anti-L1CAM antibody or antigen-binding fragment thereof disclosed herein, which comprises a heavy chain (HC) and a light chain (LC), wherein the HC of the antibody or antigen-binding fragment thereof comprises SEQ ID NO: 38 and the LC of the antibody or antigen-binding fragment thereof comprises SEQ ID NO: 39. In some aspects, the HC of the antibody or antigen-binding fragment thereof comprises SEQ ID NO: 40 and the LC of the antibody or antigen-binding fragment thereof comprises SEQ ID NO: 41. In some aspects, the HC of the antibody or antigen-binding fragment thereof comprises SEQ ID NO: 42 and the LC of the antibody or antigen-binding fragment thereof comprises SEQ ID NO: 43. In some aspects, the HC of the antibody or antigen-binding fragment thereof comprises SEQ ID NO: 44 and the LC of the antibody or antigen-binding fragment thereof comprises SEQ ID NO: 45. In some aspects, the HC of the antibody or antigen-binding fragment thereof comprises SEQ ID NO: 46 and the LC of the antibody or antigen-binding fragment thereof comprises SEQ ID NO: 20.

In some aspects, wherein the anti-L1CAM antibody is selected from the group consisting of an IgG1, IgG2, IgG3, IgG4, a variant thereof, and any combination thereof. In some aspects, the anti-L1CAM antibody is a chimeric antibody, or a human antibody. In some aspects, the anti-L1CAM antibody comprises a Fab, a Fab', a F(ab')2, a Fv, or a single chain Fv (scFv).

Some aspects of the present disclosure are directed to a nucleic acid encoding the anti-L1CAM antibody, a vector comprising the nucleic acid, a host cell comprising the vector. In some aspects, the host cell is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

Some aspects of the present disclosure are directed to an immunoconjugate comprising the anti-L1CAM antibody or antigen-binding fragment thereof disclosed herein linked to an agent.

Also provided herein is a bispecific or multispecific antibody comprising the anti-L1CAM antibody or antigen-binding fragment and an antibody or antigen-binding fragment thereof that binds to an antigen.

Some aspects of the present disclosure are directed to a composition comprising the anti-L1CAM antibody, the nucleic acid, the vector, the host cell, the immunoconjugate, or the bispecific or multispecific antibody disclosed herein, and a carrier.

Also provided herein is a kit comprising the anti-L1CAM antibody disclosed herein, and an instruction for use.

Some aspects of the present disclosure are directed to a method of producing an antibody which specifically binds to a human L1CAM protein, comprising culturing the host cell under suitable conditions and isolating the antibody.

Also provided herein is a method of treating a disease or condition in a subject in need thereof, comprising administering to the subject the anti-L1CAM antibody the nucleic acid, the vector, the host cell, the immunoconjugate, or the bispecific or multispecific antibody disclosed herein. In some aspects, the disease or condition comprises a tumor. In some aspects, the tumor comprises a bile duct cancer, a melanoma, pancreatic cancer, glioma, breast cancer, lymphoma, lung cancer, kidney cancer, prostate cancer, fibrosarcoma, colon adenocarcinoma, liver cancer, or ovarian cancer. In other aspect, the anti-L1CAM antibody, the nucleic acid, the vector, the cell, the immunoconjugate, the bispecific or multispecific antibody suppresses growth of the tumor and/or enhances infiltration of immune cells into the tumor.

Some aspects of the present disclosure are directed to the method which comprises administering an additional therapeutic agent. In some aspects, the additional therapeutic agent comprises a chemotherapy, immunotherapy, radiotherapy, or combinations thereof. In some aspects, the additional therapeutic agent is an immune checkpoint inhibitor.

Other features and advantages of the instant disclosure will be apparent from the following detailed description and examples which should not be construed as limiting. The contents of all cited references, including scientific articles, newspaper reports, GenBank entries, patents and patent applications cited throughout this application are expressly incorporated herein by reference.

BRIEF DESCRIPTION OF THE DRAWINGS

FIGS. 1A-1D show analysis of antigen-binding specificity of Ab417 variants to human LCAM1 in CHO-DG44 cells (FIG. 1A), NCI-H522 (FIG. 1B), SKOV3 (FIG. 1C), and B16F1 (FIG. 1D) using flow cytometry.

FIG. 2A-2F show quality of purified Ab417 (FIG. 2A) and Ab417 variants: Ab612 (FIG. 2B), Ab4H5 (FIG. 2C), Ab2C2 (FIG. 2D), Ab4H6 (FIG. 2E), and Ab5D12 (FIG. 2F) measured by size exclusion-high-performance liquid chromatography (SEC-HPLC).

FIGS. 3A-3D show analysis of tumor growth-inhibitory effect of Ab417 variants. FIG. 3A shows changes in the tumor volume of Choi-CK xenograft model after administration of Ab417 (10 mg/kg), Ab612 (10 mg/kg), control hFc (human Fc) antibody (3.3) mg/kg, and negative control (PBS) (*p<0.05, Significant difference from the isotype control group by Dunnett's t-test). FIG. 3B shows changes in the body weights of Choi-CK xenograft model after administration of Ab417, Ab612, control hFc, and negative control (PBS). FIG. 3C shows the tumor weights of Choi-CK xenograft model after administration of Ab417 (10 mg/kg), Ab612 (10 mg/kg), Ab612 (10 mg/kg), control hFc antibody (3.3) mg/kg, and negative control (vehicle). (*p<0.01, Significant difference from the isotype control group by Dunnett's t-test). FIG. 3D shows the tumor images of each group of eight mice sacrificed after the end of the experiment as described in FIG. 3C.

DETAILED DESCRIPTION OF THE DISCLOSURE

Figure 3A:
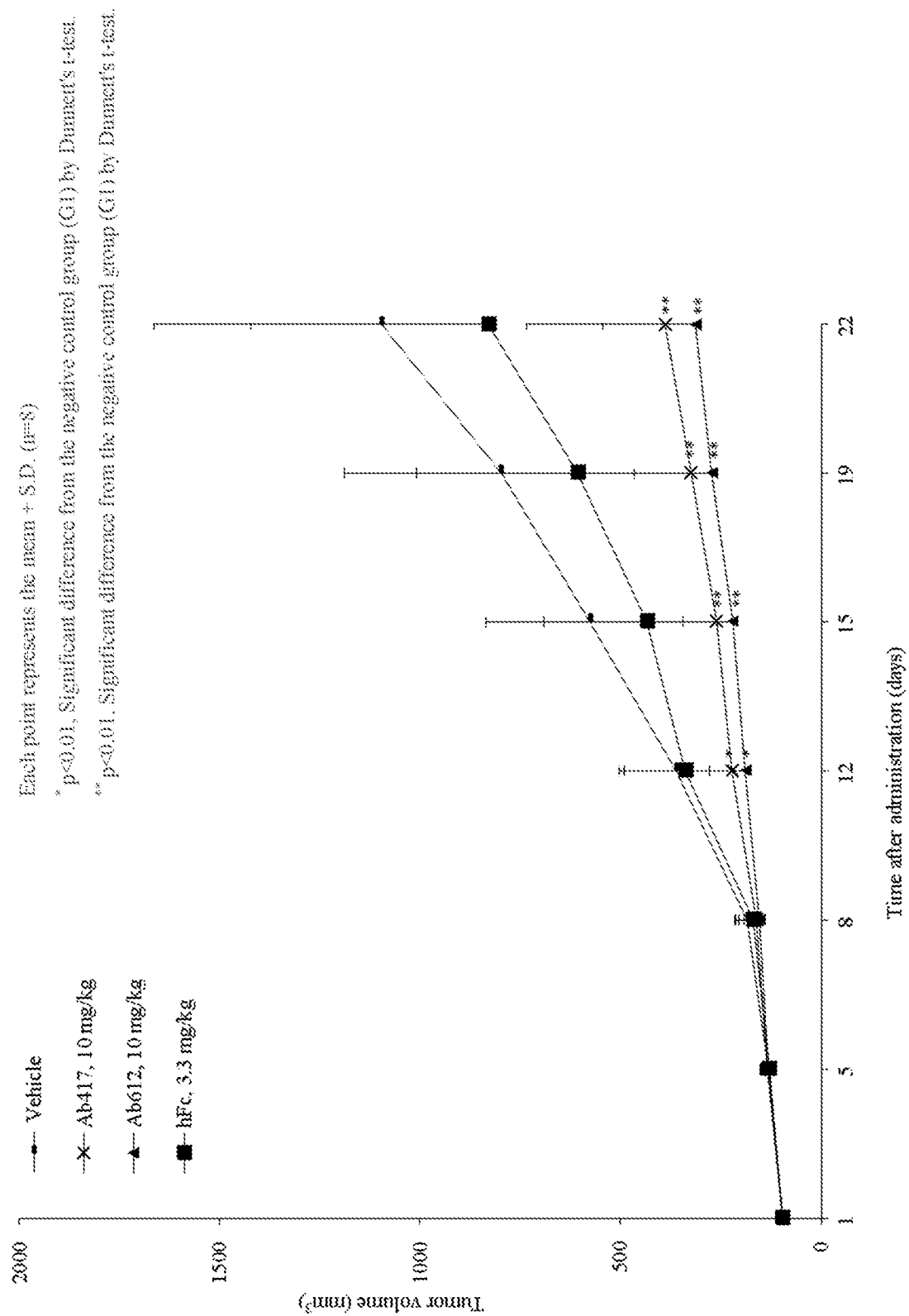

Disclosed herein is an isolated antibody or antigen-binding fragment thereof that specifically binds to the same L1 Cell Adhesion Molecule (L1CAM) epitope as a reference antibody; cross-competes for binding to an L1CAM epitope with a reference antibody and exhibits one or more of the properties disclosed herein; and/or prevents and/or treats diseases or conditions which comprise a tumor.

To facilitate an understanding of the disclosure disclosed herein, a number of terms and phrases are defined. Additional definitions are set forth throughout the detailed description.

I. Definitions

Throughout this disclosure, the term "a" or "an" entity refers to one or more of that entity; for example, "an antibody," is understood to represent one or more antibodies. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "L1 cell adhesion molecule" or "L1CAM" refers to one of integral membrane glycoproteins belonging to the immunoglobulin superfamily cell adhesion molecules (CAMs).

The term "L1CAM" includes any variants or isoforms of L1CAM which are naturally expressed by cells. Accordingly, antibodies described herein can cross-react with different isoforms in the same species (e.g., different isoforms of human L1CAM), or cross-react with L1CAM from species other than human (e.g., mouse L1CAM). Alternatively, the antibodies can be specific for human L1CAM and cannot exhibit any cross-reactivity with other species. L1CAM, or any variants and isoforms thereof, can either be isolated from cells or tissues which naturally express them or be recombinantly produced using well-known techniques in the art and/or those described herein.

Human L1CAM (UniProt ID No. P32004-1; SEQ ID NO: 1) is a type 1 integral membrane glycoprotein which is composed of 1,257 amino acids and spans the cell membrane once, and its amino terminal fragment exists outside the cell membrane and its carboxyl terminal fragment exists in the cytoplasm. The extracellular domain of L1CAM includes 11 domains of six immunoglobulin type 2 domains, (Ig1, Ig2, Ig3, Ig4, Ig5, and Ig6) five fibronectin III-like domains (Fn1, Fn2, Fn3, Fn4, and Fn5), and twenty N-glycosylation sites. U.S. Pat. No. 9,777,060.

At least two additional isoforms of human L1CAM have been identified. Isoform 2, (UniProt ID No. P32004-2; SEQ ID NO: 3) consists of 1,253 amino acids. Isofrom 2 lacks amino acid residues 1177-1180 relative to the amino acid sequence of human L1CAM. Isoform 3, (UniProt ID No. P32004-3; SEQ ID NO: 5) consists of 1,248 amino acids. Isofrom 3 lacks amino acid residues 1177-1180 and has the following difference at amino acid residues 26-31 (YEGHHV→L) relative to the amino acid sequence of human L1CAM.

Below are the amino acid sequences of the three known human L1CAM isoforms.

(A) Human L1CAM (UniProt ID No. P32004-1; SEQ ID NO: 1)

MVVALRYVWPLLLCSPCLLIQIPEEYEGHHVMEPPVITEQSPRRLVVFP

TDDISLKCEASGKPEVQFRWTRDGVHFKPKEELGVTVYQSPHSGSFTIT

GNNSNFAQRFQGIYRCFASNKLGTAMSHEIRLMAEGAPKWPKETVKPVE

VEEGESVVLPCNPPPSAEPLRIYWMNSKILHIKQDERVTMGQNGNLYFA

NVLTSDNHSDYICHAHFPGTRTIIQKEPIDLRVKATNSMIDRKPRLLFP

TNSSSHLVALQGQPLVLECIAEGFPTPTIKWLRPSGPMPADRVTYQNHN

KTLQLLKVGEEDDGEYRCLAENSLGSARHAYYVTVEAAPYWLHKPQSHL

YGPGETARLDCQVQGRPQPEVTWRINGIPVEELAKDQKYRIQRGALILS

NVQPSDTMVTQCEARNRHGLLLANAYIYVVQLPAKILTADNQTYMAVQG

STAYLLCKAFGAPVPSVQWLDEDGTTVLQDERFFPYANGTLGIRDLQAN

DTGRYFCLAANDQNNVTIMANLKVKDATQITQGPRSTIEKKGSRVTFTC

QASFDPSLQPSITWRGDGRDLQELGDSDKYFIEDGRLVIHSLDYSDQGN

YSCVASTELDVVESRAQLLVVGSPGPVPRLVLSDLHLLTQSQVRVSWSP

AEDHNAPIEKYDIEFEDKEMAPEKWYSLGKVPGNQTSTTLKLSPYVHYT

FRVTAINKYGPGEPSPVSETVVTPEAAPEKNPVDVKGEGNETTNMVITW

KPLRWMDWNAPQVQYRVQWRPQGTRGPWQEQIVSDPFLVVSNTSTFVPY

EIKVQAVNSQGKGPEPQVTIGYSGEDYPQAIPELEGIEILNSSAVLVKW

RPVDLAQVKGHLRGYNVTYWREGSQRKHSKRHIHKDHVVVPANTTSVIL

SGLRPYSSYHLEVQAFNGRGSGPASEFTFSTPEGVPGHPEALHLECQSN

TSLLLRWQPPLSHNGVLTGYVLSYHPLDEGGKGQLSFNLRDPELRTHNL

TDLSPHLRYRFQLQATTKEGPGEAIVREGGTMALSGISDFGNISATAGE

-continued

NYSVVSWVPKEGQCNFRFHILFKALGEEKGGASLSPQYVSYNQSSYTQW

DLQPDTDYEIHLFKERMFRHQMAVKTNGTGRVRLPPAGFATEGWFIGFV

SAIILLLLVLLILCFIKRSKGGKYSVKDKEDTQVDSEARPMKDETFGEY

RSLESDNEEKAFGSSQPSLNGD1KPLGSDDSLADYGGSVDVQFNEDGSF

IGQYSGKKEKEAAGGNDSSGATSPINPAVALE (B) Human L1CAM isoform 2 (UniProt ID No.
P32004-2; SEQ ID NO: 3)

<u>MVVALRYVWPLLLCSPCLL</u>IQIPEEYEGHHVMEPPVITEQSPRRLVVFP

TDDISLKCEASGKPEVQFRWTRDGVHFKPKEELGVTVYQSPHSGSFTIT

GNNSNFAQRFQGIYRCFASNKLGTAMSHEIRLMAEGAPKWPKETVKPVE

VEEGESVVLPCNPPPSAEPLRIYWMNSKILHIKQDERVTMGQNGNLYFA

NVLTSDNHSDYICHAHFPGTRTIIQKEPIDLRVKATNSMIDRKPRLLFP

TNSSSHLVALQGQPLVLECIAEGFPTPTIKWLRPSGMPMPADRVTYQNHN

KTLQLLKVGEEDDGEYRCLAENSLGSARHAYYVTVEAAPYWLHKPQSHL

YGPGETARLDCQVQGRPQPEVTWRINGIPVEELAKDQKYRIQRGALILS

NVQPSDTMVTQCEARNRHGLLLANAYIYVVQLPAKILTADNQTYMAVQG

STAYLLCKAFGAPVPSVQWLDEDGTTVLQDERFFPYANGTLGIRDLQAN

DTGRYFCLAANDQNNVTIMANLKVKDATQITQGPRSTIEKKGSRVTFTC

QASFDPSLQPSITWRGDGRDLQELGDSDKYFIEDGRLVIHSLDYSDQGN

YSCVASTELDVVESRAQLLVVGSPGPVPRLVLSDLHLLTQSQVRVSWSP

AEDHNAPIEKYDIEFEDKEMAPEKWYSLGKVPGNQTSTTLKLSPYVHYT

FRVTAINKYGPGEPSPVSETVVTPEAAPEKNPVDVKGEGNETTNMVITW

KPLRWMDWNAPQVQYRVQWRPQGTRGPWQEQIVSDPFLVVSNTSTFVPY

EIKVQAVNSQGKGPEPQVTIGYSGEDYPQAIPELEGIEILNSSAVLVKW

RPVDLAQVKGHLRGYNVTYWREGSQRKHSKRHIHKDHVVVPANTTSVIL

SGLRPYSSYHLEVQAFNGRGSGPASEFTFSTPEGVPGHPEALHLECQSN

TSLLLRWQPPLSHNGVLTGYVLSYHPLDEGGKGQLSFNLRDPELRTHNL

TDLSPHLRYRFQLQATTKEGPGEAIVREGGTMALSGISDFGNISATAGE

NYSVVSWVPKEGQCNFRFHILFKALGEEKGGASLSPQYVSYNQSSYTQW

DLQPDTDYEIHLFKERMFRHQMAVKTNGTGRVRLPPAGFATEGWFIGFV

SAIILLLLVLLILCFIKRSKGGKYSVKDKEDTQVDSEARPMKDETFGEY

SDNEEKAFGSSQPSLNGDIKPLGSDDSLADYGGSVDVQFNEDGSFIGQY

SGKKEKEAAGGNDSSGATSPINPAVALE (C) Human L1CAM isoform 3 (UniProt ID No.
P32004-3; SEQ ID NO: 5)

<u>MVVALRYVWPLLLCSPCLL</u>IQIPEELMEPPVITEQSPRRLVVFPTDDIS

LKCEASGKPEVQFRWTRDGVHFKPKEELGVTVYQSPHSGSFTITGNNSN

FAQRFQGIYRCFASNKLGTAMSHEIRLMAEGAPKWPKETVKPVEVEEGE

SVVLPCNPPPSAEPLRIYWMNSKILHIKQDERVTMGQNGNLYFANVLTS

DNHSDYICHAHFPGTRTIIQKEPIDLRVKATNSMIDRKPRLLFPTNSSS

HLVALQGQPLVLECIAEGFPTPTIKWLRPSGMPMPADRVTYQNHNKTLQL

LKVGEEDDGEYRCLAENSLGSARHAYYVTVEAAPYWLHKPQSHLYGPGE

-continued

TARLDCQVQGRPQPEVTWRINGIPVEELAKDQKYRIQRGALILSNVQPS

DTMVTQCEARNRHGLLLANAYIYVVQLPAKILTADNQTYMAVQGSTAYL

LCKAFGAPVPSVQWLDEDGTTVLQDERFFPYANGTLGIRDLQANDTGRY

FCLAANDQNNVTIMANLKVKDATQITQGPRSTIEKKGSRVTFTCQASFD

PSLQPSITWRGDGRDLQELGDSDKYFIEDGRLVIHSLDYSDQGNYSCVA

STELDVVESRAQLLVVGSPGPVPRLVLSDLHLLTQSQVRVSWSPAEDHN

APIEKYDIEFEDKEMAPEKWYSLGKVPGNQTSTTLKLSPYVHYTFRVTA

INKYGPGEPSPVSETVVTPEAAPEKNPVDVKGEGNETTNMVITWKPLRW

MDWNAPQVQYRVQWRPQGTRGPWQEQIVSDPFLVVSNTSTFVPYEIKVQ

AVNSQGKGPEPQVTIGYSGEDYPQAIPELEGIEILNSSAVLVKWRPVDL

AQVKGHLRGYNVTYWREGSQRKHSKRHIHKDHVVVPANTTSVILSGLRP

YSSYHLEVQAFNGRGSGPASEFTFSTPEGVPGHPEALHLECQSNTSLLL

RWQPPLSHNGVLTGYVLSYHPLDEGGKGQLSFNLRDPELRTHNLTDLSP

HLRYRFQLQATTKEGPGEAIVREGGTMALSGISDFGNISATAGENYSVV

SWVPKEGQCNFRFHILFKALGEEKGGASLSPQYVSYNQSSYTQWDLQPD

TDYEIHLFKERMFRHQMAVKTNGTGRVRLPPAGFATEGWFIGFVSAIIL

LLLVLLILCFIKRSKGGKYSVKDKEDTQVDSEARPMKDETFGEYSDNEE

KAFGSSQPSLNGDIKPLGSDDSLADYGGSVDVQFNEDGSFIGQYSGKKE

KEAAGGNDSSGATSPINPAVALE

The signal sequence of human L1CAM corresponds to amino acids 1-19 (underlined). Thus, the mature isoforms of human L1CAM isoform 1, human L1CAM isoform 2, and human L1CAM isoform 3, consist of amino acids 20 to 1,257, 1,253, or 1,248, respectively.

The terms "antibody" and "antibodies" are terms of art and can be used interchangeably herein and refer to a molecule with an antigen binding site that specifically binds an antigen. The terms as used to herein include whole antibodies and any antigen binding fragments (i.e., "antigen-binding fragments") or single chains thereof. An "antibody" refers, in one aspect, to a glycoprotein comprising at least two heavy (H) chains and two light (L) chains inter-connected by disulfide bonds, or an antigen-binding fragment thereof. In another aspect, an "antibody" refers to a single chain antibody comprising a single variable domain, e.g., VHH domain. Each heavy chain is comprised of a heavy chain variable region (abbreviated herein as VH) and a heavy chain constant region. In certain naturally-occurring antibodies, the heavy chain constant region is comprised of three domains, CH1, CH2 and CH3. In certain naturally-occurring antibodies, each light chain is comprised of a light chain variable region (abbreviated herein as VL) and a light chain constant region. The light chain constant region is comprised of one domain, CL.

The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "Kabat numbering" and like terms are recognized in the art and refer to a system of numbering amino acid residues in the heavy and light chain variable regions of an antibody, or an antigen-binding fragment thereof. In certain aspects, the CDRs of an antibody can be determined according to the Kabat numbering system (see, e.g., Kabat E A & Wu T T (1971) *Ann NY Acad Sci* 190: 382-391 and Kabat E A et al., (1991) *Sequences of Proteins of Immunological Interest*, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific aspect, the CDRs of the antibodies described herein have been determined according to the Kabat numbering scheme.

The phrases "amino acid position numbering as in Kabat," "Kabat position," and grammatical variants thereof refer to the numbering system used for heavy chain variable domains or light chain variable domains of the compilation of antibodies in Kabat et al., *Sequences of Proteins of Immunological Interest*, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of CDR2 and inserted residues (e.g., residues 82a, 82b, and 82c, etc. according to Kabat) after heavy chain FW residue 82. See TABLE 1.

TABLE 1

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Rabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See, e.g., Lefranc, M. P. et al., *Dev. Comp. Immunol.* 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

For all heavy chain constant region amino acid positions discussed in the present disclosure, numbering is according to the EU index first described in Edelman et al., 1969, *Proc. Natl. Acad. Sci. USA* 63(1):78-85, describing the amino acid sequence of myeloma protein EU, which is the first human IgG1 sequenced. The EU index of Edelman et al. is also set forth in Kabat et al., 1991, *Sequences of Proteins of Immunological Interest*, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 EU antibody of Edelman et al. as set forth in Kabat 1991.

The numbering system used for the variable domains (both heavy chain and light chain) and light chain constant region amino acid sequence is that set forth in Kabat 1991.

Antibodies can be of any type (e.g., IgG, IgE, IgM, IgD, IgA, or IgY), any class (e.g., IgD, IgG2, IgG3, IgG4, IgA1, or IgA2), or any subclass (e.g., IgG1, IgG2, IgG3, and IgG4 in humans; and IgG1, IgG2a, IgG2b, and IgG3 in mice) of immunoglobulin molecule. Immunoglobulins, e.g., IgG1, exist in several allotypes, which differ from each other in at most a few amino acids. An antibody disclosed herein can be from any of the commonly known isotypes, classes, subclasses, or allotypes. In certain aspects, the antibodies described herein are of the IgG1, IgG2, IgG3, or IgG4 subclass or any hybrid thereof. In certain aspects, the antibodies are of the human IgG1 subclass or the human IgG2 or human IgG4 subclass.

"Antibody" includes, by way of example, both naturally-occurring and non-naturally-occurring antibodies; monoclonal and polyclonal antibodies; chimeric and humanized antibodies; human and non-human antibodies; wholly synthetic antibodies; single chain antibodies; monospecific antibodies; multispecific antibodies (including bispecific antibodies); tetrameric antibodies comprising two heavy chain and two light chain molecules; an antibody light chain monomer; an antibody heavy chain monomer; an antibody light chain dimer, an antibody heavy chain dimer; an antibody light chain-antibody heavy chain pair; intrabodies; heteroconjugate antibodies; monovalent antibodies; camelized antibodies; affybodies; anti-idiotypic (anti-Id) antibodies (including, e.g., anti-anti-Id antibodies), and single-domain antibodies (sdAbs), which include binding molecules consisting of a single monomeric variable antibody domain that are fully capable of antigen binding (e.g., a VH domain or a VL domain). Harmen M. M. and Haard H. J. *Appl Microbiol Biotechnol.* 77(1): 13-22 (2007)).

The term "antigen-binding fragment" of an antibody, as used herein, refers to one or more fragments of an antibody that retain the ability to specifically bind to an antigen (e.g., human L1CAM). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding fragment" of an antibody, e.g., an anti-L1CAM antibody described herein, include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, and disulfide-linked Fvs (sdFv); (v) a dAb fragment (Ward et al., (1989) *Nature* 341:544-546), which consists of a VH domain; and (vi) an isolated complementarity determining region (CDR) or (vii) a combination of two or more isolated CDRs which can optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)); see, e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Antigen-binding fragments can be produced by recombinant DNA techniques, or by enzymatic or chemical cleavage of intact immunoglobulins.

As used herein, the terms "variable region" or "variable domain" are used interchangeably and are common in the art. The variable region typically refers to a fragment of an antibody, generally, a fragment of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR).

Without wishing to be bound by any particular mechanism or theory, it is believed that the CDRs of the light and heavy chains are primarily responsible for the interaction and specificity of the antibody with antigen. In certain aspects, the variable region is a human variable region. In certain aspects, the variable region comprises rodent or murine CDRs and human framework regions (FRs). In particular aspects, the variable region is a primate (e.g., non-human primate) variable region. In certain aspects, the variable region comprises rodent or murine CDRs and primate (e.g., non-human primate) framework regions (FRs).

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific aspects, the light chain is a human light chain.

The terms "VL" and "VL domain" are used interchangeably to refer to the light chain variable region of an antibody.

The terms "VH" and "VH domain" are used interchangeably to refer to the heavy chain variable region of an antibody.

As used herein, the term "constant region" or "constant domain" are interchangeable and have its meaning common in the art. The constant region is an antibody fragment, e.g., a carboxyl terminal fragment of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. For IgG, the Fc region comprises immunoglobulin domains Cγt and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The CH2 domain of a human IgG Fc region extends from about amino acid 231 to about amino acid 340, whereas the CH3 domain is positioned on C-terminal side of a CH2 domain in an Fc region, i.e., it extends from about amino acid 341 to about amino acid 447 of an IgG. As used herein, the Fc region can be a native sequence Fc, including any allotypic variant, or a variant Fc (e.g., a non-naturally-occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesion).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally-occurring variants thereof. Native sequence Fc includes the various allotypes of Fc (see, e.g., Jefferis et al., (2009) mAbs 1:1; Vidarsson G. et al. *Front Immunol.* 5:520 (published online Oct. 20, 2014)).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRT, FcγRIII, and FcγRIV in mice; FcγRIA, FcγRIIA, and FcγRIIIA in humans) and one inhibitory (FcγRIIB) receptor. Human IgG1 binds to most human Fc receptors and elicits the strongest Fc effector functions. It is considered equivalent to murine IgG2a with respect to the types of activating Fc receptors that it binds to. Conversely, human IgG4 elicits the least Fc effector functions. Vidarsson G. et al. *Front Immunol.* 5:520 (published online Oct. 20, 2014).

The constant region can be manipulated, e.g., by recombinant technology, to eliminate one or more effector functions. An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with a binding domain (e.g., an antibody variable domain). Accordingly, the term "a constant region without the Fc function" include constant regions with reduced or without one or more effector functions mediated by Fc region.

Effector functions of an antibody can be reduced or avoided by different approaches. Effector functions of an antibody can be reduced or avoided by using antibody fragments lacking the Fc region (e.g., such as a Fab, F(ab')$_2$, single chain Fv (scFv), or a sdAb consisting of a monomeric VH or VL domain). Alternatively, the so-called aglycosylated antibodies can be generated by removing sugars that are linked to particular residues in the Fc region to reduce the effector functions of an antibody while retaining other valuable attributes of the Fc region (e.g., prolonged half-life and heterodimerization). Aglycosylated antibodies can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells). See, e.g., U.S. Pub. No. 20120100140. Another approach is to employ Fc regions from an IgG subclass that have reduced effector function. For example, IgG2 and IgG4 antibodies are characterized by having lower levels of Fc effector functions than IgG1 and IgG3. The residues most proximal to the hinge region in the CH2 domain of the Fc part are responsible for effector functions of antibodies as it contains a largely overlapping binding site for C1q (complement) and IgG-Fc receptors (FcγR) on effector cells of the innate immune system. Vidarsson G. et al. *Front Immunol.* 5:520 (published online Oct. 20, 2014). Accordingly, antibodies with reduced or without Fc effector functions can be prepared by generating, e.g., a chimeric Fc region which comprises a CH2 domain from an IgG antibody of the IgG4 isotype and a CH3 domain from an IgG antibody of the IgG1 isotype, or a chimeric Fc region which comprises hinge region from IgG2 and CH2 region from IgG4 (see, e.g., Lau C. et al. *J Immunol.* 191:4769-4777 (2013)), or an Fc region with mutations that result in altered Fc effector functions, e.g., reduced or no Fc functions. Such Fc regions with mutations are known in the art. See, e.g., U.S. Pub. No. 20120100140 and U.S. and PCT applications cited therein and An et al., mAbs 1:6, 572-579 (2009); the disclosures of which are incorporated by reference to their entirety.

A "hinge", "hinge domain", "hinge region", or "antibody hinge region" are used interchangeably and refer to the domain of a heavy chain constant region that joins the CH1 domain to the CH2 domain and includes the upper, middle, and lower fragments of the hinge (Roux et al., *J. Immunol.* 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 *J Immunol* 161:4083). The sequences of wild-type IgG1, IgG2, IgG3 and IgG4 hinges are known in the art. See, e.g., Kabat E A et al., (1991) *Sequences of Proteins of Immunological Interest*, Fifth Edition, U.S. Department of Health and Human Services, NIH Publication No. 91-3242; Vidarsson G. et al. *Front Immunol.* 5:520 (published online Oct. 20, 2014).

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains, as well as naturally existing variants thereof (e.g., allotypes). CH1 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH1 domains include CH1 domains with mutations that modify a biological activity of an antibody, e.g., half-life, e.g., described in U.S. Pub. No. 20120100140 and U.S. patents and publications and PCT publications cited therein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as naturally existing variants thereof (e.g., allotypes). CH2 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH2 domains include CH2 domains with mutations that modify a biological activity of an antibody, e.g., half-life and/or reduced Fc effector function, e.g., described in U.S. Pub. No. 20120100140 and U.S. patents and publications and PCT publications cited therein.

The term "CH3 domain" refers to the heavy chain constant region that is C– terminal to the CH2 domain in a heavy chain constant domain. As used herein, a CH3 domain starts at G341 and ends at K447. The term "CH3 domain" includes wildtype CH3 domains, as well as naturally existing variants thereof (e.g., allotypes). CH3 domain sequences of IgG1, IgG2, IgG3, and IgG4 (including wildtype and allotypes) are known in the art. See, e.g., Kabat E A et al., (1991) supra and Vidarsson G. et al. *Front Immunol.* 5:520 (published online Oct. 20, 2014). Exemplary CH3 domains include CH3 domains with mutations that modify a biological activity of an antibody, e.g., half-life, e.g., described in U.S. Pub. No. 20120100140 and U.S. patents and publications and PCT publications cited therein.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally-occurring variants within a specific isotype group, which variants differ in a few amino acids (see, e.g., Jefferis et al., (2009) mAbs 1:1). Antibodies described herein can be of any allotype. Allotypes of IgG1, IgG2, IgG3, and IgG4 are known in the art. See, e.g., Kabat E A et al., (1991) supra; Vidarsson G. et al. *Front Immunol.* 5:520 (published online Oct. 20, 2014); and Lefranc M P, mAbs 1:4, 1-7(2009).

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to L1CAM is substantially free of antibodies that specifically bind antigens other than L1CAM). An isolated antibody that specifically binds to an epitope of L1CAM can, however, have cross-reactivity to other L1CAM proteins from different species.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$ and is expressed as a molar concentration (M), whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as immunoassays (e.g., enzyme-linked immunosorbent assay (ELISA)), BIACORE®, BLI (Bio-layer interferometry), or kinetic exclusion assay (KINEXA)°.

As used herein, the terms "specifically binds," "specifically recognizes," "specific binding," "selective binding," and "selectively binds," are analogous terms in the context of antibodies and refer to molecules (e.g., antibodies) that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIACORE®, KINEXA® 3000 instrument (Sapidyne Instruments, Boise, ID), or other assays known in the art. In a specific aspect, molecules that specifically bind to an antigen bind to the antigen with a $K_A$ that is at least 2 logs, 2.5 logs, 3 logs, 4 logs or greater than the $K_A$ when the molecules bind to another antigen.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $10^{-9}$ M or less, and most preferably between $10^{-8}$ M and $10^{-10}$ M or less, when determined by, e.g., immunoassays (e.g., ELISA) surface plasmon resonance (SPR) technology in a BIACORE™ 2000 instrument using the predetermined antigen, or BLI (Bio-layer interferometry) but does not bind with high affinity to unrelated antigens.

As used herein, the term "antigen" refers to any natural or synthetic immunogenic substance, such as a protein, peptide, or hapten. An antigen can be L1CAM or a fragment thereof.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). Epitopes formed from contiguous amino acids are typically, but not always, retained on exposure to denaturing solvents, whereas epitopes formed by tertiary folding are typically lost on treatment with denaturing solvents. An epitope typically includes at least 1, 2, 3, 4, 5, 6, 7, 8, 9, 10, 11, 12, 13, 14, 15, or 20 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from L1CAM) are tested for reactivity with a given antibody (e.g., anti-L1CAM antibody). Methods of determining spatial conformation of epitopes include techniques in the art and those described herein, for example, x-ray crystallography, 2-dimensional nuclear magnetic resonance and HDX-MS (see, e.g., Epitope Mapping Protocols in Methods in Molecular Biology, Vol. 66, G. E. Morris, Ed. (1996)).

In certain aspects, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization can be accomplished using any of the known methods in the art (e.g., Giege R et al., (1994) *Acta Crystallogr D Biol Crystallogr* 50(Pt 4): 339-350; McPherson A (1990) *Eur J Biochem* 189: 1-23; Chayen N E (1997) *Structure* 5: 1269-1274; McPherson A (1976) *J Blot Chem* 251: 6300-6303). Antibody:antigen crystals can be studied using well known X-ray diffraction techniques and can be refined using computer software such as X-PLOR (Yale University, 1992, distributed by Molecular Simulations, Inc.; see, e.g., *Meth Enzymol* (1985) volumes 114 & 115, eds Wyckoff H W et al., U.S. 2004/0014194), and BUSTER (Bricogne G (1993) *Acta Crystallogr D Biol Crystallogr* 49(Pt 1): 37-60; Bricogne G (1997) *Meth Enzymol* 276A: 361-423, ed Carter C W; Roversi P et al., (2000) *Acta Crystallogr D Biol Crystallogr* 56(Pt 10): 1316-1323). Mutagenesis mapping studies can be accomplished using any method known to one of skill in the art. See, e.g., Champe M et al., (1995) *J Biol Chem* 270: 1388-1394 and Cunningham B C & Wells J A (1989) *Science* 244: 1081-1085 for a description of mutagenesis techniques, including alanine scanning mutagenesis techniques.

The term "epitope mapping" refers to the process of identification of the molecular determinants for antibody-antigen recognition.

The term "binds to the same epitope" as a reference antibody means that the antibodies bind to the same segment of amino acid residues, as determined by a given method. Techniques for determining whether antibodies bind to the "same epitope on L1CAM" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE® surface plasmon resonance (SPR) analysis. In some aspects, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, NY, USA 1999. Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include: competition for binding to cells expressing L1CAM, e.g., by flow cytometry, such as described in the Examples. Other methods include: SPR (e.g.,) BIACORE®, BLI (Bio-layer interferometry), solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label MA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 instrument using the predetermined antigen, e.g., recombinant human MICA or MICB, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human L1CAM" refers to an antibody that binds to soluble or cell bound human L1CAM with a $K_D$ of $10^{-7}$ M or less, such as approximately less than $10^{-8}$ M, $10^{-9}$ M or $10^{-10}$ M or even lower. An antibody that "cross-reacts with cynomolgus L1CAM" refers to an antibody that binds to cynomolgus L1CAM with a $K_D$ of $10^{-7}$ M or less, such as approximately less than $10^{-8}$ M, $10^{-9}$ M or $10^{-10}$ M or even lower. In some aspects, such antibodies that do not cross-react with L1CAM from a non-human species exhibit essentially undetectable binding against these proteins in standard binding assays.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "KID", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. Available methods for determining the $K_D$ of an antibody include surface plasmon resonance, a biosensor system such as a BIACORE®, BLI (Bio-layer interferometry) system or flow cytometry and Scatchard analysis.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-10}$ M or less, or $10^{-8}$ M or less.

The term "$EC_{50}$" in the context of an in vitro or in vivo assay using an antibody or antigen binding fragment thereof, refers to the concentration of an antibody or an antigen-binding fragment thereof that induces a response that is 50% of the maximal response, i.e., halfway between the maximal response and the baseline.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one aspect, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell and/or by a recombinant, combinatorial human antibody library.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "human antibody" (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "chimeric antibody" refers to an antibody in which the variable regions are derived from one species and the constant regions are derived from another species, such as an antibody in which the variable regions are derived from a mouse antibody and the constant regions are derived from a human antibody.

The term "cross-reacts," as used herein, refers to the ability of an antibody described herein to bind to L1CAM from a different species. For example, an antibody described herein that binds human L1CAM can also bind another species of L1CAM (e.g., mouse L1CAM). As used herein, cross-reactivity can be measured by detecting a specific reactivity with purified antigen in binding assays (e.g., SPR, ELISA) or binding to, or otherwise functionally interacting with, cells physiologically expressing L1CAM. Methods for determining cross-reactivity include standard binding assays as described herein, for example, by BIACORE® surface plasmon resonance (SPR) analysis using a BIACORE® 2000 SPR instrument (Biacore AB, Uppsala, Sweden), or flow cytometric techniques.

The term "naturally-occurring" as applied to an object herein refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

"Conservative amino acid substitutions" refer to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In some aspects, a predicted nonessential amino acid residue in an anti-L1CAM antibody is replaced with another amino acid residue from the same side chain family. Methods of identifying nucleotide and amino acid conservative substitutions which do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (I *Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and)(BLAST programs (version 2.0) of Altschul, et al. (1990) *J Mol. Biol.* 215:403-10. BLAST nucleotide searches can be performed with the NBLAST program, score=100, word length=12 to obtain nucleotide sequences homologous to the nucleic acid molecules described herein. BLAST protein searches can be performed with the) (BLAST program, score=50, word length=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g.,)(BLAST and NBLAST) can be used. See world-wideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. *Current Protocols in Molecular Biology, Greene Publishing and* Wiley Interscience, *New York* (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

An "immune response" is as understood in the art, and generally refers to a biological response within a vertebrate against foreign agents or abnormal, e.g., cancerous cells, which response protects the organism against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell, a Th cell, a CD4$^+$ cell, a CD8$^+$ T cell, or a Treg cell, or activation or inhibition of any other cell of the immune system, e.g., NK cell.

"Immunotherapy" refers to the treatment of a subject afflicted with, or at risk of contracting or suffering a recurrence of, a disease by a method comprising inducing, enhancing, suppressing or otherwise modifying the immune system or an immune response.

As used herein, "administering" refers to the physical introduction of a therapeutic agent or a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraventricle, intravitreal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the phrase "supresses growth of a tumor" includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%. In some aspects, inhibition of tumor growth is measured as the percent tumor growth inhibition (TGI %). TGI % can be determined by calculating the TGI at dat "t" calculated from all treatment animals according to the formula: $[1-((T_t/T_0)/(C_t/C_0))]/[(C_t-C_0)/C_t]*100$ [Formula 1], where $T_t$=individual tumor size of treated animal at time 't', $T_0$=individual tumor size of treated animal at first measurement, $C_t$=median tumors size of control animals at time T, $C_0$=median tumor size of control animals at first measurement.

As used herein, "cancer" refers a broad group of diseases characterized by the uncontrolled growth of abnormal cells in the body. Unregulated cell division can result in the formation of malignant tumors or cells that invade neighboring tissues and can metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease or enhancing overall survival. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, an increase in overall survival (the length of time from either the date of diagnosis or the start of treatment for a disease, such as cancer, that patients diagnosed with the disease are still alive), or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that promotes cancer regression in a subject. In some aspects, a therapeutically effective amount of the drug promotes cancer regression to the point of eliminating the cancer. "Promoting cancer regression" means that administering an effective amount of the drug, alone or in combination with an antineoplastic agent, results in a reduction in tumor growth or size, necrosis of the tumor, a decrease in severity of at least one disease symptom, an increase in frequency and duration of disease symptom-free periods, an increase in overall survival, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug inhibits cell growth or tumor growth by at least about 20%, by at least about 40%, by at least about 60%, or by at least about 80% relative to untreated subjects. In some aspects, a therapeutically effective amount or dosage of the drug completely inhibits cell growth or tumor growth, i.e., inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In some aspects described herein, tumor regression can be observed and continue for a period of at least about 20 days, at least about 40 days, or at least about 60 days.

As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

As used herein, the terms "ug" and "uM" are used interchangeably with "μg" and "μM," respectively.

Various aspects described herein are described in further detail in the following subsections.

II. Anti-L1CAM Antibodies

Disclosed herein are antibodies, e.g., monoclonal antibodies, which are characterized by particular functional features or properties. For example, the antibodies specifically bind to mammalian (e.g., human and mouse) L1CAM and exhibit one or more of the following functional properties:

(a) exhibits improved productivity compared to the mAb417 antibody
(b) exhibits improved affinity as measured by the equilibrium dissociation constant ($K_D$) compared to the mAb417 antibody;
(c) exhibits improved PI value compared to the mAb417 antibody;
(d) exhibits improved affinity as measured by the association constant (K) compared to the mAb417 antibody;
(e) prevents and/or treats diseases or conditions which comprise a tumor; or
(f) any combination thereof.

In some aspects, the anti-L1CAM antibody or antigen-binding fragment thereof exhibits improved productivity compared to the mAb417 antibody, for example, the improved productivity is at least 55 mg/L, at least 56 mg/L, at least 57 mg/L, at least 58 mg/L, at least 59 mg/L, at least about 60 mg/L, at least about 61 mg/L, at least about 62 mg/L, at least about 63 mg/L, at least about 64 mg/L, at least about 65 mg/L, at least about 66 mg/L, at least about 67 mg/L, at least about 68 mg/L, at least about 69 mg/L, at least about 70 mg/L, at least about 71 mg/L, at least about 72 mg/L, at least about 73 mg/L, at least about 74 mg/L, at least about 75 mg/L, at least about 76 mg/L, at least about 77 mg/L, at least about 78 mg/L, at least about 79 mg/L, at least about 80 mg/L, at least about 81 mg/L, at least about 82 mg/L, at least about 83 mg/L, at least about 84 mg/L, or at least about 85 mg/L, when expressed according to example 3.

In some aspects, the anti-L1CAM antibody or antigen-binding fragment thereof specifically binds to human L1CAM with high affinity, for example, with a $K_D$ of less than $2.6\times10^{-10}$ M, less than $2.5\times10^{-10}$ M, less than $2.0\times10^{-10}$ M, less than $1.5\times10^{-10}$ M, less than $1.0\times10^{-10}$ M, less than $9\times10^{-11}$ M, less than $8\times10^{-11}$ M, less than $7\times10^{-11}$ M, less than $6\times10^{-11}$ M, less than $5\times10^{-11}$ M, less than $4\times10^{-11}$ M, less than $3\times10^{-11}$ M, less than $2\times10^{-11}$ M, less than $1\times10^{-11}$ M, less than $9\times10^{-12}$ M, less than $8\times10^{-12}$ M, less than $7\times10^{-12}$ M, less than $6\times10^{-12}$ M, less than $5\times10^{-12}$ M, less than $4\times10^{-12}$ M, less than $3\times10^{-12}$ M, less than $2\times10^{-12}$ M, less than $1\times10^{-12}$ M, less than $9\times10^{-13}$ M, or less than $8\times10^{-13}$ M, e.g., as measured by the Bio-layer interferometry (BLI) method (e.g., as described in the Examples). In some aspects, the anti-L1CAM antibody or antigen-binding fragment thereof specifically binds to human L1CAM with a $K_D$ of less than $2\times10^{-10}$ M, less than $1.9\times10^{-10}$ M, less than $1.8\times10^{-10}$ M, less than $1.7\times10^{-10}$ M, less than $1.6\times10^{-10}$ M, less than $1.5\times10^{-10}$ M, less than $1.4\times10^{-10}$ M, less than $1.3\times10^{-10}$ M, less than $1.2\times10^{-10}$ M, or less than $1.1\times10^{-10}$ M. In some aspects, the anti-L1CAM antibody or antigen-binding fragment thereof specifically binds to human L1CAM with a $K_D$ of less than $1.1\times10^{-10}$ M. In other aspects, the anti-L1CAM antibody or antigen-binding fragment thereof specifically binds to human L1CAM with a $K_D$ of less than $9\times10^{-12}$ M. In some aspects, the anti-L1CAM antibody or antigen-binding fragment thereof specifically binds to human L1CAM with a $K_D$ of less than $1\times10^{-12}$ M. In some aspects, the anti-L1CAM antibody or antigen-binding fragment thereof specifically binds to human L1CAM with a $K_D$ of less than $8\times10^{-11}$ M. In some aspects, the anti-L1CAM antibody or antigen-binding fragment thereof specifically binds to human L1CAM with a $K_D$ of less than $1\times10^{-12}$ M. In some aspects, the anti-L1CAM antibody or antigen-binding fragment thereof specifically binds to human L1CAM with a $K_D$ of less than $1.05\times10^{-10}$ M. In some aspects, the anti-L1CAM antibody or antigen-binding fragment thereof specifically binds to human L1CAM with a $K_D$ of about $8.22\times10^{-12}$ M. In some aspects, the anti-L1CAM antibody or antigen-binding fragment thereof specifically binds to human L1CAM with a $K_D$ of about $7.4\times10^{-11}$ M. In some aspects, the anti-L1CAM antibody or antigen-binding fragment thereof specifically binds to human L1CAM with a $K_D$ of about $9.6\times10^{-11}$ M.

In some aspects, the anti-L1CAM antibody or antigen-binding fragment thereof specifically binds to human L1CAM with high affinity, for example, with a K of less than $5\times10^{-10}$ M, less than $4\times10^{-10}$ M, less than $3\times10^{-10}$ M, less than $2\times10^{-10}$ M, less than $1.0\times10^{-10}$ M, less than $9\times10^{-11}$ M, less than $8\times10^{-11}$ M, less than $7\times10^{-11}$ M, less than $6\times10^{-11}$ M, less than $5\times10^{-11}$ M, less than $4\times10^{-11}$ M, less than $3\times10^{-11}$ M, less than $2\times10^{-11}$ M, less than $1\times10^{-11}$ M, less than $9\times10^{-12}$ M, less than $8\times10^{-12}$ M, less than $7\times10^{-12}$ M, less than $6\times10^{-12}$ M, less than $5\times10^{-12}$ M, less than $4\times10^{-12}$ M, less than $3\times10^{-12}$ M, less than $2\times10^{-12}$ M, less than $1\times10^{-12}$ M, less than $9\times10^{-13}$ M, or less than $8\times10^{-13}$ M, e.g., as measured by ELISA (e.g., as described in the Examples).

Standard assays to evaluate the binding ability of the antibody toward L1CAM of various species are known in the art, including for example, ELISAs, Western blots, and RIAs. Suitable assays are described in detail in the Examples. The binding kinetics (e.g., binding affinity) of the antibodies also can be assessed by standard assays known in the art, such as by ELISA, BIACORE® analysis, or KINEXA®. Assays to evaluate the effects of the antibodies on functional properties of L1CAM (e.g., ligand binding) are described in further detail infra and in the Examples.

In some aspects, the anti-L1CAM antibody or antigen-binding fragment thereof exhibits improved isoelectric point (PI) value of less than 9.6, less than 9.5, less than 9.4, less than 9.3, less than 9.2, less than 9.1, less than 9.0, less than 8.9, less than 8.8, less than 8.7, less than 8.6, less than 8.5, less than 8.4, less than 8.3, less than 8.2, less than 8.1, less than 8.0, less than 7.9, less than 7.8, less than 7.7, or less than 7.6., as measured by capillary isoelectricfocusing (cIEF) method (e.g., as described in the Examples).

In certain aspects, anti-L1CAM antibodies or antigen binding fragments thereof specifically bind to the same L1CAM epitope as a reference antibody comprising a heavy chain variable region (VH) and a light chain variable region (VL), wherein the (a) the VH of the reference antibody comprises SEQ ID NO: 23 and the VL of the reference antibody comprises SEQ ID NO: 24, (b) the VH of the reference antibody comprises SEQ ID NO: 25 and the VL of the reference antibody comprises SEQ ID NO: 26, (c) the VH of the reference antibody comprises SEQ ID NO: 27 and the VL of the reference antibody comprises SEQ ID NO: 28, (d) the VH of the reference antibody comprises SEQ ID NO: 29 and the VL of the reference antibody comprises SEQ ID NO: 30, or (e) the VH of the reference antibody comprises SEQ ID NO: 31 and the VL of the reference antibody comprises SEQ ID NO: 32.

In certain aspects, anti-L1CAM antibodies or antigen binding fragments thereof specifically bind to the same L1CAM epitope as a reference antibody comprising VH complementarity determining region 1(CDR1), VH CDR2, and VH CDR3, and VL CDR1, VL CDR2, and VL CDR3, wherein at least one amino acid in the VH CDR1, VH CDR2, VH CDR3, VL CDR1, VL CDR2, and/or VL CDR3 of the antibody or antigen-binding fragment thereof is different from the VH CDR1, VH CDR2, VH CDR3, VL CDR1, VL CDR2, and/or VL CDR3 of the reference antibody (e.g., mAb417 antibody), wherein the VH CDR1, VH CDR2, VH CDR3 of the reference antibody comprise the amino acid sequence of SEQ ID NO: 2, SEQ ID NO: 9, and SEQ ID NO: 4, respectively, and the VL CDR1, VL CDR2, and VL CDR3 of the reference antibody comprise the amino acid sequence of SEQ ID NO: 6, SEQ ID NO: 7, and SEQ ID NO: 11, respectively. In certain aspects, the at least one amino acid difference comprises (i) glutamine at residue 5 in the VH CDR2; (ii) serine at residue 8 in the VL CDR1; and/or (iii) proline at residue 8 in the VL CDR3 of the anti-L1CAM antibody or antigen-binding fragment thereof. In certain aspects, the at least one amino acid difference comprises (i) alanine, glycine, phenylalanine, tyrosine, threonine, proline, and tryptophan at residues 3 to 9, respectively in the VL CDR3; (ii) alanine, glycine, phenylalanine, tyrosine, serine, proline, and tryptophan at residues 3 to 9, respectively in the VL CDR3 or (iii) leucine, valine, or histidine, tryptophan, or phenylalanine, tyrosine, proline, and tryptophan at residues 4 to 9, respectively in the VL CDR3 of the anti-L1CAM antibody or antigen-binding fragment thereof.

In certain aspects, anti-L1CAM antibodies or antigen binding fragments thereof cross-competes for binding to L1CAM epitope as a reference antibody comprising VH complementarity determining region 1(CDR1), VH CDR2, and VH CDR3, and VL CDR1, VL CDR2, and VL CDR3, wherein at least one amino acid in the VH CDR1, VH CDR2, VH CDR3, VL CDR1, VL CDR2, and/or VL CDR3 of the antibody or antigen-binding fragment thereof is different from the VH CDR1, VH CDR2, VH CDR3, VL CDR1, VL CDR2, and/or VL CDR3 of the reference antibody (e.g., mAb417 antibody), (i) wherein the VH CDR1, VH CDR2, VH CDR3 of the reference antibody comprise the amino acid sequence of SEQ ID NO: 2, SEQ ID NO: 9, and SEQ ID NO: 4, respectively, and the VL CDR1, VL CDR2, and VL CDR3 of the reference antibody comprise the amino acid sequence of SEQ ID NO: 6, SEQ ID NO: 7, and SEQ ID NO: 11, respectively. In certain aspects, the at least one amino acid difference comprises (i) glutamine at residue 5 in the VH CDR2; (ii) serine at residue 8 in the VL CDR1; and/or (iii) proline at residue 8 in the VL CDR3 of the anti-L1CAM antibody or antigen-binding fragment thereof. In certain aspects, the at least one amino acid difference comprises (i) alanine, glycine, phenylalanine, tyrosine, threonine, proline, and tryptophan at residues 3 to 9, respectively in the VL CDR3; (ii) alanine, glycine, phenylalanine, tyrosine, serine, proline, and tryptophan at residues 3 to 9, respectively in the VL CDR3 or (iii) leucine, valine, or histidine, tryptophan, or phenylalanine, tyrosine, proline, and tryptophan at residues 4 to 9, respectively in the VL CDR3 of the anti-L1CAM antibody or antigen-binding fragment thereof.

In certain aspects, anti-L1CAM antibodies or antigen binding fragments thereof cross-competes for binding to L1CAM epitope with a reference antibody comprising a heavy chain variable region (VH) and a light chain variable region (VL), wherein the (a) the VH of the reference antibody comprises SEQ ID NO: 23 and the VL of the reference antibody comprises SEQ ID NO: 24, (b) the VH of the reference antibody comprises SEQ ID NO: 25 and the VL of the reference antibody comprises SEQ ID NO: 26, (c) the VH of the reference antibody comprises SEQ ID NO: 27 and the VL of the reference antibody comprises SEQ ID NO: 28, (d) the VH of the reference antibody comprises SEQ ID NO: 29 and the VL of the reference antibody comprises SEQ ID NO: 30, or (e) the VH of the reference antibody comprises SEQ ID NO: 31 and the VL of the reference antibody comprises SEQ ID NO: 32.

Competing antibodies bind to the same epitope, an overlapping epitope, or to adjacent epitopes (e.g., as evidenced by steric hindrance). Whether two antibodies compete with each other for binding to a target can be determined using competition experiments known in the art such as RIA and EIA.

Techniques for determining whether two antibodies bind to the same epitope include, e.g., epitope mapping methods, such as, x-ray analyses of crystals of antigen:antibody complexes which provides atomic resolution of the epitope and hydrogen/deuterium exchange mass spectrometry (HDX-MS), methods monitoring the binding of the antibody to antigen fragments or mutated variations of the antigen, where loss of binding due to a modification of an amino acid residue within the antigen sequence is often considered an indication of an epitope component, computational combinatorial methods for epitope mapping.

In certain aspects, provided herein is an antibody or antigen-binding fragment thereof that binds to L1CAM (e.g., human L1CAM) with a 20%, 25%, 30%, 35%, 40%, 45%, 50%, 55%, 60%, 65%, 70%, 75%, 80%, 85%, 90%, 95% or higher affinity than to another protein in the L1CAM family as measured by, e.g., a immunoassay (e.g., ELISA), surface plasmon resonance, BLI (Bio-layer interferometry), or kinetic exclusion assay. In a specific aspect, provided herein is an antibody or antigen-binding fragment thereof that binds to L1CAM (e.g., human L1CAM) with no cross reactivity with another protein in the L1CAM family as measured by, e.g., a immunoassay.

In certain aspects, the anti-L1CAM antibodies are not native antibodies or are not naturally-occurring antibodies. For example, the anti-L1CAM antibodies have post-translational modifications that are different from those of antibodies that are naturally-occurring, such as by having more, less or a different type of post-translational modification.

III. Exemplary Anti-L1CAM Antibodies

Particular antibodies that can be used in the methods disclosed herein are antibodies, e.g., monoclonal antibodies, having the CDR and/or variable region sequences of antibody Ab612, Ab4H5, Ab2C2, Ab4H6, and Ab5D12 constructed in Examples 1 and 2 as well as antibodies having at least 80% identity (e.g., at least about 85%, at least about 90%, at least about 95%, at least about 96%, at least about 97%, at least about 98%, at least about 99%, or about 100% identity) to their variable region or CDR sequences. The VH amino acid sequences of Ab612, Ab4H5, Ab2C2, Ab4H6, and Ab5D12 are set forth in SEQ ID NOs: 23, 25, 27, 29, and 31, respectively. The VL amino acid sequences of Ab612, Ab4H5, Ab2C2, Ab4H6, and Ab5D12 are set forth in SEQ ID NOs: 24, 26, 28, 30, and 32, respectively.

TABLE 2

Variable heavy chain CDR amino acid sequences (according to Kabat system)

| Antibody | VH-CDR1 | VH-CDR2 | VH-CDR3 |
| --- | --- | --- | --- |
| Anti-L1CAM ("Ab612") | RFGMH (SEQ ID NO: 2) | FISNEGSNKYYADSVKG (SEQ ID NO: 10) | GRAYGSGSLFDP (SEQ ID NO: 4) |
| Anti-L1CAM ("Ab4H5") | RFGMH (SEQ ID NO: 2) | FISNEGSNKYYADSVKG (SEQ ID NO: 10) | GRAYGSGSLFDP (SEQ ID NO: 4) |
| Anti-L1CAM ("Ab2C2") | RFGMH (SEQ ID NO: 2) | FISNEGSNKYYADSVKG (SEQ ID NO: 10) | GRAYGSGSLFDP (SEQ ID NO: 4) |

TABLE 2-continued

Variable heavy chain CDR amino acid sequences (according to Kabat system)

| Antibody | VH-CDR1 | VH-CDR2 | VH-CDR3 |
|---|---|---|---|
| Anti-L1CAM ("Ab4H6") | RFGMH (SEQ ID NO: 2) | FISNEGSNKYYADSVKG (SEQ ID NO: 10) | GRAYGSGSLFDP (SEQ ID NO: 4) |
| Anti-L1CAM ("Ab5D12") | RFGMH (SEQ ID NO: 2) | FISNEGSNKYYADSVKG (SEQ ID NO: 10) | GRAYGSGSLFDP (SEQ ID NO: 4) |

TABLE 3

Variable light chain CDR amino acid sequences (according to Kabat system)

| Antibody | VL-CDR1 | VL-CDR2 | VL-CDR3 |
|---|---|---|---|
| Anti-L1CAM ("Ab612") | RASRTISSYVN (SEQ ID NO: 12) | AASNLHS (SEQ ID NO: 7) | QQSIGRGPVT (SEQ ID NO: 13) |
| Anti-L1CAM ("Ab4H5") | RASRTISSYVN (SEQ ID NO: 12) | AASNLHS (SEQ ID NO: 7) | QQAGFYTPWT (SEQ ID NO: 15) |
| Anti-L1CAM ("Ab2C2") | RASRTISSYVN (SEQ ID NO: 12) | AASNLHS (SEQ ID NO: 7) | QQAGFYSPWT (SEQ ID NO: 17) |
| Anti-L1CAM ("Ab4H6") | RASRTISSYVN (SEQ ID NO: 12) | AASNLHS (SEQ ID NO: 7) | QQSLHFYPWT (SEQ ID NO: 19) |
| Anti-L1CAM ("Ab5D12") | RASRTISSYVN (SEQ ID NO: 12) | AASNLHS (SEQ ID NO: 7) | QQSLVWYPWT (SEQ ID NO: 21) |

TABLE 4A

Variable heavy chain amino acid sequence

| Antibody | VH Amino Acid Sequence (SEQ ID NO) |
|---|---|
| Anti-L1CAM ("Ab612") | EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO: 23) |
| Anti-L1CAM ("Ab4H5") | EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO:25 ) |
| Anti-L1CAM ("Ab2C2") | EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO: 27) |
| Anti-L1CAM ("Ab4H6") | EVQLVESGGG VVQPGGSLRL SCAASGFTFS RFGMHWVRQA PGKGLEWVAF ISNEGSNKYY ADSVKGRFTI SRDNSANTLY LQMNSLRAED TAVYYCARGR AYGSGSLFDP WGQGTLVTVS S (SEQ ID NO: 29) |
| Anti-L1CAM ("Ab5D12") | EVQLVESGGG VVQPGGSLRL SCAASGFTFS RFGMHWVRQA PGKGLEWVAF ISNEGSNKYY ADSVKGRFTI SRDNSANTL Y LQMNSLRAED TAVYYCARGR AYGSGSLFDP WGQGTLVTVS S (SEQ ID NO: 31) |

TABLE 4B

Variable light chain amino acid sequence

| Antibody | VL Amino Acid Sequence (SEQ ID NO) |
|---|---|
| Anti-L1CAM ("Ab612") | DIQL TQSPSS LSASVGDRVT ITCRASRTIS SYVNWYRQRP GKAPESLIYA ASNLHSGVPS RFSGSGSGTD FTLTISSLQP EDFATYYCQQ SIGRGPVTFG QGTKLEIK (SEQ ID NO: 24) |
| Anti-L1CAM ("Ab4H5") | DIQL TQSPSS LSASVGDRVT ITCRASRTIS SYVNWYRQRP GKAPESLIYA ASNLHSGVPS RFSGSGSGTD FTLTISSLQP EDFATYYCQQ AGFYTPWTFG QGTKLEIK (SEQ ID NO: 26) |
| Anti-L1CAM ("Ab2C2") | DIQL TQSPSS LSASVGDRVT ITCRASRTIS SYVNWYRQRP GKAPESLIYA ASNLHSGVPS RFSGSGSGTD FTLTISSLQP EDFATYYCQQ AGFYSPWTFG QGTKLEIK (SEQ ID NO: 28) |
| Anti-L1CAM ("Ab4H6") | DIQL TQSPSS LSASVGDRVT ITCRASRTIS SYVNWYRQRP GKAPESLIYA ASNLHSGVPS RFSGSGSGTD FTLTISSLQP EDFATYYC QQSLHFYPWT FG QGTKLEIK (SEQ ID NO: 30) |
| Anti-L1CAM ("Ab5D12") | DIQL TQSPSS LSASVGDRVT ITCRASRTIS SYVNWYRQRP GKAPESLIYA ASNLHSGVPS RFSGSGSGTD FTLTISSLQP EDFATYYC QQSLVWYPWT FG QGTKLEIK (SEQ ID NO: 32) |

Accordingly, provided herein is an isolated anti-L1CAM antibody, or an antigen-binding fragment thereof, comprising heavy and light chain variable regions, wherein the heavy chain variable region comprises the amino acid sequence of SEQ ID NOs: 23, 25, 27, 29, or 31. In other aspects, the isolated anti-L1CAM antibody, or an antigen binding fragment thereof, comprises the CDRs of the heavy chain variable region selected from the group consisting of SEQ ID NOs: 2, 10, or 4.

Also provided is an isolated anti-L1CAM antibody, or an antigen-binding fragment thereof, comprising heavy and light chain variable regions, wherein the light chain variable region comprises the amino acid sequence of SEQ ID NOs: 24, 26, 28, 30, or 32. In other aspects, the isolated anti-L1CAM antibody, or an antigen binding fragment thereof, comprises the CDRs of the light chain variable region selected from the group consisting of SEQ ID NOs: 12, 7, 13, 15, 17, 19, or 21.

In certain aspects, the isolated anti-L1CAM, or an antigen binding fragment thereof, comprises the CDRs of the heavy chain variable region selected from the group consisting of SEQ ID NOs: 2, 10, or 4 and the CDRs of the light chain variable region selected from the group consisting of SEQ ID NOs: 12, 7, 13, 15, 17, 19, or 21.

Also provided is an isolated anti-L1CAM antibody, or an antigen-binding fragment thereof, comprising heavy and light chain variable regions, (i) wherein the heavy chain variable region comprises the amino acid sequence of SEQ ID NO: 23 and wherein the light chain variable region comprises the amino acid sequence of SEQ ID NO: 24; (ii) wherein the heavy chain variable region comprises the amino acid sequence of SEQ ID NO: 25 and wherein the light chain variable region comprises the amino acid sequence of SEQ ID NO: 26; (iii) wherein the heavy chain variable region comprises the amino acid sequence of SEQ ID NO: 27 and wherein the light chain variable region comprises the amino acid sequence of SEQ ID NO: 28; (iv) wherein the heavy chain variable region comprises the amino acid sequence of SEQ ID NO: 29 and wherein the light chain variable region comprises the amino acid sequence of SEQ ID NO: 30; or (v) wherein the heavy chain variable region comprises the amino acid sequence of SEQ ID NO: 31 and wherein the light chain variable region comprises the amino acid sequence of SEQ ID NO: 32.

Provided herein is an isolated anti-L1CAM antibody, or an antigen-binding fragment thereof, comprising a heavy chain variable region and a light chain variable region, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 23, 25, 27, 29, or 31.

Also provided herein is an isolated anti-L1CAM antibody, or an antigen-binding fragment thereof, comprising a heavy chain variable region and a light chain variable region, wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 24, 26, 28, 30, or 32.

Also provided is an isolated anti-L1CAM antibody, or an antigen-binding fragment thereof, comprising heavy and light chain variable regions, wherein the heavy chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 23, 25, 27, 29, and 31, and wherein the light chain variable region comprises an amino acid sequence which is at least about 80%, at least about 85%, at least about 90%, at least about 95%, at least about 96%, at least about 97%, at least about 98%, at least about 99%, or about 100% identical to the amino acid sequence set forth as SEQ ID NOs: 24, 26, 28, 30, or 32.

In some aspects, the disclosure provides an isolated anti-L1CAM antibody, or an antigen-binding fragment thereof, comprising:
  (a) heavy and light chain variable region sequences comprising SEQ ID NOs: 23 and 24, respectively;
  (b) heavy and light chain variable region sequences comprising SEQ ID NOs: 25 and 26, respectively;
  (c) heavy and light chain variable region sequences comprising SEQ ID NOs: 27 and 28, respectively;
  (d) heavy and light chain variable region sequences comprising SEQ ID NOs: 29 and 30, respectively; or (e) heavy and light chain variable region sequences comprising SEQ ID NOs: 31 and 32, respectively.

The amino acid sequences of the VH CDR1, CDR2, and CDR3 for antibody Ab612, Ab4H5, Ab2C2, Ab4H6, and Ab5D12 are set forth in SEQ ID NOs: 2, 10, and 4, respectively. The amino acid sequences of the VL CDR1, CDR2, and CDR3 for Ab612 are set forth in SEQ ID NOs: 12, 7, and 13, respectively. The amino acid sequences of the VL CDR1, CDR2, and CDR3 for Ab4H5 are set forth in SEQ ID NOs: 12, 7, and 15, respectively. The amino acid sequences of the VL CDR1, CDR2, and CDR3 for Ab2C2 are set forth in SEQ ID NOs: 12, 7, and 17, respectively. The amino acid sequences of the VL CDR1, CDR2, and CDR3 for Ab4H6 are set forth in SEQ ID NOs: 12, 7, and 19, respectively. The amino acid sequences of the VL CDR1, CDR2, and CDR3 for Ab5D12 are set forth in SEQ ID NOs: 12, 7, and 21, respectively.

In some aspects, the anti-L1CAM antibody or antigen-binding fragment thereof of the disclosure, which specifically binds to human L1CAM, comprises:
 (a) a VH CDR1 comprising the amino acid sequence of SEQ ID NO: 2; and/or
 (b) a VH CDR2 comprising the amino acid sequence of SEQ ID NO: 10; and/or
 (c) a VH CDR3 comprising the amino acid sequence of SEQ ID NO: 4.

In some aspects, the anti-L1CAM antibody or antigen-binding fragment thereof, which specifically binds to human L1CAM, comprises:
 (a) a VL CDR1 comprising the amino acid sequence of SEQ ID NO: 12; and/or
 (b) a VL CDR2 comprising the amino acid sequence of SEQ ID NO: 7; and/or
 (c) a VL CDR3 comprising the amino acid sequence of SEQ ID NO: 13.

In some aspects, the anti-L1CAM antibody or antigen-binding fragment thereof, which specifically binds to human L1CAM, comprise:
 (a) a VH CDR1 comprising the amino acid sequence of SEQ ID NO: 2;
 (b) a VH CDR2 comprising the amino acid sequence of SEQ ID NO: 10;
 (c) a VH CDR3 comprising the amino acid sequence of SEQ ID NO: 4;
 (d) a VL CDR1 comprising the amino acid sequence of SEQ ID NO: 12;
 (e) a VL CDR2 comprising the amino acid sequence of SEQ ID NO: 7; and/or
 (f) a VL CDR3 comprising the amino acid sequence of SEQ ID NO: 13.

In some aspects, the anti-L1CAM antibody or antigen-binding fragment thereof, which specifically binds to human L1CAM, comprises:
 (a) a VL CDR1 comprising the amino acid sequence of SEQ ID NO: 12; and/or
 (b) a VL CDR2 comprising the amino acid sequence of SEQ ID NO: 7; and/or
 (c) a VL CDR3 comprising the amino acid sequence of SEQ ID NO: 15.

In some aspects, the anti-L1CAM antibody or antigen-binding fragment thereof, which specifically binds to human L1CAM, comprise:
 (a) a VH CDR1 comprising the amino acid sequence of SEQ ID NO: 2;
 (b) a VH CDR2 comprising the amino acid sequence of SEQ ID NO: 10;
 (c) a VH CDR3 comprising the amino acid sequence of SEQ ID NO: 4;
 (d) a VL CDR1 comprising the amino acid sequence of SEQ ID NO: 12;
 (e) a VL CDR2 comprising the amino acid sequence of SEQ ID NO: 7; and/or
 (f) a VL CDR3 comprising the amino acid sequence of SEQ ID NO: 15.

In some aspects, the anti-L1CAM antibody or antigen-binding fragment thereof, which specifically binds to human L1CAM, comprises:
 (a) a VL CDR1 comprising the amino acid sequence of SEQ ID NO: 12; and/or
 (b) a VL CDR2 comprising the amino acid sequence of SEQ ID NO: 7; and/or
 (c) a VL CDR3 comprising the amino acid sequence of SEQ ID NO: 17.

In some aspects, the anti-L1CAM antibody or antigen-binding fragment thereof, which specifically binds to human L1CAM, comprise:
 (a) a VH CDR1 comprising the amino acid sequence of SEQ ID NO: 2;
 (b) a VH CDR2 comprising the amino acid sequence of SEQ ID NO: 10;
 (c) a VH CDR3 comprising the amino acid sequence of SEQ ID NO: 4;
 (d) a VL CDR1 comprising the amino acid sequence of SEQ ID NO: 12;
 (e) a VL CDR2 comprising the amino acid sequence of SEQ ID NO: 7; and/or
 (f) a VL CDR3 comprising the amino acid sequence of SEQ ID NO: 17.

In some aspects, the anti-L1CAM antibody or antigen-binding fragment thereof, which specifically binds to human L1CAM, comprises:
 (a) a VL CDR1 comprising the amino acid sequence of SEQ ID NO: 12; and/or
 (b) a VL CDR2 comprising the amino acid sequence of SEQ ID NO: 7; and/or
 (c) a VL CDR3 comprising the amino acid sequence of SEQ ID NO: 19.

In some aspects, the anti-L1CAM antibody or antigen-binding fragment thereof, which specifically binds to human L1CAM, comprise:
 (a) a VH CDR1 comprising the amino acid sequence of SEQ ID NO: 2;
 (b) a VH CDR2 comprising the amino acid sequence of SEQ ID NO: 10;
 (c) a VH CDR3 comprising the amino acid sequence of SEQ ID NO: 4;
 (d) a VL CDR1 comprising the amino acid sequence of SEQ ID NO: 12;
 (e) a VL CDR2 comprising the amino acid sequence of SEQ ID NO: 7; and/or
 (f) a VL CDR3 comprising the amino acid sequence of SEQ ID NO: 21.

In some aspects, the anti-L1CAM antibody or antigen-binding fragment thereof, which specifically binds to human L1CAM, comprise a heavy chain (HC) and a light chain (LC), wherein the HC of the antibody or antigen-binding fragment thereof comprises SEQ ID NO: 38 and the LC of the antibody or antigen-binding fragment thereof comprises SEQ ID NO: 39

In some aspects, the anti-L1CAM antibody or antigen-binding fragment thereof, which specifically binds to human L1CAM, comprise a heavy chain (HC) and a light chain (LC), wherein the HC of the antibody or antigen-binding fragment thereof comprises SEQ ID NO: 40 and the LC of the antibody or antigen-binding fragment thereof comprises SEQ ID NO: 41

In some aspects, the anti-L1CAM antibody or antigen-binding fragment thereof, which specifically binds to human L1CAM, comprise a heavy chain (HC) and a light chain (LC), wherein the HC of the antibody or antigen-binding fragment thereof comprises SEQ ID NO: 42 and the LC of the antibody or antigen-binding fragment thereof comprises SEQ ID NO: 0.43

In some aspects, the anti-L1CAM antibody or antigen-binding fragment thereof, which specifically binds to human L1CAM, comprise a heavy chain (HC) and a light chain (LC), wherein the HC of the antibody or antigen-binding fragment thereof comprises SEQ ID NO: 44 and the LC of the antibody or antigen-binding fragment thereof comprises SEQ ID NO: 0.45

In some aspects, the anti-L1CAM antibody or antigen-binding fragment thereof, which specifically binds to human L1 CAM, comprise a heavy chain (HC) and a light chain (LC), wherein the HC of the antibody or antigen-binding fragment thereof comprises SEQ ID NO: 46 and the LC of the antibody or antigen-binding fragment thereof comprises SEQ ID NO: 20.

TABLE 5A

Heavy Chain amino acid sequence

| Antibody | Heavy Chain Amino Acid Sequence (SEQ ID NO) |
|---|---|
| Anti-L1CAM ("Ab612") | EVQLVESGGGVVQPGGSLRLSCAASGFTFSRFGMHWVRQAPGKGLEWVAFISNEGSNKYY ADSVKGRFTISRDNSANTLYLQMNSLRAEDTAVYYCARGRAYGSGSLFDPWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK (SEQ ID NO: 38) |
| Anti-L1CAM ("Ab4H5") | EVQLVESGGGVVQPGGSLRLSCAASGFTFSRFGMHWVRQAPGKGLEWVAFISNEGSNKYY ADSVKGRFTISRDNSANTLYLQMNSLRAEDTAVYYCARGRAYGSGSLFDPWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK (SEQ ID NO: 40) |
| Anti-L1CAM ("Ab2C2") | EVQLVESGGGVVQPGGSLRLSCAASGFTFSRFGMHWVRQAPGKGLEWVAFISNEGSNKYY ADSVKGRFTISRDNSANTLYLQMNSLRAEDTAVYYCARGRAYGSGSLFDPWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK (SEQ ID NO: 42) |
| Anti-L1CAM ("Ab4H6") | EVQLVESGGGVVQPGGSLRLSCAASGFTFSRFGMHWVRQAPGKGLEWVAFISNEGSNKYY ADSVKGRFTISRDNSANTLYLQMNSLRAEDTAVYYCARGRAYGSGSLFDPWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK (SEQ ID NO: 44) |
| Anti-L1CAM ("Ab5D12") | EVQLVESGGGVVQPGGSLRLSCAASGFTFSRFGMHWVRQAPGKGLEWVAFISNEGSNKYY ADSVKGRFTISRDNSANTLYLQMNSLRAEDTAVYYCARGRAYGSGSLFDPWGQGTLVTVS SASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREPQVYTLPPSRD ELTKNQVSLTCLVKGFYPSDIAVEWESNGQPENNYKTTPPVLDSDGSFFLYSKLTVDKSR WQQGNVFSCSVMHEALHNHYTQKSLSLSPGK (SEQ ID NO: 46) |

TABLE 5B

Light Chain amino acid sequence

| Antibody | Light Chain Amino Acid Sequence (SEQ ID NO) |
|---|---|
| Anti-L1CAM ("Ab612") | DIQL TQSPSS LSASVGDRVT ITCRASRTIS SYVNWYRQRP GKAPESLIYA ASNLHSGVPS RFSGSGSGTD FTLTISSLQP EDFATYYCQQ SIGRGPVTFGQ GTKLEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFN RGEC (SEQ ID NO: 39) |
| Anti-L1CAM ("Ab4H5") | DIQL TQSPSS LSASVGDRVT ITCRASRTIS SYVNWYRQRP GKAPESLIYA ASNLHSGVPS RFSGSGSGTD FTLTISSLQP EDFATYYCQQ AGFYTPWTFG QGTKLEIK TVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVTKSFN RGEC (SEQ ID NO: 41) |
| Anti-L1CAM ("Ab2C2") | DIQL TQSPSS LSASVGDRVT ITCRASRTIS SYVNWYRQRP GKAPESLIYA ASNLHSGVPS RFSGSGSGTD FTLTISSLQP EDFATYYCQQ AGFYSPWTFG QGTKLEIK RTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKS FNRGEC (SEQ ID NO: 43) |
| Anti-L1CAM ("Ab4H6") | DIQL TQSPSS LSASVGDRVT ITCRASRTIS SYVNWYRQRP GKAPESLIYA ASNLHSGVPS RFSGSGSGTD FTLTISSLQP EDFATYYC QQSLHFYPWT FG QGTKLEIK RTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKS FNRGEC (SEQ ID NO: 45) |
| Anti-L1CAM ("Ab5D12") | DIQL TQSPSS LSASVGDRVT ITCRASRTIS SYVNWYRQRP GKAPESLIYA ASNLHSGVPS RFSGSGSGTD FTLTISSLQP EDFATYYC QQSLVWYPWT FG QGTKLEIK RTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPVTKS FNRGEC (SEQ ID NO: 20) |

A VH domain, or one or more CDRs thereof, described herein can be linked to a constant domain for forming a heavy chain, e.g., a full length heavy chain. Similarly, a VL domain, or one or more CDRs thereof, described herein can be linked to a constant domain for forming a light chain, e.g., a full length light chain. A full length heavy chain and full length light chain combine to form a full length antibody.

Accordingly, in specific aspects, provided herein is an antibody comprising an antibody light chain and heavy chain, e.g., a separate light chain and heavy chain. With respect to the light chain, in a specific aspect, the light chain of an antibody described herein is a kappa light chain. In another specific aspect, the light chain of an antibody described herein is a lambda light chain. In yet another specific aspect, the light chain of an antibody described herein is a human kappa light chain or a human lambda light chain. In a particular aspect, an antibody described herein, which specifically binds to an L1CAM polypeptide (e.g., human L1CAM) comprises a light chain which comprises any VL or VL CDR amino acid sequences described herein, and wherein the constant region of the light chain comprises the amino acid sequence of a human kappa light chain constant region. In a particular aspect, an antibody described herein, which specifically binds to an L1CAM polypeptide (e.g., human L1CAM) comprises a light chain which comprises a VL or VL CDR amino acid sequences described herein, and wherein the constant region of the light chain comprises the amino acid sequence of a human lambda light chain constant region. Non-limiting examples of human constant region sequences have been described in the art, e.g., see U.S. Pat. No. 5,693,780 and Kabat E A et al, (1991) supra.

With respect to the heavy chain, in some aspects, the heavy chain of an antibody described herein can be an alpha (α), delta (δ), epsilon (ε), gamma (γ) or mu (μ) heavy chain. In another specific aspect, the heavy chain of an antibody described can comprise a human alpha (a), delta (δ), epsilon (ε), gamma (γ) or mu (μ) heavy chain. In one aspect, an antibody described herein, which specifically binds to L1CAM (e.g., human L1CAM), comprises a heavy chain which comprises a VH or VH CDR amino acid sequence described herein, and wherein the constant region of the heavy chain comprises the amino acid sequence of a human gamma (γ) heavy chain constant region. In another aspect, an antibody described herein, which specifically binds to L1CAM (e.g., human L1CAM), comprises a heavy chain which comprises a VH or VH CDR amino acid sequence disclosed herein, and wherein the constant region of the heavy chain comprises the amino acid of a human heavy chain described herein or known in the art. Non-limiting examples of human constant region sequences have been described in the art, e.g., see U.S. Pat. No. 5,693,780 and Kabat E A et al., (1991) supra.

In some aspects, an antibody described herein, which specifically binds to L1CAM (e.g., human L1CAM) comprises a VL domain and a VH domain comprising the VH or VH CDRs and VL and VL CDRs described herein, and wherein the constant regions comprise the amino acid sequences of the constant regions of an IgG, IgE, IgM, IgD, IgA or IgY immunoglobulin molecule, or a human IgG, IgE, IgM, IgD, IgA or IgY immunoglobulin molecule. In another specific aspect, an antibody described herein, which specifically binds to L1CAM (e.g., human L1CAM) comprises a VL domain and a VH domain comprising any amino acid sequences described herein, and wherein the constant regions comprise the amino acid sequences of the constant regions of an IgG, IgE, IgM, IgD, IgA or IgY immunoglobulin molecule, any subclass (e.g., IgG1, IgG2, IgG3, IgG4, IgA1 and IgA2) of immunoglobulin molecule. In some aspects, the constant regions comprise the amino acid sequences of the constant regions of a human IgG, which are naturally-occurring, including subclasses (e.g., IgG1, IgG2, IgG3 or IgG4), and allotypes (e.g., G1m, G2m, G3m, and nG4m) and variants thereof. See, e.g., Vidarsson G. et al. *Front Immunol.* 5:520 (published online Oct. 20, 2014) and Jefferis R. and Lefranc M P, mAbs 1:4, 1-7(2009). In some aspects, the constant regions comprise the amino acid sequences of the constant regions of a human IgG1, IgG2, IgG3, or IgG4, or variants thereof.

In certain aspects, the anti-L1CAM antibody or antigen-binding fragment thereof disclosed herein does not have Fc effector functions, e.g., complement-dependent cytotoxicity (CDC) and/or antibody-dependent cellular phagocytosis (ADCP). Effector functions are mediated by the Fc region and the residues most proximal to the hinge region in the CH2 domain of the Fc region are responsible for effector functions of antibodies as it contains a largely overlapping binding site for C1q (complement) and IgG-Fc receptors (FcγR) on effector cells of the innate immune system. Also, IgG2 and IgG4 antibodies have lower levels of Fc effector functions than IgG1 and IgG3 antibodies. Effector functions of an antibody can be reduced or avoided by different approaches known in the art, including (1) using antibody fragments lacking the Fc region (e.g., such as a Fab, F(ab')$_2$, single chain Fv (scFv), or a sdAb consisting of a monomeric VH or VL domain); (2) generating aglycosylated antibodies, which can be generated by, for example, deleting or altering the residue the sugar is attached to, removing the sugars enzymatically, producing the antibody in cells cultured in the presence of a glycosylation inhibitor, or by expressing the antibody in cells unable to glycosylate proteins (e.g., bacterial host cells, see, e.g., U.S. Pub. No. 20120100140); (3) employing Fc regions from an IgG subclass that have reduced effector function (e.g., an Fc region from IgG2 or IgG4 antibodies or a chimeric Fc region comprising a CH2 domain from IgG2 or IgG4 antibodies, see, e.g., U.S. Pub. No. 20120100140 and Lau C. et al. *J. Immunol.* 191:4769-4777 (2013)); and (4) generating an Fc region with mutations that result in reduced or no Fc functions. See, e.g., U.S. Pub. No. 20120100140 and U.S. and PCT applications cited therein and An et al., mAbs 1:6, 572-579 (2009).

Thus, in some aspects, the anti-L1CAM antibody or antigen-binding fragment thereof disclosed herein is a Fab, a Fab', a F(ab')2, a Fv, a single chain Fv (scFv), or a sdAb consisting of a monomeric VH or VL domain. Such antibody fragments are well known in the art and are described supra.

In some aspects, the anti-L1CAM antibody or antigen-binding fragment thereof disclosed herein comprises an Fc region with reduced or no Fc effector function. In some aspects, the constant regions comprise the amino acid sequences of the Fc region of a human IgG2 or IgG4, in some aspects, the anti-L1CAM antibody is of an IgG2/IgG4 isotype. In some aspects, the anti-L1CAM antibody comprises a chimeric Fc region which comprises a CH2 domain from an IgG antibody of the IgG4 isotype and a CH3 domain from an IgG antibody of the IgG1 isotype, or a chimeric Fc region which comprises a hinge region from IgG2 and a CH2 region from IgG4, or an Fc region with mutations that result in reduced or no Fc functions. Fc regions with reduced or no Fc effector function include those known in the art. See, e.g., Lau C. et al. *J. Immunol.* 191:4769-4777 (2013); An et al., mAbs 1:6, 572-579 (2009); and U.S. Pub. No. 20120100140 and the U.S. patents and publications and PCT publications cited therein. Also Fc regions with reduced or no Fc effector function can be readily made by a person of ordinary skill in the art.

IV. Nucleic Acid Molecules

Another aspect described herein pertains to one or more nucleic acid molecules that encode any one of the antibodies or antigen-binding fragments thereof described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) *Current Protocols in Molecular Biology, Greene Publishing and* Wiley Interscience, New York. A nucleic acid described herein can be, for example, DNA or RNA and can or cannot contain intronic sequences. In a certain aspects, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Certain nucleic acids molecules described herein are those encoding the VH and VL sequences of the Ab612, Ab4H5, Ab2C2, Ab4H6, Ab5D12 monoclonal antibody. Exemplary DNA sequences encoding the VH sequence of Ab612, Ab4H5, Ab2C2, Ab4H6, Ab5D12 are set forth in SEQ ID NOs: 8, 14, 16, 18, or 22. Exemplary DNA sequences encoding the VL sequences of Ab612, Ab4H5, Ab2C2, Ab4H6, Ab5D12 are set forth in SEQ ID NOs: 33, 34, 35, 36, and 37, respectively.

TABLE 6

Variable heavy chain polynucleotide sequence

| Antibody | Variable Heavy Chain Polynucleotide Sequence (SEQ ID NO) |
| --- | --- |
| Anti-L1CAM ("Ab612") | gaggtgcagctggtggagagcggcggcggcgtggtgcagcccggcggcagcctgagactgagctgcgccgcca gcggcttcaccttcagcagattcggcatgcactgggtgagacaggcccccggcaagggcctggagtgggtggcctt catcagcaacgagggcagcaacaagtactacgccgacagcgtgaagggcagattcaccatcagcagagacaaca gcgccaacaccctgtacctgcagatgaacagcctgagagccgaggacaccgccgtgtactactgcgccagaggca gagcctacggcagcggcagcctgttcgacccctggggccagggcaccctggtgaccgtgagcagc (SEQ ID NO: 8) |

TABLE 6-continued

Variable heavy chain polynucleotide sequence

| Antibody | Variable Heavy Chain Polynucleotide Sequence (SEQ ID NO) |
|---|---|
| Anti-L1CAM ("Ab4H5") | gaggtgcagctggtggagagcggcggcggcgtggtgcagcccggcggcagcctgagactgagctgcgccgca gcggcttcaccttcagcagattcggcatgcactgggtgagacaggcccccggcaagggcctggagtgggtggcctt catcagcaacgagggcagcaacaagtactacgccgacagcgtgaagggcagattcaccatcagcagagacaaca gcgccaacaccctgtacctgcagatgaacagcctgagagccgaggacaccgccgtgtactactgcgccagaggca gagcctacggcagcggcagcctgttcgacccctggggccagggcaccctggtgaccgtgagcagc (SEQ ID NO: 14) |
| Anti-L1CAM ("Ab2C2") | gaggtgcagctggtggagagcggcggcggcgtggtgcagcccggcggcagcctgagactgagctgcgccgca gcggcttcaccttcagcagattcggcatgcactgggtgagacaggcccccggcaagggcctggagtgggtggcctt catcagcaacgagggcagcaacaagtactacgccgacagcgtgaagggcagattcaccatcagcagagacaaca gcgccaacaccctgtacctgcagatgaacagcctgagagccgaggacaccgccgtgtactactgcgccagaggca gagcctacggcagcggcagcctgttcgacccctggggccagggcaccctggtgaccgtgagcagc (SEQ ID NO: 16) |
| Anti-L1CAM ("Ab4H6") | gaggtgcagctggtggagagcggcggcggcgtggtgcagcccggcggcagcctgagactgagctgcgccgca gcggcttcaccttcagcagattcggcatgcactgggtgagacaggcccccggcaagggcctggagtgggtggcctt catcagcaacgagggcagcaacaagtactacgccgacagcgtgaagggcagattcaccatcagcagagacaaca gcgccaacaccctgtacctgcagatgaacagcctgagagccgaggacaccgccgtgtactactgcgccagaggca gagcctacggcagcggcagcctgttcgacccctggggccagggcaccctggtgaccgtgagcagc (SEQ ID NO: 18) |
| Anti-L1CAM ("Ab5D12") | gaggtgcagctggtggagagcggcggcggcgtggtgcagcccggcggcagcctgagactgagctgcgccgca gcggcttcaccttcagcagattcggcatgcactgggtgagacaggcccccggcaagggcctggagtgggtggcctt catcagcaacgagggcagcaacaagtactacgccgacagcgtgaagggcagattcaccatcagcagagacaaca gcgccaacaccctgtacctgcagatgaacagcctgagagccgaggacaccgccgtgtactactgcgccagaggca gagcctacggcagcggcagcctgttcgacccctggggccagggcaccctggtgaccgtgagcagc (SEQ ID NO: 22) |

TABLE 7

Variable light chain polynucleotide sequence

| Antibody | Variable Light Chain Polynucleotide Sequence (SEQ ID NO) |
|---|---|
| Anti-L1CAM ("Ab612") | GACATCCAGCTGACCCAGAGCCCCAGCAGCCTGAGCGCCAGCGTGGGCGACA GAGTGACCATCACCTGCAGAGCCAGCAGAACCATCAGCAGCTACGTGAACTG GTACAGACAGAGACCCGGCAAGGCCCCCGAGAGCCTGATCTACGCCGCCAGC AACCTGCACAGCGGCGTGCCCAGCAGATTTAGCGGCAGCGGCAGCGGCACCG ACTTCACCCTGACCATCAGCAGCCTGCAGCCCGAGGACTTCGCCACCTACTAC TGCCAGCAGAGCATCGGCAGAGGCCCCGTGACCTTCGGCCAGGGCACCAAGC TGGAGATCAAG (SEQ ID NO: 33) |
| Anti-L1CAM ("Ab4H5") | GACATCCAGCTGACCCAGAGCCCCAGCAGCCTGAGCGCCAGCGTGGGCGACA GAGTGACCATCACCTGCAGAGCCAGCAGAACCATCAGCAGCTACGTGAACTG GTACAGACAGAGACCCGGCAAGGCCCCCGAGAGCCTGATCTACGCCGCCAGC AACCTGCACAGCGGCGTGCCCAGCAGATTTAGCGGCAGCGGCAGCGGCACCG ACTTCACCCTGACCATCAGCAGCCTGCAGCCCGAGGACTTCGCCACCTACTAC TGCCAGCAGGCCGGCTTCTACACCCCCTGGACCTTCGGCCAGGGCACCAAGCT GGAGATCAAG (SEQ ID NO: 34) |
| Anti-L1CAM ("Ab2C2") | GACATCCAGCTGACCCAGAGCCCCAGCAGCCTGAGCGCCAGCGTGGGCGACA GAGTGACCATCACCTGCAGAGCCAGCAGAACCATCAGCAGCTACGTGAACTG GTACAGACAGAGACCCGGCAAGGCCCCCGAGAGCCTGATCTACGCCGCCAGC AACCTGCACAGCGGCGTGCCCAGCAGATTTAGCGGCAGCGGCAGCGGCACCG ACTTCACCCTGACCATCAGCAGCCTGCAGCCCGAGGACTTCGCCACCTACTAC TGCCAGCAGGCCGGCTTCTACTCCCCCTGGACCTTCGGCCAGGGCACCAAGCT GGAGATCAAG (SEQ ID NO: 35) |
| Anti-L1CAM ("Ab4H6") | GACATCCAGCTGACCCAGAGCCCCAGCAGCCTGAGCGCCAGCGTGGGCGACA GAGTGACCATCACCTGCAGAGCCAGCAGAACCATCAGCAGCTACGTGAACTG GTACAGACAGAGACCCGGCAAGGCCCCCGAGAGCCTGATCTACGCCGCCAGC AACCTGCACAGCGGCGTGCCCAGCAGATTTAGCGGCAGCGGCAGCGGCACCG ACTTCACCCTGACCATCAGCAGCCTGCAGCCCGAGGACTTCGCCACCTACTAC TGCCAGCAGTCCCTGCACTTCTACCCCTGGACCTTCGGCCAGGGCACCAAGCT GGAGATCAAG (SEQ ID NO: 36) |

TABLE 7-continued

Variable light chain polynucleotide sequence

| Antibody | Variable Light Chain Polynucleotide Sequence (SEQ ID NO) |
|---|---|
| Anti-L1CAM ("Ab5D12") | GACATCCAGCTGACCCAGAGCCCCAGCAGCCTGAGCGCCAGCGTGGGCGACA GAGTGACCATCACCTGCAGAGCCAGCAGAACCATCAGCAGCTACGTGAACTG GTACAGACAGAGACCCGGCAAGGCCCCGAGAGCCTGATCTACGCCGCCAGC AACCTGCACAGCGGCGTGCCCAGCAGATTTAGCGGCAGCGGCAGCGGCACCG ACTTCACCCTGACCATCAGCAGCCTGCAGCCCGAGGACTTCGCCACCTACTAC TGCCAGCAGTCCCTGGTGTGGTACCCCTGGACCTTCGGCCAGGGCACCAAGCT GGAGATCAAG (SEQ ID NO: 37) |

A method for making an anti-L1CAM antibody as disclosed herein can comprise expressing the heavy chain and the light chains in a cell line comprising the nucleotide sequences encoding the heavy and light chains with a signal peptide. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2, and/or CH3). The sequences of human heavy chain constant region genes are known in the art (see, e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM, or IgD constant region, for example, an IgG2 and/or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al., (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly4-Ser)3, such that the VH and VL sequences can be expressed as a contiguous single-chain protein, with the VL and VH regions joined by the flexible linker (see, e.g., Bird et al., (1988) Science 242:423-426; Huston et al., (1988) Proc. Natl. Acad. Sci. USA 85:5879-5883; McCafferty et al., (1990) Nature 348:552-554).

In some aspects, the present disclosure provides a vector comprising an isolated nucleic acid molecule comprising a nucleotide sequence encoding an antibody or antigen-binding fragment thereof. In other aspects, the vectors can be used for gene therapy.

Suitable vectors for the disclosure include expression vectors, viral vectors, and plasmid vectors. In one aspect, the vector is a viral vector.

As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Expression vectors of the disclosure can include polynucleotides encoding the antibody or antigen-binding fragment thereof described herein. In one aspect, the coding sequences for the antibody or antigen-binding fragment thereof are operably linked to an expression control sequence. As used herein, two nucleic acid sequences are operably linked when they are covalently linked in such a way as to permit each component nucleic acid sequence to retain its functionality. A coding sequence and a gene expression control sequence are said to be operably linked when they are covalently linked in such a way as to place the expression or transcription and/or translation of the coding sequence under the influence or control of the gene expression control sequence. Two DNA sequences are said to be operably linked if induction of a promoter in the 5' gene expression sequence results in the transcription of the coding sequence and if the nature of the linkage between the two DNA sequences does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a gene expression sequence would be operably linked to a coding nucleic acid sequence if the gene expression sequence were capable of effecting transcription of that coding nucleic acid sequence such that the resulting transcript is translated into the desired antibody or antigen-binding fragment thereof.

Viral vectors include, but are not limited to, nucleic acid sequences from the following viruses: retrovirus, such as Moloney murine leukemia virus, Harvey murine sarcoma virus, murine mammary tumor virus, and Rous sarcoma virus; lentivirus; adenovirus; adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, *A Laboratory Manual*, W. H. Freeman Co., New York (1990) and Murry, E. J., Methods in Molecular Biology, Vol. 7, Humana Press, Inc., Cliffton, N. J. (1991).

In one aspect, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In other aspects, the vector is derived from lentivirus. In certain aspects, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The disclosure provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some aspects, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G) of hepatitis viruses and of influenza also can be used.

The vector providing the viral env nucleic acid sequence is associated operably with regulatory sequences described elsewhere herein.

Examples of the lentiviral vectors are disclosed in WO9931251, WO9712622, WO9817815, WO9817816, and WO9818934, which are incorporated herein by reference in their entireties.

Other vectors include plasmid vectors. Plasmid vectors have been extensively described in the art and are well-known to those of skill in the art. See, e.g., Sambrook et al., *Molecular Cloning: A Laboratory Manual*, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA.). Other plasmids are well-known to those of ordinary skill in the art. Additionally, plasmids can be custom designed using standard molecular biology techniques to remove and/or add specific fragments of DNA.

V. Antibody Production

Antibodies or fragments thereof that immunospecifically bind to L1CAM (e.g., human L1CAM) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) *Molecular Cloning: A Laboratory Manual*, Cold Spring Harbor Laboratory Press; Sambrook J et al., (1989), *Molecular Cloning: A Laboratory Manual*, Second Edition, Cold Spring Harbor Laboratory Press; Sambrook J et al., (2001) *Molecular Cloning: A Laboratory Manual*, Cold Spring Harbor Laboratory Press, Cold Spring Harbor, NY; Ausubel F M et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren B et al., (eds.) (1999) *Genome Analysis: A Laboratory Manual*, Cold Spring Harbor Laboratory Press.

In a specific aspect, an antibody described herein is an antibody (e.g., monoloclonal antibody) prepared, expressed, created or isolated by any means that involves creation, e.g., via synthesis, genetic engineering of DNA sequences. In certain aspects, such antibody comprises sequences (e.g., DNA sequences or amino acid sequences) that do not naturally exist within the antibody germline repertoire of an animal or mammal (e.g., human) in vivo.

In a certain aspect, provided herein is a method of making an antibody or an antigen-binding fragment thereof which immunospecifically binds to L1CAM (e.g., human L1CAM) comprising culturing a cell or host cell described herein. In a certain aspect, provided herein is a method of making an antibody or an antigen-binding fragment thereof which immunospecifically binds to L1CAM (e.g., human L1CAM) comprising expressing (e.g., recombinantly expressing) the antibody or antigen-binding fragment thereof using a cell or host cell described herein (e.g., a cell or a host cell comprising polynucleotides encoding an antibody described herein). In a particular aspect, the cell is an isolated cell. In a particular aspect, the exogenous polynucleotides have been introduced into the cell. In a particular aspect, the method further comprises the step of purifying the antibody or antigen-binding fragment thereof obtained from the cell or host cell.

Methods for producing polyclonal antibodies are known in the art (see, for example, Chapter 11 in: Short Protocols in Molecular Biology, (2002) 5th Ed., Ausubel F M et al., eds., *John Wiley and Sons*, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, *Antibodies: A Laboratory Manual*, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific aspects, a "monoclonal antibody," as used herein, is an antibody produced by a single cell (e.g., hybridoma or host cell producing a recombinant antibody), wherein the antibody immunospecifically binds to L1CAM (e.g., human L1CAM) as determined, e.g., by ELISA or other antigen-binding or competitive binding assay known in the art or in the Examples provided herein. In particular aspects, a monoclonal antibody can be a chimeric antibody or a humanized antibody. In certain aspects, a monoclonal antibody is a monovalent antibody or multivalent (e.g., bivalent) antibody. In particular aspects, a monoclonal antibody is a monospecific or multispecific antibody (e.g., bispecific antibody). Monoclonal antibodies described herein can, for example, be made by the hybridoma method as described in Kohler G & Milstein C (1975) *Nature* 256: 495 or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., human L1CAM) used for immunization. Alternatively, lymphocytes can be immunized in vitro. Lymphocytes then are fused with myeloma cells using a suitable fusing agent, such as polyethylene glycol, to form a hybridoma cell (Goding J W (Ed), *Monoclonal Antibodies: Principles and Practice*, pp. 59-103 (Academic Press, 1986)). Additionally, a RIMMS (repetitive immunization multiple sites) technique can be used to immunize an animal (Kilpatrick K E et al., (1997) *Hybridoma* 16:381-9, incorporated by reference in its entirety).

In some aspects, mice (or other animals, such as chickens, rats, monkeys, donkeys, pigs, sheep, hamster, or dogs) can be immunized with an antigen (e.g., L1CAM such as human L1CAM) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC) (Manassas, VA), to form hybridomas. Hybridomas are selected and cloned by limited dilution. In certain aspects, lymph nodes of the immunized mice are harvested and fused with NSO myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific aspects employ myeloma cells that fuse efficiently, support stable high-level production of antibody by the selected antibody-producing cells, and are sensitive to a medium such as HAT medium. Among these myeloma cell lines are murine myeloma lines, such as NSO cell line or those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor D (1984) *J Immunol* 133: 3001-5; Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against L1CAM (e.g., human L1CAM). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding J W (Ed), *Monoclonal Antibodies: Principles and Practice*, supra). Suitable culture media for this purpose include, for example, D-MEM or RPMI 1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific L1CAM (e.g., human L1CAM) and can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of an antibody molecule and contains the complete light chain paired with the VH and CH1 domains of the heavy chain. A F(ab')2 fragment contains the two antigen-binding arms of an antibody molecule linked by disulfide bonds in the hinge region.

In one aspect, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different fragments of the antibody are derived from different immunoglobulin molecules. For example, a chimeric antibody can contain a variable region of a non-human animal (e.g., mouse, rat or chicken) monoclonal antibody fused to a constant region of a human antibody. Methods for producing chimeric antibodies are known in the art. See, e.g., Morrison S L (1985) *Science* 229: 1202-7; Oi V T & Morrison S L (1986) *BioTechniques* 4: 214-221; Gillies S D et al., (1989) *J Immunol Methods* 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine or a chicken immunoglobulin). In particular aspects, a humanized antibody also comprises at least a fragment of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA, and IgE, and any isotype, including IgG1, IgG2, IgG3, and IgG4. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) *Mol Immunol* 28(4/5): 489-498; Studnicka G M et al., (1994) *Prot Engineering* 7(6): 805-814; and Roguska M A et al., (1994) *PNAS* 91: 969-973), chain shuffling (U.S. Pat. No. 5,565,332), and techniques disclosed in, e.g., U.S. Pat. No. 6,407,213, U.S. Pat. No. International Publication No. WO 93/17105; Tan P et al., (2002) *J Immunol* 169: 1119-25; Caldas C et al., (2000) *Protein Eng.* 13(5): 353-60; Morea V et al., (2000) *Methods* 267-79; Baca M et al., (1997) *J Biol Chem* 272(16): 10678-84; Roguska M A et al., (1996) *Protein Eng* 9(10): 895 904; Couto J R et al., (1995) *Cancer Res.* 55 (23 Supp): 5973s-5977s; Couto J R et al., (1995) *Cancer Res* 55(8): 1717-22; Sandhu J S (1994) *Gene* 150(2): 409-10 and Pedersen J T et al., (1994) *J Mol Biol* 235(3): 959-73. See also U.S. Application Publication No. US 2005/0042664 A1 (Feb. 24, 2005), which is incorporated by reference herein in its entirety.

Methods for making multispecific (e.g., bispecific antibodies) have been described. See, for example, U.S. Pat. Nos. 7,951,917; 7,183,076; 8,227,577; 5,837,242; 5,869,620; 6,132,992 and 8,586,713.

Single domain antibodies, for example, antibodies lacking the light chains, can be produced by methods well known in the art. See Riechmann L & Muyldermans S (1999) *J Immunol* 231: 25-38; Nuttall S D et al., (2000) *Curr Pharm Biotechnol* 1(3): 253-263; Muyldermans S, (2001) *J Biotechnol* 74(4): 277-302; U.S. Pat. No. 6,005,079; and International Publication Nos. WO 94/04678, WO 94/25591 and WO 01/44301.

Further, antibodies that immunospecifically bind to a L1CAM antigen can, in turn, be utilized to generate anti-idiotype antibodies that "mimic" an antigen using techniques well known to those skilled in the art. (See, e.g., Greenspan N S & Bona C A (1989) *FASEB J* 7(5): 437-444; and Nissinoff A (1991) *J Immunol* 147(8): 2429-2438).

In particular aspects, an antibody described herein, which binds to the same epitope of L1CAM (e.g., human L1CAM) as an anti-L1CAM antibody described herein, is a human antibody or an antigen-binding fragment thereof. In particular aspects, an antibody described herein, which competitively blocks (e.g., in a dose-dependent manner) antibodies described herein, (e.g., Ab612, Ab4H5, Ab2C2, Ab4H6, and Ab5D12) from binding to L1CAM (e.g., human L1CAM), is a human antibody or an antigen-binding fragment thereof.

Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a fragment of an antigen (e.g., L1CAM). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,569,825, 5,661,016, 5,545, 806, 5,814,318 and 5,939,598. Examples of mice capable of producing human antibodies include the XENOMOUSE™ (Abgenix, Inc.; U.S. Pat. Nos. 6,075,181 and 6,150,184), the HUAB-MOUSE™ (Mederex, Inc./Gen Pharm; U.S. Pat. Nos. and 5,569, 825), the TRANS CHROMO MOUSE™ (Kirin) and the KM MOUSE™ (Medarex/Kirin).

Human antibodies which specifically bind to L1CAM (e.g., human L1CAM) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some aspects, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that immunospecifically bind to a target antigen (e.g., L1CAM such as human L1CAM)). Such methods are known and are described in the art, see, e.g., Shinmoto H et al., (2004) Cytotechnology 46: 19-23; Naganawa Y et al., (2005) Human Antibodies 14: 27-31.

VI. Cells and Vectors

In certain aspects, provided herein are cells (e.g., host cells) expressing (e.g., recombinantly) antibodies described herein (or an antigen-binding fragment thereof) which specifically bind to L1CAM (e.g., human L1CAM) and related polynucleotides and expression vectors. Provided herein are vectors (e.g., expression vectors) comprising polynucleotides comprising nucleotide sequences encoding anti-L1CAM antibodies or a fragment for recombinant expression in host cells, e.g., in mammalian cells. Also provided herein are host cells comprising such vectors for recombinantly expressing anti-L1CAM antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to L1CAM (e.g., human L1CAM) involves construction of an expression vector containing a polynucleotide that encodes the antibody. Once a polynucleotide encoding an antibody molecule, heavy and/or light chain of an antibody, or a fragment thereof (e.g., heavy and/or light chain variable domains) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable domains of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein (e.g., an antibody comprising the VH and/or VL, or one or more of the VH and/or VL CDRs, of Ab612, Ab4H5, Ab2C2, Ab4H6, and Ab5D12) or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain aspects, for the expression of double-chained antibodies, vectors encoding both the heavy and light chains, individually, can be co-expressed in the host cell for expression of the entire immunoglobulin molecule, as detailed below. In certain aspects, a host cell contains a vector comprising a polynucleotide encoding both the heavy chain and light chain of an antibody described herein, or a fragment thereof. In specific aspects, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other aspects, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific aspects, a heavy chain/heavy chain variable region expressed by a first cell associated with a light chain/light chain variable region of a second cell to form an anti-L1CAM antibody described herein or an antigen-binding fragment thereof. In certain aspects, provided herein is a population of host cells comprising such first host cell and such second host cell.

In a particular aspect, provided herein is a population of vectors comprising a first vector comprising a polynucleotide encoding a light chain/light chain variable region of an anti-L1CAM antibody described herein, and a second vector comprising a polynucleotide encoding a heavy chain/heavy chain variable region of an anti-L1CAM antibody described herein.

A variety of host-expression vector systems can be utilized to express antibody molecules described herein. Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NSO, PER.C6, VERO, CRL7030, HsS78Bst, HeLa, NIH 3T3, HEK-293T, HepG2, SP210, R1.1, B-W, L-M, BSC1, BSC40, YB/20, SP2/0, Sf9, human lymphoblastoid, NSO, bow melanoma, HT-1080, PERC.6, and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific aspect, cells for expressing antibodies described herein or an antigen-binding fragment thereof are CHO cells, for example CHO cells from the CHO GS SYSTEM' (Lonza). In a particular aspect, cells for expressing antibodies described herein are human cells, e.g., human cell lines. In a specific aspect, a mammalian expression vector is POPTIVEC™ or pcDNA3.3. In a particular aspect, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) *Gene* 45: 101-5; and Cockett M I et al., (1990) *Biotechnology* 8(7): 662-7). In certain aspects, antibodies described herein are produced by CHO cells or NSO cells. In a specific aspect, the expression of nucleotide sequences encoding antibodies described herein which immunospecifically bind L1CAM (e.g., human L1CAM) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) *EMBO J* 2: 1791-1794), in which the antibody coding sequence can be ligated individually into the vector in frame with the lac Z coding region so that a fusion protein is produced; pIN vectors (Inouye S & Inouye M (1985) *Nuc Acids Res* 13: 3101-3109; Van Heeke G & Schuster S M (1989) *J Blot Chem* 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) *PNAS* 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) *Methods Enzymol.* 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, SKOV-3, B16-F1, NCI-H522, VERO, BHK, Hela, MDCK, HEK 293, NIH 3T3, W138, BT483, Hs578T, HTB2, BT20 and T47D, NSO (a murine myeloma cell line that does not endogenously produce any immunoglobulin chains), CRL7030, COS (e.g., COS 1 or COS), PER.C6, VERO, HsS78Bst, HEK-293T, HepG2, SP210, R1. 1, B-W, L-M, BSC1, BSC40, YB/20, BMT10 and HsS78Bst cells. In certain aspects, anti-L1CAM antibodies described herein are produced in mammalian cells, such as CHO cells.

In a specific aspect, the antibodies described herein or antigen-binding fragments thereof have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of 1,6-fucosyltransferase can be used to produce antibodies or antigen-binding fragments thereof with reduced fucose content. The POTELLIGENT® system (Lonza) is an example of such a system that can be used to produce antibodies or antigen-binding fragments thereof with reduced fucose content.

For long-term, high-yield production of recombinant proteins, stable expression cells can be generated. For example, cell lines which stably express an anti-L1CAM antibody described herein an antigen-binding fragment thereof can be engineered. In specific aspects, a cell provided herein stably expresses a light chain/light chain variable domain and a heavy chain/heavy chain variable domain which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-L1CAM antibody described herein or an antibody binding fragment thereof. Such engineered cell lines can be particularly useful in screening and evaluation of compositions that interact directly or indirectly with the antibody molecule.

A number of selection systems can be used, including but not limited to, the herpes simplex virus thymidine kinase (Wigler M et al., (1977) *Cell* 11(1): 223-32), hypoxanthine-guanine phosphoribosyltransferase (Szybalska E H & Szybalski W (1962) *PNAS* 48(12): 2026-2034) and adenine phosphoribosyltransferase (Lowy I et al., (1980) *Cell* 22(3): 817-23) genes can be employed in tk-, hgprt- or aprt-cells, respectively. Also, antimetabolite resistance can be used as the basis of selection for the following genes: dhfr, which confers resistance to methotrexate (Wigler M et al., (1980) *PNAS* 77(6): 3567-70; O'Hare K et al., (1981) *PNAS* 78: 1527-31); gpt, which confers resistance to mycophenolic acid (Mulligan R C & Berg P (1981) *PNAS* 78(4): 2072-6); neo, which confers resistance to the aminoglycoside G-418 (Wu G Y & Wu C H (1991) *Biotherapy* 3: 87-95; Tolstoshev P (1993) *Ann Rev Pharmacol Toxicol* 32: 573-596; Mulligan R C (1993) *Science* 260: 926-932; and Morgan R A & Anderson W F (1993) *Ann Rev Biochem* 62: 191-217; Nabel G J & Feigner P L (1993) *Trends Biotechnol* 11(5): 211-5); and hygro, which confers resistance to hygromycin (Santerre R F et al., (1984) *Gene* 30(1-3): 147-56). Methods commonly known in the art of recombinant DNA technology can be routinely applied to select the desired recombinant clone and such methods are described, for example, in Ausubel F M et al., (eds.), *Current Protocols in Molecular Biology*, John Wiley & Sons, N Y (1993); Kriegler M, Gene Transfer and Expression, *A Laboratory Manual, Stockton Press, N Y* (1990); and in Chapters 12 and 13, Dracopoli N C et al., (eds.), *Current Protocols in Human Genetics*, John Wiley & Sons, N Y (1994); Colbere-Garapin F et al., (1981) *J Mot Blot* 150: 1-14, which are incorporated by reference herein in their entireties.

In some aspects, the antibody or antigen-binding fragment thereof of the present disclosure can be expressed on an immune cell, e.g., a T cell and/or an NK cell. In some aspects, the antibody or antigen-binding fragment thereof can be expressed as a chimeric antigen receptor (CAR). A CAR-T cell is a T cell that expresses a chimeric antigen receptor. The phrase "chimeric antigen receptor (CAR)," as used herein, refers to a recombinant fusion protein that has an antigen-specific extracellular (or ectodomain) domain coupled to an intracellular domain that directs the cell to perform a specialized function upon binding of an antigen to the extracellular domain. Chimeric antigen receptors are distinguished from other antigen binding agents by their ability to both bind WIC-independent antigen and transduce activation signals via their intracellular domain.

In some aspects, the antigen-specific extracellular domain of a chimeric antigen receptor recognizes and specifically binds an antigen, i.e., L1CAM. An L1CAM-specific extracellular domain suitable for use in a CAR of the present disclosure may be any antigen-binding polypeptide, a wide variety of which are known in the art. In some instances, the antigen-binding domain is a single chain Fv (scFv) or Fab. In other aspects, the antigen binding fragment useful for a CAR of the present disclosure includes an antigen-binding fragment disclosed anywhere herein.

In some aspects, the transmembrane domain useful for a CAR is connected to the extracellular domain and can include a naturally occurring transmembrane domain. In other aspects, the transmembrane domain useful for a CAR can be derived from alpha chain, beta chain, or zeta chain of T cell receptor, CD28, CD3 E, CD45, CD4, CD5, CDS, CD9, CD16, CD22, CD33, CD37, CD64, CD80, CD86, CD134, CD154, CD8, or any other known in the art.

The term "intracellular domain" refers to the portion of a CAR that transduces the effector function signal upon binding of an antigen to the extracellular domain and directs the T cell to perform a specialized function. In one aspect, an intracellular domain for a CAR comprises an immune receptor tyrosine-based activation motif activation motif (ITAM). In some aspects, the ITAM is derived from CD3 zeta (ζ, zeta), FcR gamma, FcR beta, CD3 gamma, CD3 delta, CD3 epsilon, CDS, CD22, CD79a, CD79b, CD66d, 4-1 BB, DAP-1 0, OX40, or Fc [epsilon] RI [gamma].

In some aspects, the CAR of the present disclosure further comprises a costimultatory domain that can be linked to the intracellular domain. The co-stimulatory domain in a CAR construct can transmit signals and activate the cells as a part of an intracellular portion of the CAR. In some aspects, the costimulatory domain is derived from CD27, CD28, 4-1BB, OX40, CD30, CD40, PD-1, ICOS, lymphocyte function-associated antigen-1 (LFA-1), CD7, LIGHT, NKG2C, or B7-H3.

In other aspects, a CAR of the present disclosure further comprises a linker. A short oligopeptide or polypeptide linker can be present between the transmembrane domain and the intracellular domain. In some aspects, the linker is not limited to a particular length as long as the intracellular domain of the CAR when the extracellular domain is bound to the antigen, i.e., L1CAM, is capable of inducing T cell activation. In some aspects, the linker comprises (Gly4Ser)3 linker.

In other aspects, the present disclosure includes a polynucleotide encoding the CAR of the present disclosure or a vector comprising the polynucleotide.

As used herein, the term "T cell" is a lymphocyte derived from the thymus and contrite to cell's immune response. The T cells include CD4+ T cells (helper T cells, TH cells), CD8+ T cells (cytotoxic T cells, CTL), memory T cells, regulatory T cells (Treg), or natural killer T cells. In some aspects, the T cell into which a CAR is introduced is a CD8+ T cell.

VII. Immunoconjugates, Antibody Derivatives and Diagnostics

Anti-L1CAM antibodies described herein can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels that can be linked to any anti-L1CAM antibody described herein can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo {3.3.1.1 3,7}decan}-4-yl) phenyl phosphate (CSPD), as well as CDP and CDP-STAR® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In some aspects, conjugation methods result in linkages which are substantially (or nearly) non-immunogenic, e.g., peptide- (i.e., amide-), sulfide-, (sterically hindered), disulfide-, hydrazone-, and ether linkages. These linkages are nearly non-immunogenic and show reasonable stability within serum (see e.g., Senter, P. D., *Curr. Opin. Chem. Biol.* 13 (2009) 235-244; WO 2009/059278; WO 95/17886).

Depending on the biochemical nature of the moiety and the antibody, different conjugation strategies can be employed. In case the moiety is naturally-occurring or recombinant of between 50 to 500 amino acids, there are standard procedures in text books describing the chemistry for synthesis of protein conjugates, which can be easily followed by the skilled artisan (see, e.g., Hackenberger, C. P. R., and Schwarzer, D., *Angew. Chem. Int. Ed. Engl.* 47 (2008) 10030-10074). In some aspects the reaction of a maleinimido moiety with a cysteine residue within the antibody or the moiety is used. This is an especially suited coupling chemistry in case e.g., a Fab or Fab'-fragment of an antibody is used. Alternatively, in some aspects, coupling to the C-terminal end of the antibody or moiety is performed. C-terminal modification of a protein, e.g., of a Fab-fragment, can be performed as described (Sunbul, M. and Yin, J., *Org. Biomol. Chem.* 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., *ChemBioChem.* 10 (2009) 425-427). It is also possible to obtain a desired amino acid modification by utilizing the specific enzymatic reactivity of certain enzymes with a natural amino acid in a given sequence context (see, e.g., Taki, M. et al., *Prot. Eng. Des. Sel.* 17 (2004) 119-126; Gautier, A. et al. *Chem. Biol.* 15 (2008) 128-136; and Protease-catalyzed formation of C—N bonds is used by Bordusa, F., Highlights in Bioorganic Chemistry (2004) 389-403). Site specific reaction and covalent coupling can also be achieved by the selective reaction of terminal amino acids with appropriate modifying reagents.

The reactivity of an N-terminal cysteine with benzonitrils (see Ren, H. et al., *Angew. Chem. Int. Ed. Engl.* 48 (2009) 9658-9662) can be used to achieve a site-specific covalent coupling.

Native chemical ligation can also rely on C-terminal cysteine residues (Taylor, E. Vogel; Imperiali, B, *Nucleic Acids and Molecular Biology* (2009), 22 (Protein Engineering), 65-96).

U.S. Pat. No. 6,437,095 B1 describes a conjugation method which is based on the faster reaction of a cysteine within a stretch of negatively charged amino acids with a cysteine located in a stretch of positively charged amino acids.

The moiety can also be a synthetic peptide or peptide mimic. In case a polypeptide is chemically synthesized, amino acids with orthogonal chemical reactivity can be incorporated during such synthesis (see e.g., de Graaf, A. J. et al., *Bioconjug. Chem.* 20 (2009) 1281-1295). Since a great variety of orthogonal functional groups is at stake and can be introduced into a synthetic peptide, conjugation of such peptide to a linker is standard chemistry.

In order to obtain a mono-labeled polypeptide, the conjugate with 1:1 stoichiometry can be separated by chromatography from other conjugation side-products. This procedure can be facilitated by using a dye labeled binding pair member and a charged linker. By using this kind of labeled and highly negatively charged binding pair member, mono conjugated polypeptides are easily separated from non-labeled polypeptides and polypeptides which carry more than one linker, since the difference in charge and molecular weight can be used for separation. The fluorescent dye can be useful for purifying the complex from un-bound components, like a labeled monovalent binder.

In some aspects the moiety attached to an anti-L1CAM antibody is selected from the group consisting of a binding moiety, a labeling moiety, and a biologically active moiety.

Anti-L1CAM antibodies described herein can also be conjugated to a therapeutic agent to form an immunoconjugate such as an antibody-drug conjugate (ADC). Suitable therapeutic agents include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. The ADCs can be prepared as described in U.S. Pat. Nos. 7,087,600; 6,989,452; and 7,129,261; PCT Publications WO 02/096910; WO 07/038658; WO 07/051081; WO 07/059404; WO 08/083312; and WO 08/103693; U.S. Patent Publications 20060024317; 20060004081; and 20060247295.

In some aspects, the therapeutic agent is selected from the group consisting of a cytotoxin, a non-cytotoxic drug, a radioactive agent, a second antibody, an enzyme, an anti-neoplastic agent, and any combination thereof.

In some aspects, the immunoconjugate comprises an anti-L1CAM antibody and a cytotoxin. The cytotoxin can be selected from any cytotoxin known in the art. In some aspects, the cytotoxin is selected from the group consisting of dolastatin, monomethyl auristatin E (MMAE), maytansine, duocarmycin, calicheamicin, pyrrolobenzodiazepine, duocarmycin, centanamycin, SN38, doxorubicin, a derivative thereof, a synthetic analog thereof, and any combination thereof. In certain aspects, the immunoconjugate comprises an anti-L1CAM antibody and Cytotoxin A. In other aspects, the immunoconjugate comprises an anti-L1CAM antibody and a non-cytotoxic drug.

In some aspects, the immunoconjugate comprises an anti-L1CAM antibody and a radioactive agent. In some aspects, the radioactive agent is a radionucleotide. In certain aspects, the radioactive agent comprises radioactive iodine. In particular aspects, the radioactive agent comprises 131-iodine. In other aspects, the radioactive agent comprises the radioactive isotope Yttrium-90.

In some aspects, the immunoconjugate comprises an anti-L1CAM antibody and a second antibody. In certain aspects, the immunoconjugate comprises an anti-L1CAM antibody and an enzyme. In some aspects, the enzyme comprises glucose oxidase. In some aspects, the enzyme comprises a peroxidase. In some aspects, the enzyme comprises myeloperoxidase. In some aspects, the enzyme comprises glucose oxidase. In some aspects, the enzyme comprises horseradish peroxidase.

In certain aspects, the immunoconjugate comprises an anti-L1CAM antibody and an anti-neoplastic agent. The anti-neoplastic agent can be any such agent known in the art. In some aspects, the anti-neoplastic agent is epirubicin. In some aspects, the anti-neoplastic agent is a super antigen. In certain aspects, the super antigen is staphylococcal enterotoxin A (SEA/E-120; estafenatox).

Anti-L1CAM antibodies, e.g., those described herein, can also be used for detecting L1CAM, such as human L1CAM, e.g., human L1CAM on the surface of a cell or soluble L1CAM in serum. The antibodies can be used, e.g., in an ELISA assay or in flow cytometry. In some aspects, an anti-L1CAM antibody is contacted with cells or serum for a time appropriate for specific binding to occur, and then a reagent, e.g., an antibody that detects the anti-L1CAM antibody, is added. Exemplary assays are provided in the Examples. Exemplary methods for detecting L1CAM, e.g., surface expressed L1CAM or soluble L1CAM (sL1CAM) in a sample (serum) comprise (i) contacting a sample with an anti-L1CAM antibody, for a time sufficient for allowing specific binding of the anti-L1CAM antibody to L1CAM in the sample, and (2) contacting the sample with a detection reagent, e.g., an antibody, that specifically binds to the anti-L1CAM antibody, such as to the Fc region of the anti-L1CAM antibody, to thereby detect L1CAM bound by the anti-L1CAM antibody. Wash steps can be included after the incubation with the antibody and/or detection reagent. Anti-L1CAM antibodies for use in these methods do not have to be linked to a label or detection agents, as a separate detection agent can be used.

Other uses for anti-L1CAM antibodies, e.g., as monotherapy or combination therapy, are provided elsewhere herein, e.g., in the section pertaining to combination treatments.

VIII. Bispecific Molecules

Anti-L1CAM antibodies described herein can be used for forming bispecific molecules. An anti-L1CAM antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. For example, an anti-L1CAM antibody can be linked to an antibody or scFv that binds specifically to any protein that can be used as potential targets for combination treatments. The antibody described herein can in fact be derived or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for L1CAM and a second binding specificity for a second target epitope. In some aspects described herein in which the bispecific molecule is multispecific, the molecule can further include a third binding specificity.

In some aspects, the bispecific molecules described herein comprise as a binding specificity at least one antibody, or an antibody fragment thereof, including, e.g., an Fab, Fab', F(ab')2, Fv, or a single chain Fv (scFv). The antibody can also be a light chain or heavy chain dimer, or any minimal fragment thereof such as a Fv or a single chain construct as described in Ladner et al. U.S. Pat. No. 4,946,778.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. See, e.g., Karpovsky et al. (1984) *J. Exp. Med.* 160: 1686; Liu, M A et al. (1985) *Proc. Natl. Acad. Sci. USA* 82:8648. Other methods include those described in Paulus (1985) *Behring Ins. Mitt. No.* 78, 118-132; Brennan et al. (1985) *Science* 229:81-83), and Glennie et al. (1987) *J. Immunol.* 139: 2367-2375). Some conjugating agents are SATA and sulfo-SMCC, both available from Pierce Chemical Co. (Rockford, IL).

IX. Compositions

Provided herein are Further provided are compositions, e.g., a pharmaceutical compositions, containing one or a combination of anti-L1CAM antibodies or combination with antibodies to other targets, or antigen-binding portion(s) thereof, described herein, formulated together with a pharmaceutically acceptable carrier. Such compositions can include one or a combination of (e.g., two or more different) antibodies, or immunoconjugates or bispecific molecules described herein. For example, a pharmaceutical composition described herein can comprise a combination of antibodies (or immunoconjugates or bispecifics) that bind to different epitopes on the target antigen or that have complementary activities.

Pharmaceutical compositions described herein also can be administered in combination therapy, i.e., combined with other agents. For example, the combination therapy can include an anti-L1CAM antibody described herein combined with at least one other anti-cancer and/or immunomodulating, e.g., T-cell stimulating (e.g., activating) agent. Examples of therapeutic agents that can be used in combination therapy are described in greater detail below in the section on uses of the anti-L1CAM antibodies described herein.

In some aspects, the composition of the invention further comprises a bulking agent. A bulking agent can be selected from the group consisting of NaCl, mannitol, glycine, alanine, and any combination thereof. In other aspects, the composition of the invention comprises a stabilizing agent. The stabilizing agent can be selected from the group consisting of sucrose, trehalose, raffinose, arginine; or any combination thereof. In other aspects, the composition of the invention comprises a surfactant. The surfactant can be selected from the group consisting of polysorbate 80 (PS80), polysorbate 20 (PS20), and any combination thereof. In certain aspects, the composition further comprises a chelating agent. The chelating agent can be selected from the group consisting of diethylenetriaminepentaacetic acid (DTPA), ethylenediaminetetraacetic acid, nitrilotriacetic acid, and any combination thereof.

In other aspects, the composition comprises a third antibody. In some aspects, the third antibody is any antibody disclosed herein.

In one aspect, the composition further comprises NaCl, mannitol, pentetic acid (DTPA), sucrose, PS80, and any combination thereof.

As used herein, "pharmaceutically acceptable carrier" includes any and all solvents, dispersion media, coatings, antibacterial and antifungal agents, isotonic and absorption delaying agents, and the like that are physiologically compatible. In some aspects, the carrier is suitable for intravenous, intramuscular, subcutaneous, parenteral, spinal or epidermal administration (e.g., by injection or infusion). An option for subcutaneous injection is based on Halozyme Therapeutics' ENHANZE® drug-delivery technology, involving a co-formulation of an Ab with recombinant human hyaluronidase enzyme (rHuPH20) that removes traditional limitations on the volume of biologics and drugs that can be delivered subcutaneously due to the extracellular matrix (U.S. Pat. No. 7,767,429). Depending on the route of administration, the active compound, i.e., antibody, immunoconjugate, or bispecific molecule, can be coated in a material to protect the compound from the action of acids and other natural conditions that can inactivate the compound.

The pharmaceutical compounds described herein can include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1-19A pharmaceutical composition described herein can also include a pharmaceutically acceptable anti-oxidant.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition can comprise a preservative or can be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition.

Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

For administration of an anti-L1CAMantibody, e.g., described herein, the dosage ranges from about 0.0001 to 100 mg/kg.

In some methods, two or more monoclonal antibodies with different binding specificities are administered simultaneously, in which case the dosage of each antibody administered falls within the ranges indicated. Antibody is usually administered on multiple occasions.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and until the patient shows partial or complete amelioration of symptoms of disease. Thereafter, the patient can be administered a prophylactic regime.

A "therapeutically effective dosage" of an anti-L1CAM antibody described herein can result in a decrease in severity of disease symptoms, an increase in frequency and duration of disease symptom-free periods, or a prevention of impairment or disability due to the disease affliction. In the context of cancer, a therapeutically effective dose can result in increased survival, e.g., overall survival, and/or prevention of further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

A therapeutically effective dose can prevent or delay onset of cancer, such as can be desired when early or preliminary signs of the disease are present. Laboratory tests utilized in the diagnosis of cancer include chemistries (including the measurement of L1CAM levels), hematology, serology and radiology. Accordingly, any clinical or biochemical assay that monitors any of the foregoing can be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Routes of administration for the anti-L1CAM antibodies described herein can include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein could potentially be administered via a non-parenteral route, such as a topical, epidermal or mucosal route of administration, for example, intranasally, orally, vaginally, rectally, sublingually or topically.

X. Kits

Provided herein are kits comprising one or more antibodies described herein, or antigen-binding fragments thereof, bispecific molecules, or immunoconjugates thereof. In a specific aspect, provided herein is a pharmaceutical pack or kit comprising one or more containers filled with one or more of the ingredients of the pharmaceutical compositions described herein, such as one or more antibodies provided herein or an antigen-binding fragment thereof, optional an instructing for use. In some aspects, the kits contain a pharmaceutical composition described herein and any prophylactic or therapeutic agent, such as those described herein.

XI. Uses and Methods

Certain aspects of the present disclosure are directed to method of treating a subject, comprising administering to the subject an anti-L1CAM antibody disclosed herein, a polynucleotide encoding the anti-L1CAM antibody, a vector comprising the polynucleotide, a host cell comprising the polynucleotide, an immunoconjugate comprising an anti-L1CAM antibody, or any combination thereof.

Certain aspects of the present disclosure are directed to a method of treating a cancer in a subject in need thereof, comprising administering to the subject an effective dose of a composition disclosed herein (e.g., an antibody, polynucleotide, vector, host cell, immunoconjugate, or pharmaceutical composition). In other aspects, the present disclosure is directed to a method of inhibiting shedding of L1 CAM by a tumor cell in a subject in need thereof, comprising administering to the subject an effective dose of a composition disclosed herein. In other aspects, the present disclosure is directed to a method of reducing shed L1CAM in the serum and/or retaining L1CAM on the cell surface in a subject in need thereof, comprising administering to the subject an effective dose of a composition disclosed herein. In other aspects, the present disclosure is directed to a method of killing a tumor cell in a subject in need thereof, comprising administering to the subject an effective dose of a composition disclosed herein. In other aspects, the present disclosure is directed to a method of reducing the size of a tumor in a subject in need thereof, comprising administering to the subject an effective dose of a composition disclosed herein. In other aspects, the present disclosure is directed to inhibiting metastasis of a tumor in a subject in need thereof, comprising administering to the subject an effective dose of a composition disclosed herein. In some aspects, the subject is a human.

The compositions of the present disclosure can be administered using any pharmaceutically acceptable route. In some aspects, the composition (e.g., antibody, polynucleotide, vector, host cell, immunoconjugate, or pharmaceutical composition) is administered intravenously, intraperitoneally, intramuscularly, intraarterially, intrathecally, intralymphaticly, intralesionally, intracapsularly, intraorbitally, intracardiacly, intradermally, transtracheally, subcutaneously, subcuticularly, intraarticularly, subcapsularly, subarachnoidly, intraspinally, epidurally, intrasternally, topically, epidermally, mucosally, or any combination thereof. In some aspects, the composition is administered intravenously. In some aspects, the composition is administered subcutaneously.

In certain aspects, the method reduces the size of a cancer, e.g., the size of a tumor, in the subject. In some aspects, the size of the caner is reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%.

In some aspects, the method increases the overall survival of the subject. In some aspects, the overall survival is increased relative to the average overall survival of a subject having the same cancer but treated with a different therapy. In certain aspects, the overall survival is increased by at least about 10%, at least about 20%, at least about 25%, at least about 50%, at least about 2 fold, at least about 3 fold, at least about 5 fold. In some aspects, the overall survival is increased by at least about one month, at least about 2 months, at least about 3 months, at least about 4 months, at least about 5 months, at least about 6 months, at least about 7 months, at least about 8 months, at least about 9 months, at least about 10 months, at least about 1 months, at least about 12 months, at least about 15 months, at least about 18 months, at least about 21 months, at least about 2 years, at least about 3 years, at least about 4 years, at least about years, or at least about 10 years.

In some aspects, the method increases the progression free survival of the subject. In some aspects, the overall survival is increased relative to the average progression free survival of a subject having the same cancer but treated with a different therapy. In certain aspects, the progression free survival is increased by at least about 10%, at least about 20%, at least about 25%, at least about 50%, at least about 2 fold, at least about 3 fold, at least about 5 fold. In some aspects, the overall survival is increased by at least about one month, at least about 2 months, at least about 3 months, at least about 4 months, at least about 5 months, at least about 6 months, at least about 7 months, at least about 8 months, at least about 9 months, at least about 10 months, at least about 1 months, at least about 12 months, at least about 15 months, at least about 18 months, at least about 21 months, at least about 2 years, at least about 3 years, at least about 4 years, at least about 5 years, or at least about 10 years.

In some aspects, the method increases the objective response rate of the subject. In certain aspects, the method induces a complete response in the subject. In some aspects, the method induces a partial response in the subject.

In some aspects, the method comprises administering an anti-L1CAM antibody (or a polynucleotide, vector, host cell, or immunoconjugate) disclosed herein and a second therapy. In some aspects, the second therapy is administered prior to the anti-L1CAM antibody. In some aspects, the second therapy is administered after the anti-L1CAM antibody. In some aspects, the second therapy is administered concurrently with the anti-L1CAM antibody. In certain aspects, the anti-L1CAM antibody and the second therapy are administered separately. In other aspects, the anti-L1CAM antibody and the second therapy are administered in a single formulation.

The second therapy can be any other therapy known in the art. In some aspects, the second therapy comprises an immunotherapy. In some aspects, the second therapy comprises a chemotherapy. In some aspects, the second therapy comprises a radiotherapy. In some aspects, the second therapy comprises a surgery. In some aspects, the second therapy comprises administering a second therapeutic agent.

Anti-L1CAM antibodies can enhance the immune response to cancerous cells in a patient having cancer. Provided herein are methods for treating a subject having cancer, comprising administering to the subject an anti-L1CAM antibody described herein, such that the subject is treated, e.g., such that growth of cancerous tumors is inhibited or reduced and/or that the tumors regress and/or that prolonged survival is achieved. An anti-L1CAM antibody can be used alone to inhibit the growth of cancerous tumors. Alternatively, an anti-L1CAM antibody can be used in conjunction with another agent, e.g., another immunogenic agent, a standard cancer treatment, or another antibody, as described below.

Accordingly, provided herein are methods of treating cancer, e.g., by inhibiting growth of tumor cells, in a subject, comprising administering to the subject a therapeutically effective amount of an anti-L1CAM antibody described herein. Cancers whose growth can be inhibited using the antibodies of the disclosure include cancers typically responsive to immunotherapy and those that are not typically responsive to immunotherapy. Cancers that can be treated also include L1CAM positive cancers. Cancers can be cancers with solid tumors or hematolotical malignancies (liquid tumors). Non-limiting examples of cancers for treatment include bile duct cancer, squamous cell carcinoma, small-cell lung cancer, non-small cell lung cancer, squamous non-small cell lung cancer (NSCLC), nonsquamous NSCLC, glioma, gastrointestinal cancer, renal cancer (e.g., clear cell carcinoma), ovarian cancer, liver cancer, colorectal cancer, endometrial cancer, kidney cancer (e.g., renal cell carcinoma (RCC)), prostate cancer (e.g., hormone refractory prostate adenocarcinoma), thyroid cancer, neuroblastoma, pharyngeal cancer, laryngeal cancer, mouth cancer, cancer of connective tissue, Hodgkin's lymphoma, lymphoma, multiple myeloma, pancreatic cancer, glioblastoma (glioblastoma multiforme), cervical cancer, stomach cancer, bladder cancer, hepatoma, breast cancer, colon adenocarcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, rectal cancer, solid tumors of childhood, cancer of the ureter, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, environmentally-induced cancers including those induced by asbestos, virus-related cancers or cancers of viral origin (e.g., human papilloma virus (HPV-related or -originating tumors)); and any combinations of said cancers.

In some aspects, an anti-L1CAM antibody is administered to patients having a cancer that exhibited an inadequate response to, or progressed on, a prior treatment, e.g., a prior treatment with an immuno-oncology or immunotherapy drug, or patients having a cancer that is refractory or resistant, either intrinsically refractory or resistant or a wherein the resistance or refractory state is acquired. For example, subjects who are not responsive or not sufficiently responsive to a first therapy or who see disease progression following treatment can be treated by administration of an anti-L1CAM antibody alone or in combination with another therapy.

In some aspects, an anti-L1CAM antibody is administered to patients who have not previously received (i.e., been treated with) an immuno-oncology agent.

In some aspects, a method of treating cancer in a subject comprises first determining whether the subject is L1CAM positive, e.g., has tumor cells that express L1CAM, and if the subject has L1CAM positive cancer, then administering to the subject an anti-L1CAM antibody, e.g., described herein. A method of treating a subject having cancer with an anti-L1CAM antibody may comprise administering to a subject who has cancer cells that express L1CAM, a therapeutically effective amount of a L1CAM antibody. Also provided herein are methods for predicting whether a subject will respond to treatment with an anti-L1CAM antibody, wherein the methods comprise determining the level of L1CAM in cancer cells of the patient, and if cancer cells of the subject are L1CAM positive, then the subject is likely to respond to a treatment with a L1CAM antibody.

An anti-L1CAM antibody can be administered with a standard of care treatment. An anti-L1CAM antibody can be administered as a maintenance therapy, e.g., a therapy that is intended to prevent the occurrence or recurrence of tumors.

An anti-L1CAM antibody can be administered with another treatment, e.g., radiation, surgery, or chemotherapy. For example, anti-L1CAM antibody adjunctive therapy can be administered when there is a risk that micrometastases can be present and/or in order to reduce the risk of a relapse.

An anti-L1CAM antibody, e.g., an anti-L1CAM antibody described herein, can be combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, *Cancer: Principles and Practice of Oncology*, Fifth Edition).

Administration of an anti-L1CAM antibody can also be combined with standard cancer treatments (e.g., surgery, radiation, and chemotherapy). Administration of an anti-L1CAM antibody can be effectively combined with chemotherapeutic regimes. In these instances, it can be possible to reduce the dose of chemotherapeutic reagent administered (Mokyr et al. (1998) *Cancer Research* 58: 5301-5304).

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) *Molecular Cloning A Laboratory Manual* (2nd ed.; Cold Spring Harbor Laboratory Press); Sambrook et al., ed. (1992) *Molecular Cloning: A Laboratory Manual*, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) *Transcription And Translation*; Freshney (1987) Culture Of Animal Cells (Alan R. Liss, Inc.); Immobilized Cells And Enzymes (IRL Press) (1986); Perbal (1984) *A Practical Guide To Molecular Cloning*; the treatise, Methods In Enzymology (Academic Press, Inc., N.Y.); Miller and Calos eds. (1987) *Gene Transfer Vectors For Mammalian Cells*, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooks, Antisense drug Technology: Principles, strategies and applications, 2n d Ed. CRC Press (2007) and in Ausubel et al. (1989) *Current Protocols in Molecular Biology* (John Wiley and Sons, Baltimore, Md.).

The following examples are offered by way of illustration and not by way of limitation.

EXAMPLES

The following experimental methods and details are referenced in the Examples that follow.

Example 1. Construction of Ab612 by Site-Direct Mutagenesis

Mammalian (e.g., human and mouse) L1CAM-binding human antibody Ab417 and a preparation procedure thereof are disclosed in U.S. Pat. No. 9,777,060 and in International Publication No. WO2014/077648, which are herein incorporated by reference. To improve the biophysical properties of the Ab417 antibody, effects of the respective amino acids constituting the variable region of the Ab417 antibody on the binding capacity of Ab417 antibody were examined.

DNA was synthesized to carry mutations R16G, D54E, K76A, and P88A in the heavy-chain variable region of the Ab417 antibody, and recombined with the gene encoding the CH1 domain of human Cγ1 by polymerase chain reaction (PCR). The resulting PCR product was electrophoresed on a 1.5% agarose gel. Bands containing DNAs were cut out and purified using the PCR-purification kit (GeneAll®). Both ends of the purified DNAs were digested with restriction enzymes NcoI and ApaI (New England Biolabs), and subcloned into the NcoI and ApaI sites of a modified version (pKRIBB-full GIII) of the human Fab phage display vector pKRIBB-FabD (ref), which carries the full length of Gene III. The resulting recombinant phagemid was named pKRIBB-full GIII-Fd612.

DNA was synthesized to carry mutations I31S and V95P in the light-chain variable region of the Ab417 antibody, and recombined with the gene encoding the human Cκ by PCR. The resulting PCR product was electrophoresed on a 1.5% agarose gel. Bands containing DNAs were cut out and purified using the PCR-purification kit (GeneAll®). Both ends of the purified DNAs were digested with restriction enzyme BstXI (New England Biolabs), and subcloned into the BstXI sites of the pKRIBB-full GIII-Fd612. The resulting recombinant phagemid was named pKRIBB-full GIII-Fab612. To this end, the antibody comprising mutations R16G, D54E, K76A, and P88A in the heavy-chain variable region and mutaions I31S and V95P in the light-chain variable region of the Ab417 antibody was named Ab612 antibody.

Example 2. Construction of Phage-Displayed Ab612 Variant Fab Library

To improve the affinity and the biophysical properties of the Ab612 antibody prepared in Example 1, five positions of Ab612 LCDR3 were randomized by TRIM (trinucleotide mutagenesis, ELLA biotech, Germany). The fragment A which contains the sequence from FR1 to FR3 of Ab612 was synthesized. The fragment B (5'-TTT AAT TTC CAC TTT AGT TCC CTG CCC GAA CGT CCA CGG X17 X15 X15 X13 X15 TTG CTG ACA ATA ATA GGT GGC AAA ATC TTC-3'), which contains the sequence from Ab612 FR3 to FR4 with randomized LCDR3, was synthesized. X denotes number of amino acid; X17 is 17 amino acids, X15 and X13 are 15 amino acids and 13 amino acids, respectively. Fragments A and B were assembled by recomnant PCR with Phusion High-Fidelity DNA polymerase (Thermo Fisher Scientific). The resulting PCR products were purified using PCR purification kit (GeneAll®), digested with BstXI restriction enzyme (New England Biolabs), and ligated with the BstXI-digested pKRIBB-full GIII-Fab612 expression vector with 1:3 vector to insert molar ratio. The DNA was electroporated into competent E. coli TG1. The Ab612 variants Fab library produced 5.92×10$^8$ colonies.

To isolate monoclonal antibodies that recognize human L1CAM, the human L1CAM was used as an antigen in the first, second, and third rounds of panning.

After the three rounds of panning, 470 colonies were selected randomly and separately inoculated in the 96-well plates, and then cultured in 300 μl of the 2× YT/carbenicillin/glucose at 37° C. for 8 h. Subsequently, 30 μl of the cells were seeded in each well containing 1 ml of 2× YT/carbenicillin/glucose medium and cultured for 2 h until reaching OD600 of 0.5. The cells were infected with KM13 helper phage at 20 multiplicity of infection (MOI) without shacking at 37° C. for 30 min and then incubated with shacking for 30 min. The infected cells were resuspended in 2×YT/carbenicillin/kanamycin after centrifugation at 2900×g for 10 min and cultured at 30° C. for 12 h. The supernatant containing Fab phages from the 470 colonies was subjected to indirect and quantitative ELISAs.

Among them, 41 clones binding to human L1CAM with high activity were selected and their plasmid DNAs were isolated and sequenced. As a result, it was found that the 32 clones were different from each other.

To analyze binding capacity of the 32 unique clones to human L1CAM, indirect ELISA was performed. As a result, 4 clones were found to show the highest antigen binding capacity (i.e., Ab4H5, Ab2C2, Ab4H6 and Ab5D12).

Example 3. Conversion of Fab into IgG1 and Production

To convert the Fab into whole IgG1 with codon-optimized sequence for mammalian cell, heavy and light chain variable regions with leader sequences were amplified by PCR and subcloned into the EcoRI and ApaI sites (New England Biolabs) and the BsiWI and HindIII sites (New England Biolabs), respectively, in the mammalian IgG1 expression plasmid pdCMV-dhfr-Ab612 vector. HEK293F cells were cultivated and transfected with the IgG1 expression plasmid using ExpiFectamin (Thermo Fisher Scientific) according to the ExpiCHO protocols. After 7-14 days from transfection, cell culture supernatants were centrifuged and filtered using a bottle top filter (0.22 μm PES, Sartorius), and productivity of the respective mutant was compared with that of the existing Ab417 antibody by ELISA as described below in Example 5.

As shown in Table 8, the variant antibodies showed productivity which is 1.25-1.44-fold higher than Ab417. Ab612 was enhanced by 1.44-fold, while Ab4H5, Ab2C2, Ab4H6, and Ab5D12 were enhanced by 1.25-fold, 1.26-fold, and 1.36-fold, and 1.26-fold, respectively.

TABLE 8

Productivity of Ab612, Ab4H5, Ab2C2, Ab4H6, and Ab5D12 antibodies compared to Ab417

| Antbody | Productivity (mg/L) |
|---|---|
| Anti-L1CAM ("Ab417") | 52 |
| Anti-L1CAM ("Ab612") | 75 |
| Anti-L1CAM ("Ab4H5") | 65 |
| Anti-L1CAM ("Ab2C2") | 66 |
| Anti-L1CAM ("Ab4H6") | 71 |
| Anti-L1CAM ("Ab5D12") | 66 |

Example 4. Purification of Ab417 Variant Antibodies

Plasmid DNAs of expression vectors of these antibodies were obtained in a large amount, and expressed in ExpiCHO cells in the same manner as in Examples 1-3, respectively. The cell cultures were centrifuged to collect the supernatants. The supernatants were filtered using a bottle top filter (0.22 μm PES, Sartorius) and purified by affinity chromatography. The respective supernatants were applied to a column packed with protein A-coupled beads (Amicogen), and antibodies were eluted from protein A using a 0.1 M sodium-citric acid solution (pH 3.2). Then, 1.0 M Tris solution (pH 8.0) was immediately added to the eluted antibodies for neutralization. The purified IgG1 was stored in buffer (10 mM Napi 5% sorbitol 0.01% tween 20) after dialysis using PD-10 column with sephadex G-25 (GE Healthcare). Concentration of the purified antibody was determined with a Nanodrop (Thermo Fisher Scientific, Nanodrop 2000) based on the molar extinction coefficient. The purified antibodies were subjected to 10% SDS-PAGE and Coomassie staining to confirm that each of the heavy chain and light chains was expressed and assembled as a whole IgG.

Example 5. Characterization of Ab417 Variant Antibodies

The affinities of the purified antibodies for human L1 CAM were measured by competitive ELISA. Human L1CAM was prepared at a density of $1\times10^{-7}$ M and serially diluted to $1\times10^{-12}$ M using a 0.1% PBA buffer (PBS containing 0.1% BSA) solution. Respective antibodies were prepared by diluting them in 0.1% PBA buffer solution at particular concentrations according to their binding capacity. The diluted antigens and antibodies were reacted with each other at the same volume ratio at 37° C. for 3 hours. 96-well plates (MaxiSorp, Nunc) were coated using the purified human L1 CAM which were diluted in a buffer solution (15 mM $Na_2CO_3$, 34.84 mM NaHCO3, pH 9.6) at a concentration of 100 ng/well, at 4° C. overnight. Next day, Difco skim milk (BD) was dissolved in 0.05% PBS-T buffer solution at a concentration of 2%, and 200 ul was added to each well, followed by incubation at 37° C. for 1 hour. The wells were washed with 0.05% PBS-T buffer solution twice. Then 100 ul of the antigen/antibody reactant that was reacted for 3 hours was added and allowed to react at room temperature for 1 hour. The wells were washed with 0.05% PBS-T buffer solution three times to remove the non-antigen bound antibodies. Goat anti-human IgG(Fc)-HRP (invitrogen, 1/10000) that specifically recognizes the Fc region of human antibody was added as a secondary antibody, and allowed to react at 37° C. for 1 hour. The wells were washed with 0.05% PBS-T buffer solution four times to remove the remaining secondary antibodies. To examine the affinity by color development, 100 ul of a solution (BD OptEIA, BD) containing TMB as a substrate of the enzyme HRP (which was covalently linked to the secondary antibody) was added to each well, and incubated at room temperature for 5 minutes. Finally, 50 ul of 2.5 M HSO solution was added to each well to terminate the enzymatic reaction. After terminating the reaction, absorbance was measured at 450 nm (VERSAmax microplate reader, Molecular Devices). The results are shown in Table 9. Affinity of Ab417 for human L1CAM was 5×10–10 M, affinity of Ab612 was 2.6×10–10 M, affinity of Ab4H5 mutant was 6×10–11 M, affinity of Ab2C2 mutant was 5×10–11 M, affinity of Ab4H6 mutant was 6×10–11 M, affinity of Ab5D12 mutant was 1.2×10–10 M. Ab417 variant antibodies showed about 2-10 fold higher binding affinity for human L1CAM than Ab417 antibody.

TABLE 9

Affinity (K) of Ab612, Ab4H5, Ab2C2, Ab4H6, and Ab5D12 antibodies for human L1CAM compared to Ab417

| Antbody | Affinity (K) M |
|---|---|
| Anti-L1CAM ("Ab417") | $5 \times 10^{-10}$ |
| Anti-L1CAM ("Ab612") | $2.6 \times 10^{-10}$ |

TABLE 9-continued

Affinity (K) of Ab612, Ab4H5, Ab2C2, Ab4H6, and Ab5D12 antibodies for human L1CAM compared to Ab417

| Antbody | Affinity (K) M |
|---|---|
| Anti-L1CAM ("Ab4H5") | $6 \times 10^{-11}$ |
| Anti-L1CAM ("Ab2C2") | $5 \times 10^{-11}$ |
| Anti-L1CAM ("Ab4H6") | $6 \times 10^{-11}$ |
| Anti-L1CAM ("Ab5D12") | $1.2 \times 10^{-10}$ |

Example 6. Analysis of Antigen-Binding Specificity of Ab417 Variants

In order to examine whether the variant antibodies selectively bind to human and mouse L1CAM, flow cytometry was performed using various types of cells. In this regard, as a comparative antibody, the Ab417 antibody which binds to human L1 CAM and mouse L1 CAM was used.

CHO-DG44 (ATCC No. PTA-3356) cells that are known to express no human L1CAM were cultured and used as a negative control. Also, cells expressing human L1CAM, human ovarian carcinoma, SKOV3 (ATCC No. HTB-77) and human non-small cell lung carcinoma, NCI-H522 (AYCC NO. CRL-5810) were cultured. As cells expressing mouse L1CAM, a melanoma cell line, B16F1 (ATCC No. CRL-6323) was cultured. The cultured cells were harvested using a dissociation buffer or 0.05% trypsin (GIBCO) for CHO-DG44 cell, resuspended in 1% PBA solution, and placed on ice for 20 minutes. The cells were then added to round bottom polystyrene test tube (Falcon) at a density of $4\times10^5$ cells per tube. The purified antibodies were diluted in PBA solution at a concentration of 10 ug/ml, and 100 ul was added to each tube and mixed well. The tubes were placed in 4° C. for 1 hour. The secondary antibody which specifically binds to the Fc region of human IgG and is covalently linked with FITC (Sigma) was added to each tube at a ratio of 1:2000. The plate was wrapped with foil to block light and allowed to react at 4° C. for 1 hour. A staining reagent PI (propidium iodide, Sigma) was added at a ratio of 1:200 to evaluate cell viability. After all reactions were completed, FITC and PI fluorescent signals were detected in the cells. FIG. 1A shows that variant antibodies do not bind to L1CAM-negative cells (i.e., CHO-DG44). FIGS. 1B-1D show that variant antibodies bind to human L1CAM-positive cells, NCI-H522 (FIG. 1B), SKOV3 (FIG. 1C), and mouse L1CAM-positive cells, B16F1 (FIG. 1D). The variant antibodies specifically bind to the mouse melanoma cell line B166F1, suggesting that the Ab417 variants of the present invention specifically bind to both human and mouse L1CAM.

Example 7. Measuring Quality of Purified Ab417 Variants by SEC-HPLC

HPLC grade UPLC solvents and PBS were purchased from Fisher Scientific (Fair Lawn, NJ, USA) and GIBCO (St. Louis, MO, USA), respectively. The size exclusion chromatography was used for separation of antibody samples with Biosuit High Resolution SEC column (7.5× 300 mm, 250 Å particle size). The samples were separated using PBS pH 7.4 with isocratic flow. The Waters® e2695 Separations Module was used for the experiments, and the 2489 UV/Vis Detector monitored the absorbance at 280 nm. Size exclusion-high-performance liquid chromatography (SEC-HPLC) analysis showed that the variant antibodies displayed monomer peak (FIGS. 2B-2F), even though Ab417 had high molecular weight aggregates and low molecular fragments with a broad peak (FIG. 2A).

Example 8. Analysis of Affinity of Ab417 Variants for Human L1CAM

Affinities of Ab417 and Ab417 variants for human L1 CAM were examined by BLI using Octet RED384 (ForteBio). For affinity analysis, the antibodies were diluted with a PBA solution prepared by adding 0.1% BSA to PBS. Human L1CAM was serially diluted with PBA at a concentration of 50, 25, 12.5, 6.25, 3.125, 1.5625, 0.78125, or 0 nM, then 200 ul of diluted L1CAM was added to opaque 96-well plate to prevent light transmission. AHC (anti-human IgG Fc capture) sensor chip was used to analyze binding kinetics of the antibodies to antigens by examining changes in refractive index which occurs upon association and dissociation of antibody and antigen while transferring the sensor chip to PBA solution, antibody, PBA solution, antigen, and PBA solution in this order.

Table 10 shows that affinity ($K_D$) of Ab417 for human L1CAM was about 0.2 nM, affinity of Ab612 was 0.1 nM, affinity of Ab4H5 was 8 pM, affinity of Ab2C2H was out of range, affinity of Ab4H6 was 0.07 nM, and affinity of Ab5D12 was 0.09 nM. The increased affinity of the variants compared to Ab417 (e.g., up to 25-fold) was due to the slower dissociation rate.

TABLE 10

Affinity ($K_D$) of Ab612, Ab4H5, Ab2C2, Ab4H6, and Ab5D12 antibodies for human L1CAM compared to Ab417

| Antigen | Antibody | KD (M) | kon(1/Ms) | kdis(1/s) | Full X^2 | Full R^2 |
|---|---|---|---|---|---|---|
| hL1-s1 | Ab417 | 2.63E−10 | 3.59E+05 | 9.45E−05 | 0.2376 | 0.9936 |
|  | Ab612 | 1.05E−10 | 3.13E+05 | 3.28E−05 | 0.1235 | 0.997 |
|  | Ab4H5 | 8.22E−12 | 3.63E+05 | 2.98E−06 | 0.2097 | 0.9956 |
|  | Ab2C2 | <1.0E−12 | 3.44E+05 | <1.0E−07 | 0.3084 | 0.9933 |
|  | Ab4H6 | 7.41E−11 | 3.73E+05 | 2.77E−05 | 0.2228 | 0.9943 |
|  | Ab5D12 | 9.60E−11 | 4.11E+05 | 3.94E−05 | 0.2524 | 0.9936 |

Example 9. Isoelectric Point (PI) Analysis of Ab417 Variants

The Sciex PA800 plus instrument with a neutral coated capillary (Sciex PN 477441) was used to perform capillary isoelectricfocusing (cIEF) of Ab417 and mutants thereof. All experiments were performed triplicate. PI values of respective materials were determined using 32 Karat software. Table 11 shows that pI value of Ab417 antibody was 9.62, pI value of Ab612 was 9.25, pI value of Ab4H5 was 8.96, pI value of Ab2C2 was 8.96, pI value of Ab4H6 was 9.03, and pI value of Ab5D12 was 9.04.

TABLE 11

PI value of Ab612, Ab4H5, Ab2C2, Ab4H6, and Ab5D12 compared to Ab417

| Antbody | PI Value |
|---|---|
| Anti-L1CAM ("Ab417") | 9.62 |
| Anti-L1CAM ("Ab612") | 9.25 |
| Anti-L1CAM ("Ab4H5") | 8.96 |
| Anti-L1CAM ("Ab2C2") | 8.96 |
| Anti-L1CAM ("Ab4H6") | 9.03 |
| Anti-L1CAM ("Ab5D12") | 9.04 |

Example 10. Analysis of Tumor Growth-Inhibitory Effect of Ab417 Variants

To investigate anti-tumor effect of the Ab612 antibody, male Balb/c nude mice were transplanted with human-derived cholangiocarcinoma cell line Choi-CK. Constructed Choi-Ck tumor tissue (3×3×3 mm$^3$) was inoculated into the back of mice. After tumor volume reached to 100 mm$^3$ (n=8 per group), Ab417 antibody at a dose of 10 mg/kg, Ab612 antibody at a dose of 10 mg/kg, control hFc antibody at a dose of 3.3 mg/kg, and negative control (PBS) or (vehicle) was i.v. injected three times per week for 3 weeks. The tumor volume, the body weight of the mice, and tumor weight were measured and shown in FIGS. 1A-1C, respectively.

Figure 3B:
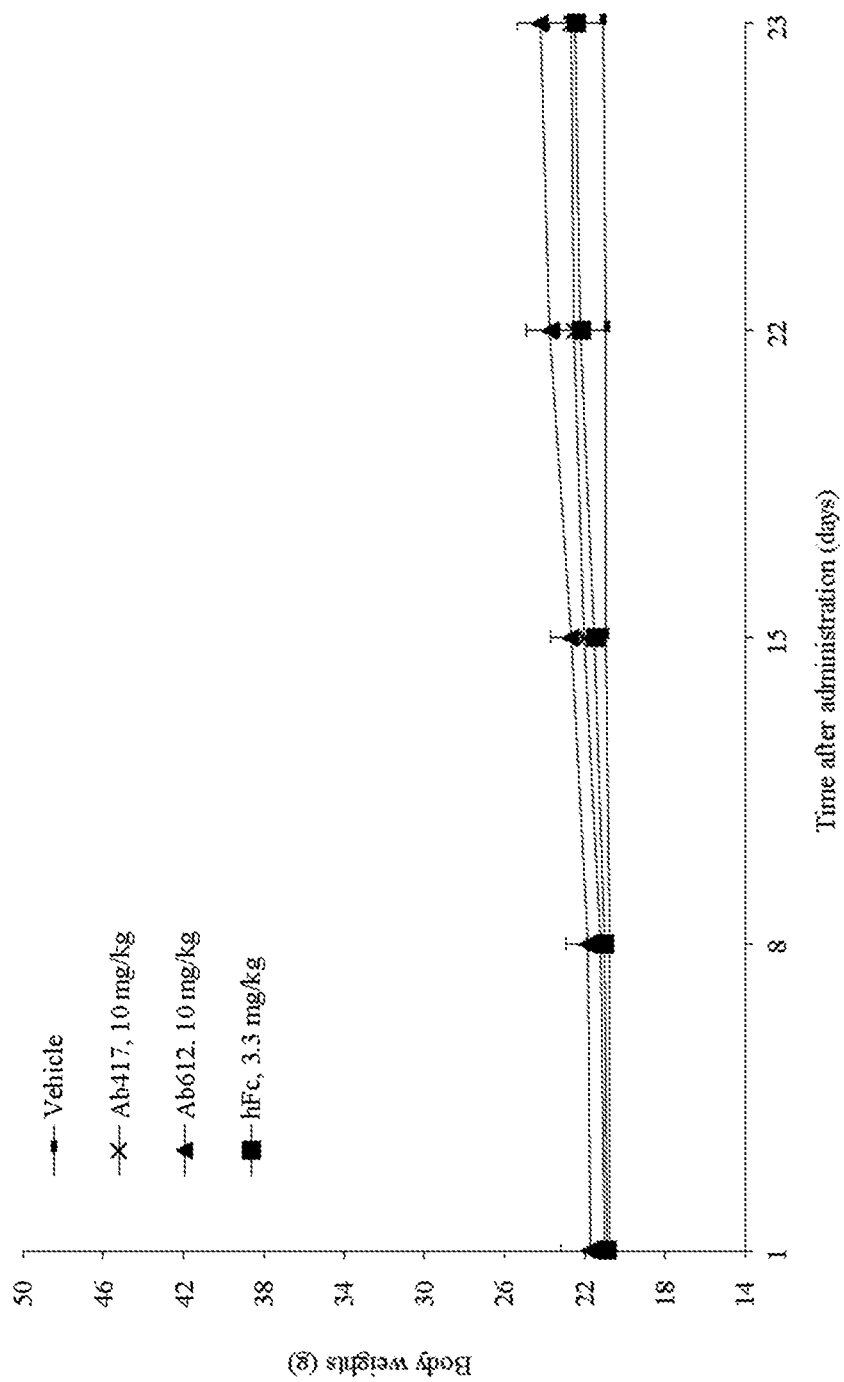
Figure 3D:
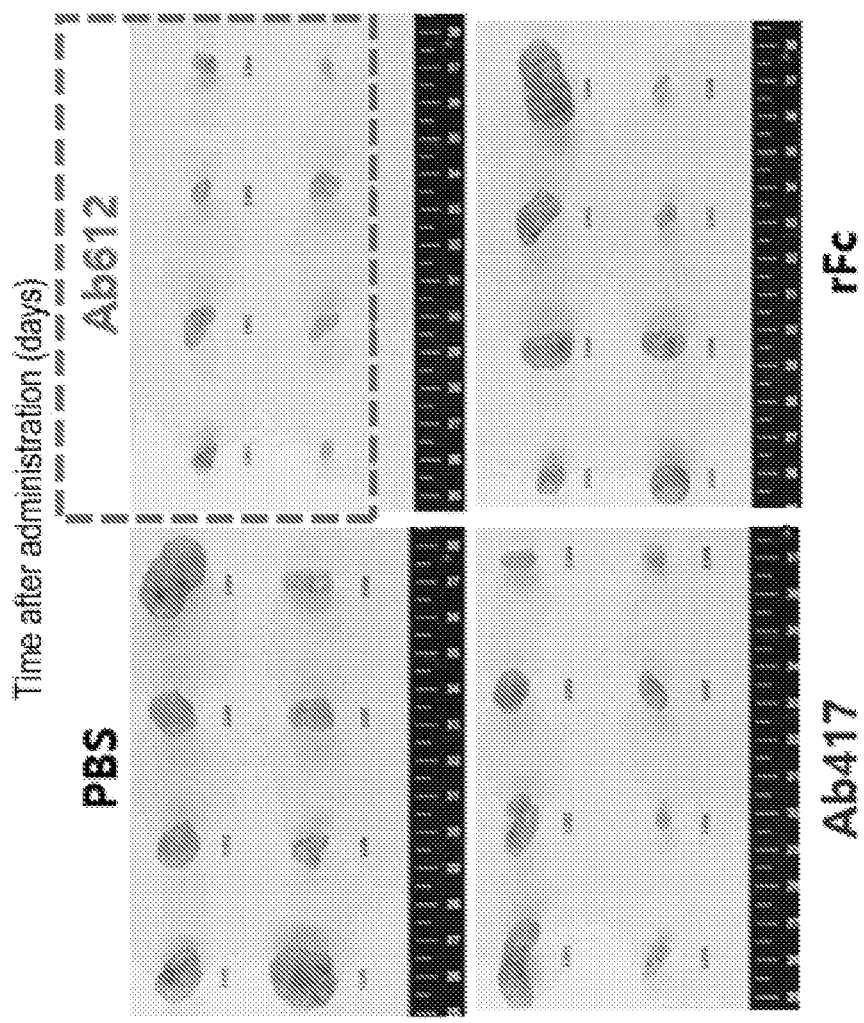

FIGS. 3A and 3C show that Ab612-treated groups showed a mean tumor volume of 311 mm$^3$ and tumor weight of 0.20 g, whereas Ab417-treated groups showed a mean tumor volume of 387 mm$^3$ and tumor weight of 0.41 g. The mock-treated control mice showed a mean tumor volume of 1096 mm$^3$ and tumor weight of 0.93 g. The result indicates that Ab612 (78.2% tumor growth inhibition rate (IR)) exhibited 1.4-fold higher tumor growth inhibition compared to Ab417 (55.5% IR), based on tumor weight (FIG. 3C). FIG. 3D shows the tumor images of each group of eight mice sacrificed after the end of the experiment as described in FIGS. 3A-3C. The size of the cancer tissues extracted from eight mice treated with Ab612 antibody is smaller than those treated with Ab417 antibody. The anti-cancer effect of the Ab612 antibody seems to work well in vivo, resulting in the improvement of the tumor microenvironment (TME) through antibody infiltration into cancer tissue or immune cell-based assault environment.

Therefore, the group treated with Ab612 antibody disclosed herein showed significant inhibitory effect on tumor growth, compared to the group administered with the negative control. In addition, no body weight loss was observed in the mice during administration and no toxicity by administration of the antibody was observed.

The foregoing description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other aspects of the invention will be apparent to those skilled in the art from consideration of the specification and practice of the invention disclosed herein. It is intended that the specification and examples be considered as exemplary only, with a true scope and spirit of the invention being indicated by the following claims.

All publications, patents, and patent applications disclosed herein are incorporated by reference to the same extent as if each individual publication, patent or patent application was specifically and individually indicated to be incorporated by reference.

What is claimed is:

1. An isolated antibody or antigen-binding fragment thereof that specifically binds to L1 Cell Adhesion Molecule (L1CAM), wherein
the antibody or antigen-binding fragment thereof comprises a heavy chain variable region (VH) complementarity determining region 1 (CDR1), CDR2, and CDR3 and a light chain variable region (VL) CDR1, CDR2, and CDR3;
(i) wherein the VH CDR1, VH CDR2, and VH CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, VL CDR2, and VL CDR3 comprises RASRTISSYVN (SEQ ID NO: 12), AASNLHS (SEQ ID NO: 7), and QQSIGRGPVT (SEQ ID NO: 13), respectively;
(ii) wherein the VH CDR1, VH CDR2, and VH CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, VL CDR2, and VL CDR3 comprises RASRTISSYVN (SEQ ID NO: 12), AASNLHS (SEQ ID NO: 7), and QQAGFYSPWT (SEQ ID NO: 17), respectively;
(iii) wherein the VH CDR1, VH CDR2, and VH CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, VL CDR2, and VL CDR3 comprises RASRTISSYVN (SEQ ID NO: 12), AASNLHS (SEQ ID NO: 7), and QQAGFYTPWT (SEQ ID NO: 15), respectively;
(iv) wherein the VH CDR1, VH CDR2, and VH CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, VL CDR2, and VL CDR3 comprises RASRTISSYVN (SEQ ID NO: 12), AASNLHS (SEQ ID NO: 7), and QQSLHFYPWT (SEQ ID NO: 19), respectively; or
(v) wherein the VH CDR1, VH CDR2, and VH CDR3 comprises RFGMH (SEQ ID NO: 2), FISNEGSNKYYADSVKG (SEQ ID NO: 10), and GRAYGSGSLFDP (SEQ ID NO: 4), respectively; and wherein the VL CDR1, VL CDR2, and VL CDR3 comprises RASRTISSYVN (SEQ ID NO: 12), AASNLHS (SEQ ID NO: 7), and QQSLVWYPWT (SEQ ID NO: 21), respectively.

2. The antibody or antigen-binding fragment thereof of claim 1, comprising a heavy chain CDR1, CDR2, and CDR3 and a light chain CDR1, CDR2, and CDR3, wherein the light chain CDR1 comprises RASRTISSYVN (SEQ ID NO: 12), the light chain CDR2 comprises AASNLHS (SEQ ID NO: 7), the light chain CDR3 comprises QQSIGRGPVT (SEQ ID NO:13), the heavy chain CDR1 comprises RFGMH (SEQ ID NO: 2), the heavy chain CDR2 comprises FISNEGSNKYYADSVKG (SEQ ID NO: 10), and the heavy chain CDR3 comprises GRAYGSGSLFDP (SEQ ID NO: 4).

3. The antibody or antigen-binding fragment thereof of claim 1, wherein the antibody or antigen-binding fragment thereof has one or more characteristics of:
(a) the antibody or antigen-binding fragment thereof exhibits improved productivity;

(b) the antibody or antigen-binding fragment thereof exhibits improved affinity as measured by the equilibrium dissociation constant ($K_D$);
(c) the antibody or antigen-binding fragment thereof exhibits improved isoelectric point (PI) value,
(d) the antibody or antigen-binding fragment thereof exhibits improved affinity as measured by the association constant ($K_A$); or
(e) any combination thereof.

4. The antibody or antigen-binding fragment thereof of claim 3, wherein the improved productivity is at least 55 mg/L, at least 56 mg/L, at least 57 mg/L, at least 58 mg/L, at least 59 mg/L, at least about 60 mg/L, at least about 61 mg/L, at least about 62 mg/L, at least about 63 mg/L, at least about 64 mg/L, at least about 65 mg/L, at least about 66 mg/L, at least about 67 mg/L, at least about 68 mg/L, at least about 69 mg/L, at least about 70 mg/L, at least about 71 mg/L, at least about 72 mg/L, at least about 73 mg/L, at least about 74 mg/L, at least about 75 mg/L, at least about 76 mg/L, at least about 77 mg/L, at least about 78 mg/L, at least about 79 mg/L, at least about mg/L, at least about 81 mg/L, at least about 82 mg/L, at least about 83 mg/L, at least about 84 mg/L, or at least about 85 mg/L;
wherein the improved Ku is less than $2.6\times10^{-10}$ M, less than $2.5\times-10^{-10}$ M, less than $2.0\times10^{-10}$ M, less than $1.5\times10^{-10}$ M, less than $1.0\times10^{-10}$ M, less than $9\times10^{-11}$ M, less than $8\times10^{-11}$ M, less than $7\times10^{-11}$ M, less than $6\times10^{-11}$ M, less than $5\times10^{-11}$ M, less than $4\times10^{-11}$ M, less than $3\times10^{-11}$ M, less than $2\times10^{-11}$ M, less than $1\times10^{-11}$ M, less than $9\times10^{-12}$ M, less than $8\times10^{-12}$ M, less than $7\times10^{-12}$ M, less than $6\times10^{-12}$ M, less than $5\times10^{-12}$ M, less than $4\times10^{-12}$ M, less than $3\times10^{-12}$ M, less than $2\times10^{-12}$ M, less than $1\times10^{-12}$ M, less than $9\times10^{-13}$ M, or less than $8\times10^{-13}$ M;
wherein the improved affinity is less than $5\times10^{-10}$ M, less than $4\times10^{-10}$ M, less than $3\times10^{-10}$ M, less than $2\times10^{-10}$ M, less than $1.0\times10^{-10}$ M, less than $9\times10^{-11}$ M, less than $8\times10^{-11}$ M, less than $7\times10^{-11}$ M, less than $6\times10^{-11}$ M, less than $5\times10^{-11}$ M, less than $4\times10^{-11}$ M, less than $3\times10^{-11}$ M, less than $2\times10^{-11}$ M, less than $1\times10^{-11}$ M, less than $9\times10^{-12}$ M, less than $8\times10^{-12}$ M, less than $7\times10^{-12}$ M, less than $6\times10^{-12}$ M, less than $5\times10^{-12}$ M, less than $4\times10^{-12}$ M, less than $3\times10^{-12}$ M, less than $2\times10^{-12}$ M, less than $1\times10^{-12}$ M, less than $9\times10^{-13}$ M, or less than $8\times10^{-13}$ M; and/or
wherein the improved PI Value is less than 9.6, less than 9.5, less than 9.4, less than 9.3, less than 9.2, less than 9.1, less than 9.0, less than 8.9, less than 8.8, less than 8.7, less than 8.6, less than 8.5, less than 8.4, less than 8.3, less than 8.2, less than 8.1, less than 8.0, less than 7.9, less than 7.8, less than 7.7, or less than 7.6.

5. The antibody or antigen-binding fragment thereof of claim 1,
wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGGVVQPGGSLRLSCAASGFTESREGMHWVRQAPGKGLEWVAFSNEGSNKYYADSVKGRFTSRDNSANTLY LQMNSLRAEDTAVYYCARGRAYGSGSLFDPWGQGTLVTVSS (SEQ ID NO: 23) and wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DQLTQSPSSLSASVGDRVTTCRASRTSSYVNWYRQRPGKAPESLIYAASNLHSGVPSRFSGSGSGTDFTLTSSLQP EDFATYYCQQSIGRGPVTFGQGTKLEIK (SEQ ID NO: 24);
wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGGVVQPGGSLRLSCAASGFTESREGMHWVRQAPGKGLEWVAFSNEGSNKYYADSVKGRFTSRDNSANTLY LQMNSLRAEDTAVYYCARGRAYGSGSLFDPWGQGTLVTVSS (SEQ ID NO: 27) and wherein the VL, comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DQLTQSPSSLSASVGDRVTTCRASRTSSYVNWYRQRPGKAPESLIYAASNLHSGVPSRFSGSGSGTDFTLTSSLQP EDFATYYCQQAGFYSPWTFGQGTKLEIK (SEQ ID NO: 28);
wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGGVVQPGGSLRLSCAASGFTESREGMHWVRQAPGKGLEWVAFSNEGSNKYYADSVKGRFTSRDNSANTLY LQMNSLRAEDTAVYYCARGRAYGSGSLFDPWGQGTLVTVSS (SEQ ID NO: 25) and wherein the VL, comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DQLTQSPSSLSASVGDRVTTCRASRTSSYVNWYRQRPGKAPESLIYAASNLHSGVPSRFSGSGSGTDFTLTSSLQP EDFATYYCQQAGFYTPWTFGQGTKLEIK (SEQ ID NO: 26);
wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGGVVQPGGSLRLSCAASGFTESREGMHWVRQAPGKGLEWVAFSNEGSNKYYADSVKGRFTSRDNSANTLY LQMNSLRAEDTAVYYCARGRAYGSGSLFDPWGQGTLVTVSS (SEQ ID NO: 29) and wherein the VL comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DQLTQSPSSLSASVGDRVTTCRASRTSSYVNWYRQRPGKAPESLIYAASNLHSGVPSRFSGSGSGTDFTLTSSLQP EDFATYYCQQSLHFYPWTFGQGTKLEIK (SEQ ID NO: 30); or wherein the VH comprises an amino acid sequence which is at least about 80%, at least about 85%, at least about 90%, at least about 95%, at least about 96%, at least about 97%, at least about 98%, at least about 99%, or about 100% identical to the amino acid sequence set forth as EVQLVESGGGVVQPGGSLRLSCAASGFTESREGMHWVRQAPGKGLEWVAFSNEGSNKYYADSVKGRFTSRDNSANTLY LQMNSLRAEDTAVYYCARGRAYGSGSLFDPWGQGTLVTVSS (SEQ ID NO: 31) and wherein the VL, comprises an amino acid sequence which is at least about 80%, at least about 85%, at least about 90%, at least about 95%, at least about 96%, at least about 97%, at least about 98%, at least about 99%, or about 100% identical to the amino acid sequence set forth as DQLTQSPSSLSASVGDRVTTCRAS-RTSSYVNWYRQRPGKAPESLI-YAASNLHSGVPSRFSGSGSGTDFTLTSSLQP EDFATYYC QQSLVWYPWTFGQGTKLEIK (SEQ ID NO: 32).

6. A nucleic acid encoding the antibody or antigen-binding fragment thereof of claim 1.

7. A vector comprising the nucleic acid of claim 6.

8. A host cell comprising the vector of claim 7.

9. An immunoconjugate comprising the antibody or antigen-binding fragment thereof of claim 1, linked to an agent.

10. A bispecific or multispecific antibody comprising the antibody or antigen-binding fragment thereof of claim 1, and an antibody or antigen-binding fragment thereof that binds to an antigen.

11. A composition comprising the antibody or antigen-binding fragment thereof of claim 1, and a carrier.

12. A kit comprising the antibody or antigen-binding fragment thereof of claim 1.

13. An immune cell comprising the nucleic acid of claim 6.

14. The immune cell of claim 13, which is a T cell or an NK cell.

15. An immune cell which comprises a chimeric antigen receptor comprising the antibody or antigen-binding fragment thereof of claim 1.

16. A method of producing an antibody or an antigen-binding fragment thereof which specifically binds to a human L1CAM protein, comprising culturing the cell of claim 8 under suitable conditions and isolating the antibody.

17. A method of treating a disease or condition in a subject in need thereof, comprising administering to the subject the antibody or antigen-binding fragment thereof of claim 1, wherein the disease or condition comprises a tumor.

18. The method of claim 17, further comprising administering an additional therapeutic agent.

19. An antibody or antigen-binding fragment thereof specifically binding to L1CAM, wherein the antibody or antigen-binding fragment thereof comprises a VH and a VL, wherein the VH of the antibody or antigen-binding fragment thereof comprises SEQ ID NO: 23 and the VL of the antibody or antigen-binding fragment thereof comprises SEQ ID NO: 24.

20. The antibody or antigen-binding fragment thereof of claim 5, wherein the antibody or antigen-binding fragment thereof further comprises a heavy chain (HC) constant region and a light chain (LC) constant region, wherein the HC constant region comprises amino acids 122 to 451 of SEQ ID NO: 38 and the LC constant region comprises amino acids 109 to 215 of SEQ ID NO: 39.

* * * * *